US010597408B2

(12) United States Patent
Yaghi et al.

(10) Patent No.: US 10,597,408 B2
(45) Date of Patent: Mar. 24, 2020

(54) COVALENT ORGANIC FRAMEWORKS WITH A WOVEN STRUCTURE

(71) Applicant: The Regents of the University of California, Oakland, CA (US)

(72) Inventors: Omar M. Yaghi, Berkeley, CA (US); Yuzhong Liu, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/774,582

(22) PCT Filed: Nov. 25, 2016

(86) PCT No.: PCT/US2016/063774
§ 371 (c)(1),
(2) Date: May 8, 2018

(87) PCT Pub. No.: WO2017/091814
PCT Pub. Date: Jun. 1, 2017

(65) Prior Publication Data
US 2018/0319821 A1 Nov. 8, 2018

Related U.S. Application Data

(60) Provisional application No. 62/260,458, filed on Nov. 27, 2015.

(51) Int. Cl.
C07F 1/08 (2006.01)
C07D 471/02 (2006.01)
B01J 20/22 (2006.01)
C01B 37/00 (2006.01)
C07D 471/04 (2006.01)

(52) U.S. Cl.
CPC .............. *C07F 1/08* (2013.01); *B01J 20/226* (2013.01); *C01B 37/00* (2013.01); *C07D 471/04* (2013.01)

(58) Field of Classification Search
CPC .............................. C07F 1/08; C07D 471/02
USPC ..................................................... 546/10, 88
See application file for complete search history.

(56) References Cited

U.S. PATENT DOCUMENTS

| | | |
|---|---|---|
| 2,684,967 A | 7/1954 | Berg |
| 4,532,225 A | 7/1985 | Tsao |
| 5,064,804 A | 11/1991 | Soo |
| 5,160,500 A | 11/1992 | Chu |
| 5,208,335 A | 5/1993 | Ramprasad |
| 5,648,508 A | 7/1997 | Yaghi |
| 5,733,505 A | 3/1998 | Goldstein |
| 5,779,904 A | 7/1998 | Ruderman |
| 6,479,447 B2 | 11/2002 | Bijl |
| 6,501,000 B1 | 12/2002 | Stibrany |
| 6,617,467 B1 | 9/2003 | Mueller |
| 6,624,318 B1 | 9/2003 | Mueller |
| 6,686,428 B2 | 2/2004 | Zhang |
| 6,893,564 B2 | 5/2005 | Mueller |
| 6,929,679 B2 | 8/2005 | Mueller |
| 6,930,193 B2 | 8/2005 | Yaghi |
| 7,196,210 B2 | 3/2007 | Yaghi |
| 7,202,385 B2 | 4/2007 | Mueller |
| 7,229,943 B2 | 6/2007 | Gibson |
| 7,279,517 B2 | 10/2007 | Mueller |
| 7,309,380 B2 | 12/2007 | Mueller |
| 7,343,747 B2 | 3/2008 | Mueller |
| 7,411,081 B2 | 8/2008 | Mueller |
| 7,524,444 B2 | 4/2009 | Hesse |
| 7,582,798 B2 | 9/2009 | Yaghi |
| 7,637,983 B1 | 12/2009 | Liu |
| 7,815,716 B2 | 10/2010 | Mueller |
| 8,343,260 B2 | 1/2013 | Omary |
| 8,480,955 B2 | 7/2013 | Yaghi |
| 8,501,150 B2 | 8/2013 | Schubert |
| 8,518,264 B2 | 8/2013 | Kiener |
| 8,524,932 B2 | 9/2013 | Leung |
| 8,709,134 B2 | 4/2014 | Yaghi |
| 8,735,161 B2 | 5/2014 | Yaghi |
| 8,742,152 B2 | 6/2014 | Yaghi |
| 9,078,922 B2 | 7/2015 | Yaghi |
| 2003/0004364 A1 | 1/2003 | Yaghi |
| 2003/0078311 A1 | 4/2003 | Muller |
| 2003/0148165 A1 | 8/2003 | Muller |

(Continued)

FOREIGN PATENT DOCUMENTS

| | | |
|---|---|---|
| CN | 1910191 A | 2/2007 |
| CN | 101270094 A | 9/2008 |

(Continued)

OTHER PUBLICATIONS

Neogi, S. et al.: Heteroleptic metallosupramolecular racks, rectangles, and trigonal prisms: stoichiometry-controlled reversible interconversion. Inorganic Chem., vol. 52, pp. 6975-6984, 2013.*
Kalsani, V. et al.: Novel Phenathroline ligands and their kinetically locked Copper(1) complexes with unexpected photophysical properties. Inorganic Chem., vol. 45, pp. 2061-2067, 2006.*
Prikhod'Ko et al., "Iron(II)-Templated Synthesis of [3]Rotaxanes by Passing Two Threads through the Same Ring," J. Am. Chem. Soc. 130:448-449, Dec. 19, 2007.
Ren et al., "The variety of conformational isomerism of a flexible organic linker induced by the position and amounts of aromatic carboxylic groups," Polyhedron, 83:130-136, 2014.

(Continued)

*Primary Examiner* — Charanjit Aulakh
(74) *Attorney, Agent, or Firm* — Gavrilovich, Dodd & Lindsey LLP

(57) ABSTRACT

The disclosure provides for covalent organic frameworks (COFs) that constructed from weaving a plurality of long organic threads together. In particular, the disclosure provides for the construction of woven COFS, where long organic strands are connected together in a woven pattern using organic ligands/complexes that when orientated in certain geometries are capable of reversibly binding metal ions.

15 Claims, 22 Drawing Sheets

(56) References Cited

U.S. PATENT DOCUMENTS

| | | |
|---|---|---|
| 2003/0222023 A1 | 12/2003 | Mueller |
| 2004/0081611 A1 | 4/2004 | Muller |
| 2004/0225134 A1 | 11/2004 | Yaghi |
| 2004/0249189 A1 | 12/2004 | Mueller |
| 2004/0265670 A1 | 12/2004 | Muller |
| 2005/0004404 A1 | 1/2005 | Muller |
| 2005/0014371 A1 | 1/2005 | Tsapatsis |
| 2005/0124819 A1 | 6/2005 | Yaghi |
| 2005/0154222 A1 | 7/2005 | Muller |
| 2005/0192175 A1 | 9/2005 | Yaghi |
| 2006/0057057 A1 | 3/2006 | Muller |
| 2006/0135824 A1 | 6/2006 | Mueller |
| 2006/0154807 A1 | 7/2006 | Yaghi |
| 2006/0185388 A1 | 8/2006 | Muller |
| 2006/0252641 A1 | 11/2006 | Yaghi |
| 2006/0252972 A1 | 11/2006 | Pilliod |
| 2006/0287190 A1 | 12/2006 | Eddaoudi |
| 2007/0068389 A1 | 3/2007 | Yaghi |
| 2007/0202038 A1 | 8/2007 | Yaghi |
| 2007/0217982 A1 | 9/2007 | Wright |
| 2007/0248575 A1 | 10/2007 | Connor |
| 2008/0017036 A1 | 1/2008 | Schultink |
| 2008/0190289 A1 | 8/2008 | Muller |
| 2009/0155588 A1 | 6/2009 | Hesse |
| 2009/0183996 A1 | 7/2009 | Richter |
| 2009/0216059 A1 | 8/2009 | Reyes |
| 2009/0247654 A1 | 10/2009 | Rajendran |
| 2010/0069234 A1 | 3/2010 | Willis |
| 2011/0015388 A1 | 1/2011 | Youngblood |
| 2011/0282067 A1 | 11/2011 | Li |
| 2011/0282071 A1 | 11/2011 | Shi |
| 2012/0028846 A1 | 2/2012 | Yaghi |
| 2012/0031268 A1 | 2/2012 | Yaghi |
| 2012/0130113 A1 | 5/2012 | Yaghi |
| 2012/0133939 A1 | 5/2012 | Yaghi |
| 2013/0047849 A1 | 2/2013 | Zhang |
| 2013/0096210 A1 | 4/2013 | Yaghi |
| 2014/0037944 A1 | 2/2014 | Dichtel |
| 2014/0148596 A1 | 5/2014 | Dichtel |
| 2014/0231787 A1* | 8/2014 | Ishige et al. ........ H01L 51/5004 313/504 |

FOREIGN PATENT DOCUMENTS

| | | |
|---|---|---|
| DE | 102005023856 A1 | 11/2006 |
| DE | 102005054523 A1 | 5/2007 |
| EP | 1070538 A2 | 1/2001 |
| JP | 2007534658 A | 11/2007 |
| KR | 20100055350 A | 5/2010 |
| WO | 9905151 A1 | 2/1999 |
| WO | 03035717 A1 | 5/2003 |
| WO | 2006047423 A2 | 5/2006 |
| WO | 2006110740 A2 | 10/2006 |
| WO | 2006122920 A1 | 11/2006 |
| WO | 2006125761 A2 | 11/2006 |
| WO | 2007007113 A2 | 1/2007 |
| WO | 2007118843 A1 | 10/2007 |
| WO | 2009073739 A1 | 6/2009 |
| WO | 2010056092 A2 | 5/2010 |
| WO | 2010080618 A2 | 7/2010 |
| WO | 2010083418 A1 | 7/2010 |
| WO | 2011/127301 A2 | 10/2011 |
| WO | 2011127301 A2 | 10/2011 |
| WO | 2011146155 A2 | 11/2011 |
| WO | 2012012495 A2 | 1/2012 |
| WO | 2012082213 A2 | 6/2012 |
| WO | 2012100224 A2 | 7/2012 |
| WO | 2012106451 A2 | 8/2012 |

OTHER PUBLICATIONS

Kaluza, Nicoleta, International Search Report and Written Opinion, European Patent Office, PCT/US2016/063774, dated Mar. 21, 2017.

Nickitas-Etienne, Athina, International Preliminary Report on Patentability and Written Opinion, PCT/US2016/063774, The International Bureau of WIPO, dated Jun. 7, 2018.

Doonan et al., 'Exceptional ammonia uptake by a covalent organic framework,' Nature Chem. 2:235-238 (2010).

Du et al., "Direction of unusual mixed-ligand metal-organic frameworks: a new type of 3-D polythreading involving 1-D and 2-D structural motifs and a 2-fold interpenetrating porous network", Chem. Commun., 2005, 5521-5523.

Dugan et al., 'Covalent modification of a metal-organic framework with isocyanates: probing substrate scope and reactivity,' 29:3366-3368 (2008).

Duval, Eric, International Search Report and Written Opinion, Application No. PCT/US2015/023173, dated Apr. 11, 2016.

Eberhard, Michael, Extended European Search Report, EP11810321, dated Jan. 14, 2014.

Eberhard, Michael, International Search Report and Written Opinion, PCT/US2012/059877, European Patent Office, dated Oct. 15, 2013.

Eddaoudi, M et al., "Systematic Design of Pore Size and Functionality in Isoreticular MOFs and Their application in Methane Storage" Science, (2002), vol. 295, pp. 469-472.

Eiichiro Mizushima, Notice of Reasons for Rejection, Japanese Patent Application No. 2012-516363, dated Aug. 26, 2014.

El-Kaderi et al., 'Designed Synthesis of 3D Covalent Organic Frameworks,' Science 316:268-272 (2007).

El-Kaderi et al., "Supporting Online Material for Designed Synthesis of 3D Covalent Organic Frameworks", Science 316, 268 (2007).

El-Kaderi, Hani M., et al., "Designed Synthesis of 3D Covalent Organic Frameworks", Science 316, 268 (Published Apr. 13, 2007), S1-S75.

Fang et al. A Metal-Organic Framework with the Zeolite MTN Topology Containing Large Cages of vol. 2.5 nm3. Ang Chem Int Ed 2005, vol. 44, pp. 3845-3848.

Fei et al., 'A Nearly Planar Water Sheet Sndwiched between Strontium-Imidazolium Carboxylate Coordination Polymers,' Inorg. Chem., 2005, pp. 5200-5202, vol. 44.

Finger, Gabriela, International Search Report and Written Opinion, PCT/US2010/043373, European Patent Office, dated Oct. 6, 2010.

Finger, Gabriela, International Search Report and Written Opinion, PCT/US2015/021107, European Patent Office, dated Aug. 17, 2015.

First Office Action issued in Chinese Patent Application No. 201180045210.8, dated Sep. 28, 2014.

Forster et al., 'A High-Throughput Investigation of the Role of pH, Temperature, Concentration, and Time on the Synthesis of Hybrid Inorganic-Organic Materials,' Angew. Chemie Int. Ed. 44(46):7608-7611 (2005).

Fracaroli et al., 'Isomers of Metal-Organic Complex Arrays,' Inorg. Chem. 51: 6437-6439 (Jun. 5, 2012).

Fracaroli, A.M. et al., Metal-organic Frameworks with Precisely Designed Interior for Carbon Dioxide Capture in the Presence of Water, J. Am. Chem. Soc, Jun. 25, 2014, vol. 136, No. 25, pp. 8863-8866.

Furkawa et al., 'Isoreticular Expansion of MetalOrganic Frameworks with Triangular and Square Building Units and the Lowest Calculated Density for Porous Crystals,' Inorg. Chem. 50:9147-9152 (2011).

Furukawa et al., 'Storage of Hydrogen, Methane, and Carbon Dioxide in Highly Porous Covalent Organic Frameworks for Clean Energy Applications,' J. Am. Chem. Soc. 25:8876-8883 (2009).

Furukawa et al., "Water Adsorption in Porous Metal-Organic Frameworks and Related Materials," J. of the Amer. Chem. Soc, vol. 136, No. 11, pp. 4369-4381, Published: Mar. 3, 2014.

Gadzikwa, T. et al., 'Selective Bifunctional Modification of a Non-catenated Metal-Organic Framework Material via Click Chemistry,' J. Am. Chem. Soc. 131:13613-13615 (2009).

Galli et al., 'Adsorption of Harmful Organic Vapors by Flexible Hydrophobic Bis-pyrazolate Based MOFs,' Chem. Mater. 22(5):1664-1672 (2010).

Gandara et al., 'High Methane Storage Capacity in Aluminum Metal-Organic Frameworks', Journal of the American Chemical Society, vol. 136, No. 14, Mar. 21, 2014, pp. 5271-5274.

(56) References Cited

OTHER PUBLICATIONS

Gandara et al., 'Porous, Conductive Metal-Triazolates and Their Structural Elucidation by the Charge-Flipping Method,' Chem. Eur. J. 18:10595-10601 (2012).
Gandara, Felipe, et al., "Crystallography of metal-organic frameworks", IUCRJ, vol. 1, No. 6, Oct. 28, 2014, pp. 563-570.
Garibay et al., "Isoreticular synthesis and modification of frameworks with the UiO-66 topology," Chemical Communications, 46:7700-7702, Sep. 27, 2010.
Gassensmith et al., 'Strong and Reversible Binding of Carbon Dioxide in a Green Metal-Organic Framework,' J. Am. Chem. Soc. 133:15312-15315 (Aug. 30, 2011).
Gonzalez-Arellano et al., 'Homogeneous and heterogeneous Au(III) Schiff base-complexes as selective and general catalysts for self-coupling of aryl boronic acids,' Chem. Comm 15:1990-1992 (2005).
Goto, Y et al., "Clickable Metal-Organic Framework," J. Am. Chem. Soc. 130:14354-14355 (2008).
Han et al., 'Covalent Organic Frameworks as Exceptional Hydrogen Storage Materials,' J. Am. Chem. Soc. 130: 11580-11581 (2008).
Hassan et al., "Aryl-Aryl Bond Formation One Century After the Discovery of the Ullmann Reaction", Chem. Rev., Published on Web: Mar. 8, 2002, 102, 1359-1469.
Hmadeh et al., 'New Porous Crystals of Extended Metal-Catecholates,' J. Chem. Mater. 24:3511-3513 (Aug. 28, 2012).
Holler et al., 'The first dinitrile frameworks of the rare earth elements: [LnCl3(1,4-Ph(CN)2] and [Ln2Cl6(1,4Ph(CN) 2], Ln = Sm, Gd, Tb, Y; Access to novel metal-organic frameworks by solvent free synthesis in molten 1,4-benodinitrile,' Inorganic Chemistry 47(21): 10141-9 (2008).
Holler et al., "The First Dintrile Frameworks of the Rare Earth Elements: 3[LnCL3(1,4-Ph(CN2)] and 3[Ln2Cl6(1,4-Ph (CN)2)], Ln=Sm, Gd, Tb, Y; Access to Novel Metal-Organic Frameworks by Solvent Free Synthesis in Molten 1,4-Benzodinitrile," Inorganic Chemistry, 2008, pp. 10141-10149, vol. 47, No. 21.
Holler, Christoph J.,et. al., "The first dinitrile frameworks of the rare earth elements: [LnCl3(1,4-Ph(CN)2] and [Ln2Cl6(1,4Ph(CN)2], Ln = Sm, Gd, Tb, Y;Access to novel metal-organic frameworks by solvent free synthesis in molten 1,4-benzodinitril", Inorganic Chemistry, (Aug. 10, 2008), vol. 47, No. 21, p. 10141, XP002574067.
Huang et al., 'Ligand-Directed Strategy for Zeolite-Type Metal—Organic Frameworks: Zinc(ii) Imidazolates with Unusual Zeolitic Topologies,' Angew. Chem. Int. Ed. 45:1557-1559 (2006).
Hunt et al., 'Reticular Synthesis of Covalent Organic Borosilicate Frameworks,' J. Am. Chem. Soc. 130: 11872-11873 (2008).
Hurenkamp, Jaap, International Search Report and Written Opinion, PCTUS2015/016555, European Patent Office, dated May 6, 2015.
Ingleson et al., 'Framework fractionalization triggers metal complex binding,' Chem. Comm. 23:2680-2682 (2008).
Jia, Xiao, The Third Office Action, Chinese Patent Application No. 201080021284.2, dated Aug. 19, 2014.
Jones, Christopher. Nonfinal Office Action for U.S. Appl. No. 12/598,855. dated Oct. 12, 2012.
Jones, Christopher. Nonfinal Office Action for U.S. Appl. No. 12/598,855. dated Jun. 14, 2012.
Kandiah et al., 'Post-synthetic modification of the metal-organic framework compound Ui0-66,' J. of Mater. Chem., vol. 20, No. 44, pp. 9848-9851, 2010.
Kim et al., "Isoreticular MOFs based on a rhombic dodecahedral MOP as a tertiary building unit", CrystEngComm, Mar 3, 2014, vol. 16, pp. 6391-6397.
Kim, Su Mi, International Search Report and Written Opinion, Application No. PCT/US09/046463, dated Feb. 24, 2010.
Kim, Su Mi, International Search Report and Written Opinion, PCT/US2010/039154, Korean Intellectual Property Office, dated Feb. 23, 2011.
Kirai et al., 'Homocoupling of arylboronic acids catalyzed by 1,10-phenanthroline—ligated copper complexes in air,' European Journal of Organic Chemistry 12:1864-1867 (2009).

Klaes, Daphane, International Search Report and Written Opinion for PCT/US2010/021201, European Patent Office, dated Apr. 27, 2010.
Klein et al., 'Combinatorial Material Libraries on the Microgram Scale with an Example of Hydrothermal Synthesis,' Angew. Chemie 37(24):3369-3372 (1998).
Klemperer et al., "New Directions in Polyvanadate Chemistry: From Cages and Clusters to Baskets, Belts, Bowls, and Barrels", Angew. Chem. Int. Ed. Engl. 31 (1992) No. 1, pp. 49-51.
Koh et al., 'A Crystalline Mesoporous Coordination Copolymer with High Microporosity,' Angew Chem Int'l, 2008, pp. 677-680, vol. 47.
Koh et al., "A Crystalline Mesoporous Coordination Copolymer with High Microporosity", Angew. Chem. Int. Ed. 2008, 120, pp. 689-692.
Koh, Kyoungmoo, et al., "A Crystalline Mesoporous Coordination Copolymer with High Microporosity", Angewandte Chemie International Edition, (Jan. 11, 2008), vol. 47, No. Issue, pp. 689-692, XP008150670.
Kokubo, Atsuki, Office Action, Japanese Patent Application No. 2012-553065, dated Feb. 3, 2015.
Kong et al., 'Mapping of Functional Groups in Metal-Organic Frameworks', Science, vol. 341, No. 6148, Jul. 25, 2013, pp. 882-885.
Koza et al., 'An efficient High Yielding Approach for the Homocoupling of Aryl Boronic Acids,' Synthesis 15:2183-2186 (2002).
Kyoungmoo et al., "A Crystalline Mesoporous Coordination Copolymer with High Microporosity," Angew. Chem. Int. Ed. 47(4):689-92 (2008).
Lange, Tim, International Search Report, Application No. PCT/US2015/021090, dated Sep. 21, 2015.
Lawrence, Frank M. Nonfinal Office Action for U.S. Appl. No. 12/699,616 dated Apr. 10, 2012.
Lawrence, Frank M., Non-Final Office Action for U.S. Appl. No. 12/699,616, United States Patent and Trademark Office, dated Aug. 3, 2012.
Lee et al., 'Synthesis and Gas Sorption Properties of a Metal-Azolium Framework (MAF) Material,' Inorganic Chemistry, Nov. 2, 2009, pp. 9971-9973, vol. 48, No. 21.
Lee, Ji Min, International Search Report and Written Opinion, Application No. PCT/US2010/039284, dated Feb. 23, 2011.
Leus et al., "The remarkable catalytic activity of the saturated metal organic framework V-MIL-47 in the cyclohexene oxidation", Chem. Comm. Jun. 18, 2010, 46, 5085-5087.
Li et al., 'Synthesis and Structural Characterization of a New 3D Lead Coordination Polymer with a Tetrazole-1-acetate Ligand,' Chinese J. Struct. Chem. 30(7): 1049-1053 (2011).
Li, Y. et al., 'Hydrogen Storage in Metal-Organic and Covalent-Organic Frameworks by Spillover,' AIChe Journal 54 (1):269-279 (2008).
Lindner, Nora, International Preliminary Report on Patentability and Written Opinion, The International Bureau of WIPO, PCT/US2011/044625, dated Jan. 31, 2013.
Ling et al., 'A zinc(II) metal-organic framework based on triazole and dicarboxylate ligands for selective adsorption of hexane isomers,' Chem. Comm. 47:7197-7199 (2011).
Liu, Lei, First Office Action, Chinese Patent Application No. 201180009370.6,The State Intellectual Property Office of the People's Republic of China, dated Mar. 3, 2014.
Liu., Y., "Dynamic Chirality in Donor-Acceptor Pretzelanes", Journal of Organic Chemistry, 2005, 70, 9334-9344.
Loeb, 'Rotaxanes as ligands: from molecules to materials', Chem. Soc. Rev., 2007, 36, 226-235.
Luo et al., 'Two new metal-triazole-benzenedicarboxylate frameworks affording an uncommon 3,4-connected net and unique 4,6-connected rod packing: hydrothermal synthesis, structure, thermostability and luminescence studies,' CrystEngComm 11 (6): 1097-1102 (2009).
Mashiyama, Shinya, Office Action issued in Japanese Patent Application No. 2012-522962, Japanese Patent Office, dated May 27, 2014.

(56) References Cited

OTHER PUBLICATIONS

Mason, Jarad A., "Evaluating metal-organic frameworks for natural gas storage", Chemical Science, vol. 5, Accepted Oct. 22, 2013, pp. 32-51.

McDonald, Thomas M. et al., 'Capture of Carbon Dioxide from Air and Flue Gas in the Alkylamine-Appended Metal-Organic Framework mmen-Mg 2 (dobpdc)', Journal of the American Chemical Society, vol. 134, No. 16, Apr. 4, 2012, pp. 7056-7065.

Mendoza-Cortes et al., 'Adsorption Mechanism and Uptake of Methane in Covalent Organic Frameworks: Theory and Experiment,' J. Phys. Chem. 114:10824-10833 (2010).

Meneses, Ociel Esau Andrade, First Office Action, Mexican Application No. MX/a/2013/00469, Mexican Institute of Industrial Property (IMPI), dated Jan. 26, 2015.

Mineko Mohri, International Preliminary Report on Patentability and Written Opinion, PCT/US2015/016555, The International Bureau of WIPO, dated Sep. 1, 2016.

Morris et al., 'Framework mobility in the metal-organic framework crystal IRMOF-3: Evidence for aromatic ring and amine rotation,' Journal of Molecular Structure 1004:94-101 (2011).

Morris et al., 'NMR and X-ray Study Revealing the Rigidity of Zeolitic Imidazolate Frameworks,' J. Phys. Chem. 116 (24):13307-13312 (Jun. 1, 2012).

Morris et al., 'Synthesis, Structure, and Metalation of Two New Highly Porous Zirconium Metal-Organic Frameworks,' Inorg. Chem. 51:6443-6445 (Jun. 7, 2012).

Morris, et al., 'Crystals as Molecules: Postsynthesis Covalent Functionalization of Zeolitic Imidazolate Frameworks', J. Am. Chem. Soc., (Aug. 2008), vol. 130, No. 38, pp. 12626-12627.

Moyse, Ellen, International Preliminary Report on Patentability and Written Opinion, PCT/US08/006008, The International Bureau of WIPO, dated Nov. 26, 2009.

Mulfort et al., 'Chemical Reduction of Metal-Organic Framework Materials as a Method to Enhance Gas Uptake and Binding,' J. Am. Chem. Soc. 129:9604-9605 (2007).

Mulhausen, Dorothee, International Preliminary Report on Patentability, PCT/US2010/021201, The International Bureau of WIPO, dated Jul. 28, 2011.

Nickitas-Etienne, Athina, International Preliminary Report on Patentability and Written Opinion, Application No. PCT/US2015/023173, dated Oct. 4, 2016.

Nickitas-Etienne, Athina, International Preliminary Report on Patentability and Written Report, Application No. PCT/US2015/021090, dated Sep. 20, 2016.

Nickitas-Etienne, Athina, International Preliminary Report on Patentability, PCT/US2009/068731, The International Bureau of WIPO, dated Jun. 30, 2011.

Niu et al., 'Synthesis and structural characterization of the one dimensional polymers [Rh2(OAc)4(NCPhCN)S, S = CH3COCH3, CH3OH, C2H5OH, C4H80, and C6H6,' Polyhedron 17(23-24):4079-89 (1998).

Novoa, Carlos, International Search Report and Written Opinion for PCT/US2010/021201, European Patent Office dated Apr. 27, 2010.

O'Keeffe et al., 'Deconstructing the Crystal Structures of Metal-Organic Frameworks and Related Materials into Their Underlying Nets,' Chem. Rev. 112(2):675-702 (Feb. 8, 2012).

Oisaki et al., "A Metal-Organic Framework with Covalently Bound Organometallic Complexes," J. of the Amer. Chem. Soc., pp. 9262-9264, vol. 132, No. 27, 2010.

Park, H. et al., 'Synthesis, Structure Determination and Hydrogen Sorption Studies of New Metal-Organic Frameworks Using Triazole and Naphthalenedicarboxylic Acid,' Chem. Natur. 19:1302-1308 (2007).

Park, Jae Woo. International Search Report for PCT/US2010/039123, Korean Intellectual Property Office, dated Feb. 24, 2011.

Patteux, Claudine, International Search Report and Written Opinion, Application No. PCT/US2010/043373, dated Oct. 6, 2010.

Peng et al., 'Methane Storage in Metal-Organic Frameworks: Current Records, Surprise Findings, and Challenges', Journal of the American Chemical Society, vol. 135, No. 2, Aug. 14, 2013, pp. 11887-11894.

Peterson et al., 'Ammonia Vapor Removal by Cu3(BTC)2 and Its Characterization by MAS NMR,' J. Phys. Chem. C. 113(32):13906-13917 (2009).

Prajapati et al., "Metal-organic frameworks (MOFs) constructed from Znll/Cdll-2,2'-bipyridines and polycarboxylic acids: Synthesis, characterization and microstructural studies", Polyhedron 28 (2009) 600-608.

Queen et al., 'Site-Specific C02 Adsorption and Zero Thermal Expansion in an Anisotropic Pore Network,' J. Phys. Chem. C, 115:24915-24919 (Nov. 8, 2011).

"IUPAC Gold Book-cryptand", http://goldbook.iupac.org/C01426.html, accessed Jan. 30, 2014.

"IUPAC Gold Book-macrocycle". http://goldbook.iupac.org/M03662.html, accessed Jan. 30, 2014.

Adkins, Chinessa T. Final Office Action for U.S. Appl. No. 12/524,205 dated Sep. 27, 2012.

Adkins, Chinessa T. Nonfinal Office Action for U.S. Appl. No. 12/524,205 dated Apr. 17, 2012.

Akporiaye et al., 'Combinatorial Approach to the Hydrothermal Synthesis of Zeolites,' Angew. Chemie 37(5):609-611 (1998).

Ashton, Peter R. et al., 'Hydrogen-Bonded Complexes of Aromatic Crown Ethers with (9-Anthracenyl) methylammonium Derivatives' J. Am. Chem. Soc., 1997, 119 (44), pp. 10641-10651.

Baharlou, Simin, International Preliminary Report on Patentability for PCT/US2009/043373, The International Bureau of WIPO, dated Feb. 9, 2012.

Baharlou, Simin, International Preliminary Report on Patentability for PCT/US2011/024671, The International Bureau of WIPO, dated Aug. 23, 2012.

Bai, Lingfei, International Preliminary Report on Patentability and Written Opinion, The International Bureau of WIPO, PCT/US2012/022114 dated Jul. 23, 2013.

Barman et al., 'Incorporation of active metal sites in MOFs via in situ generated ligand deficient metal-linker complexes' Chem. Commun. 47:11882-11884 (Oct. 11, 2011).

Barman et al., "Incorporation of active metal sites in MOFs via in situ generated ligand deficient metal-linker complexes", Chem. Comm., 2011, pp. 1-3.

Becamel, Philippe, International Preliminary Report on Patentability, PCT/US2012/023516, The International Bureau of WIPO, dated Aug. 6, 2013.

Becamel, Philippe, International Preliminary Report on Patentability, PCT/US2012/059877, The International Bureau of WIPO, dated Sep. 18, 2014.

Bhakta et al., 'Metal organic frameworks as templates for nanoscale NaAlH4', Journal of American Chemical Society, vol. 131, No. 37, Sep. 23, 2009, pp. S1-S14.

Bjai, Lingfei, International Preliminary Report on Patentability and Written Opinion, PCT/US2015/021107, The International Bureau of WIPO, dated Sep. 20, 2016.

Bork, Ana-Marie., International Search Report for PCT/US2011/24671, European Patent Office, dated Nov. 30, 2011.

Britt et al., 'Ring-Opening Reactions Within Metal-Organic Frameworks,' Inorg. Chem. 49:6387-6389 (2010).

Britt et al., "Metal-Organic frameworks with high capacity and selectivity for harmful gases", PNAS, 2008, vol. 105, No. 33, pp. 11623-11627.

Burrows, Andrew D., 'Mixed-component metal-organic frameworks (MC-MOFs): enhancing functionality through solid solution formation and surface modifications', Crystengcomm, vol. 13, No. 11, Jan. 1, 2011, pp. 3623-3642.

Burrows, Andrew D., et al., "Post-Synthetic Modification of Tagged MOFs", Angewa. Chem. Int . Ed., (Oct. 20, 2008), vol. 47, pp. 8482-8486, XP008150669.

Carboni et al., "Highly porous and stable metal-organic frameworks for uranium extraction," Chemical Science, 4:2396-2402, Apr. 4, 2013.

(56) References Cited

OTHER PUBLICATIONS

Carlucci et al., 'Nanoporous three-dimensional networks topologically related to cooperite from the self-assembly of copper(I)centres and 1,2,4,5-tetracyanobenzene,' New J. Chem. 23(23):397-401 (1999).
Chambron, Jean-Claude, "Interlacing molecular threads on transition metals", Pure and Applied Chemistry, 1990, 62 (6), 1027-1034.
Che et al., "Mono- and Diprotonation of the [(n5-C5H5)Ti(W5O18)]3- and [(n5-C5Me5)Ti(W5O18)]3- Anions," Inorg. Chem. 1992, 31, 2920-2928.
Chen et al. "Photoluminescent Metal-Organic Polymer Constructed from Trimetallic Clusters and Mixed Carboxylates", Inorg. Chem. 2003, 42, 944-946.
Chen et al., 'Noncovalently Netted, Photoconductive Sheets with Extremely High Carrier Mobility and Conduction Anisotropy from Triphenylene-Fused Meetal Trigon Conjugates,' In. J. Am. Chem. Soc. 131:7287-7297 (2009).
Chen, Binling, et. al., "Zeolitic imidazolate framework materials: recent progress in synthesis and applications", Journal of Materials Chemistry A: Materials for Energy and Sustainability, GB, (Jul. 17, 2014), vol. 2, No. 40, doi:10.1039/C4TA02984D, ISSN 2050-7488, pp. 16811-16831, XP055337959.
Choi et al., 'Reversible Interpenetration in a Metal-Organic Framework Triggered by Ligand Removal and Addition,' Angew. Chem. Int. Ed. 51:8791-8795 (2012).
Chun et al., 'Concomitant Formation of N-Heterocyclic Carbene-Copper Comlexies within a Supramolecular Network in the Self-Assembly of lmmidzolium Dicarboxylate with Metal Ions,' Inorganic Chemistry, Jul. 20, 2009, pp. 6353-6355, vol. 48, No. 14.
Chun et al., 'Cu2O: A versatile Reagent for Base-Free Direct Synthesis of NHC-Copper Complexes and Decoration of 3D-MOF with Coordinatively Unsaturated NHC-Copper Species,' Organometallics, Mar. 16, 2010, pp. 1518-1521, vol. 29, No. 7.
Cordero Garcia, Marcela M. Nonfinal Office Action for U.S. Appl. No. 12/680,141 dated Nov. 2, 2012.
Corma et al., 'A large-cavity zeolite with wide pore windows and potential as an oil refining catalyst,' Nature, vol. 418, pp. 514-517 (Aug. 2002).
Corma et al., "From MOFs to zeolites: zirconium sites for epoxide rearrangement," New J. of Chem. 37:3496-3502, Aug. 2, 2013.
Coskun et al., 'Metal-Organic Frameworks Incorporating Copper-Complexed Rotaxanes,' Angew. Chem. Int. Ed., 51:2160-2163 (2012).
Costa ("Chemical Modification of a Bridging Ligand Inside a Metal-Organic Framework while Maintaining the 3D Structure" Eur J. Inorg. Chem (2008) 10, 1551-1554).
Costa et al., 'Chemical Modification of a Bridging Ligand Inside a Metal-Organic Framework while Maintaining the 3D Structure,' Eur J. Inorg. Chem. 10:1539-1545 (2008).
Cote et al., 'Porous, Crystalline, Covalent Organic Frameworks,' Science 310:1166-1170 (2005).
Cote et al., 'Reticular Synthesis of Microporous and Mesoporous 2D Covalent Organic Frameworks,' J. Am. Chem. Soc. 129:12914-12915 (2007).
Crees et al., 'Synthesis of a Zinc(II) Imidazolium Dicarboxylate Logand Metal-Organic Framework (MOF): a Potential Precursor to MOF-Tethered N-Heterocyclic Carbene Compounds,' Inorganic Chemistry, Jan. 19, 2010, vol. 49, No. 4, pp. 1712-1719.
Cui et al., 'In Situ Hydrothermal Growth of Metal-Organic Framework 199 Films on Stainless Steel Fibers for Solid-Phase Microextraction of Gaseous Benzene Homologues,' Anal. Chem. 81(23):9771-9777 (2009).
Day et al., "A New Structure Type in Polyoxoanion Chemistry: Synthesis and Structure of the V5O143-Anion", J. Am. Chem. Soc. 1989, 111, 4518-4519.
Day et al., "Synthesis and Characterization of a Soluble Oxide Inclusion Complex, [CH3CNC(V12O324-)]", J. Am. Chem. Soc. 1989, 111, 5959-5961.
Demessence, A et al., 'Strong C02 Bnding in a Water-Stable, Triazolate-Bridged Metal-Organic Framework Functionalized with Ethylenediamine,' J. Am. Chem. Soc. 131:8784-8786 (2009).
Demir et al., 'Role of Copper Species in the Oxidative Dimerization of Arylboronic Acids: Synthesis of Symmetrical Biaryls,' Journal of Organic Chemistry 68(26):10130-10134 (2003).
Deng et al., 'Large-Pore Apertures in a Series of Metal-Organic Frameworks,' Science 336:1018-1023 (May 25, 2012).
Deng, H. et al., "Large-Pore Apertures in a Series of Metal-Organic Frameworks," Science, vol. 336, No. 6084, May 12, 2012, pp. 1018-1023.
Deska, Malgorzata, "Donor-acceptor rotaxanes with tetracationic cyclophane ring", ARKIVOC, 2013, i, 185-242.
Deska, Malgorzata, "Rotaxanes and pseudorotaxanes with threads containing viologen units", ARKIVOC, 2013, i, 66-100.
Dhakshinamoorthy et al., "Metal-organic frameworks as heterogeneous catalysts for oxidation reactions", Catal. Sci. Technol., Apr. 28, 2011, 1, 856-867.
Dietzel, Pascal D. C., et. al., "Application of metal-organic frameworks with coordinatively unsaturated metal sites in storage and separation of methane and carbon dioxide", Journal of Materials Chemistry, (Aug. 21, 2009), vol. 19, No. 39, doi:10.1039/b911242a, ISSN 0959-9428, pp. 7362-7370, XP055197279.
Ren Shi-Bin et al, "The variety of conformational isomerism of a flexible organic linker induced by the position and amounts of aromatic carboxylic groups", Polyhedron, (Jun. 4, 2014), vol. 83, doi:10.1016/J.POLY.2014.05.069, ISSN 0277-5387, pp. 130-136, XP029080831.
Rinkel, Bert. Extended European Search Report for European Patent Application EP08713961 dated Jan. 2, 2012.
Rouseau-Jager, Nadia, International Search Report and Written Opinion, PCT/US2011/024671, European Patent Office, dated Dec. 13, 2011.
Seo et al., 'A homochiral metal-organic porous material for enantioselective separation and catalysis,' Nature 404:982-986 (2000).
Shi-Jie et al., "Synthesis and Structural Characterization of a New 3D Lead Coordination Polymer with a Tetrazole-1-acetate Ligand", Chinese J. Struct. Chem., vol. 30, No. 7, 2011, pp. 1049-1053.
Sigma-Aldrich, Basolite C300 (MOF-199), catalog No. 688614; http://www.sigmaaldrich.com/catalog/ProductDetail.do?D7=0&N5=SEARCH.sub.—CONCAT.sub.-PNO%7CBRAND.sub.-KEY&N4=688614% 7CALDRICH&N25=0&QS=ON&F=SpEC- , obtained online in 2014.
Sigma-Aldrich, Basolite C300 (MOF-199), catalog No. 688614; Copyright 2014.
Sines, Brian J. Nonfinal Office Action for U.S. Appl. No. 13/142,564 dated Jul. 9, 2012.
Song et al., 'A Multiunit Catalyst with Synergistic Stability and Reactivity: A PolyoxometalateMetal Organic Framework for Aerobic Decontamination,' J. Am. Chem. Soc. 133(42):16839-16846 (Sep. 13, 2011).
Song et al., 'Hydrothermal Synthesis and Structural Characterization of Three-dimensional Metal-organic Framework [Zn3(C2H2N3)2(C7H5O2)4],' Chem. Res. Chinese Universities 25(1):1-4 (2009).
Szeto et al., "A Thermally Stable Pt/Y-Based Metal-Organic Framework: Exploring the Accessibility of the Metal Centers with Spectroscopic Methods Using H2O, CH3OH, and CH3CN as Probes", J. Phys. Chem. B, 2006, 110, 21509-21520.
Szeto et al., "Characterization of a New Porous Pt-Containing Metal-Organic Framework Containing Potentially Catalytically Active Sites: Local Electronic Structure at the Metal Centers", Chem. Mater., 2007, 19, 211-220.
Tanabe et al., 'Systematic Functionalization of a Metal-Organic Framework via a Postsynthetic Modification Approach,' J. Am. Chem. Soc. 130(26):8508-8517 (2008).
Tilford et al., 'Facile Synthesis of a Highly Crystalline, Covalently Porous Boronate Network,' 18(22):5296-5301 (Oct. 11, 2006).
Tranchemontagne et al., 'Hydrogen Storage in New Metal-Organic Frameworks,' J. Phys. Chem. C 116 (24):13143-13151 (May 24, 2012).
Vitillo et al., 'Role of Exposed Metal Sites in Hydrogen Storage in MOFs,' J. Am. Chem. Soc. 130(26):8386-8396 (2008).
Vodak et al., 'One-Step Synthesis and Structure of an Oligo(spiro-orthocarbonate),' J. Am. Chem. Soc.124 (18):4942-4943 (2002).

(56) References Cited

OTHER PUBLICATIONS

Wang, Yiting, First Office Action, Chinese Patent Application No. CN201080036940.6, dated Dec. 4, 2013.

Wang, Zhenqiang, et al., 'Postsynthetic Covalent Modification of a Neutral Metal—Organic Framework', J. Am. Chem. Soc., (2007), vol. 129, No. 41, pp. 12368-12369.

Wardencki et al. Green Chemistry—Current and Future Issues. Review. Polish Journal of Environmental Studies. 2005. vol. 14, No. 4, pp. 389-395.

Whitfield et al. Metal-organic frameworks based on iron oxide octahedral chains connected by benzendicarboxylate dianions. Solid State Sciences, 2005. vol. 7, pp. 1096-1103.

Wu et al., 'Structural Study of New Hydrocarbon Nano-Crystals by Energy-Filtered Electron Diffraction,' Ultramicroscopy 98:145-150 (2004).

Yaghi et al., "Directed Transformation of Molecules to Solids: Synthesis of a Microporous Sulfide from Molecular Germanium Sulfide Cages", J. Am. Chem. Soc. 1994, 116, 807-808.

Yaghi et al., "Preparation of Single Crystals of Coordination Solids in Silica Gels: Synthesis and Structure of CuII (1,4-C4H4N2)(C4O4)(OH2)4", Journal of Solid State Chemistry, 117, 256-260 (1995).

Yaghi et al., "Rhenium-Selenium-Chlorine Solid Phases: Cluster Excision and Core Substitution Reactions of Molecular Species", Inorg. Chem. 1992, 31, 4778-4784.

Yang et al. 'Two Novel Triazole-Based Metal-Organic Frameworks Consolidated by a Flexible Dicarboxylate Co-ligand: Hydrothermal Synthesis, Crystal Structure, and Luminescence Properties,' Australian Journal of Chemistry 61 (10):813-820 (2008).

Yang et al., 'CH4 storage and C02 capture in highly porous zirconium oxide based metal-organic frameworks,' Chem. Commun., 48:9831-9833, Aug. 15, 2012.

Yang et al., 'Four Novel Three-Dimensional Triazole-Based Zinc(II) Metal-Organic Frameworks Controlled by the Spacers of Dicarboxylate Ligands: Hydrothermal Synthesis, Crystal Structure, and Luminescence Properties,' Crystal Growth Design 7(10):2009-2015 (2007).

Young, Jung Doo, International Search Report & Written Opinion, Korean Application No. PCT/US2011/044625, dated Feb. 24, 2012.

Young, Jung Doo, International Search Report and Written Opinion, Application No. PCT/US2012/022114, dated Aug. 22, 2012.

Young, Jung Doo. International Search Report and Written Opinion for PCT/US2011/053423 dated Jul. 23, 2012.

Young, Lee W., International Search Report and Written Opinion, Application No. PCT/US08/70149, dated Jan. 12, 2009.

Zhang et al., 'Crystal engineering of binary metal imidazolate and triazolate frameworks,' Chem. Comm. 1689-1699 (2006).

Zhang et al., 'Syntheses, Structures, and Porous/Luminescent Properties of Silver 3-Alkyl-1,2,4-Triazolate Frameworks with Rare 3-Connected Topologies,' Crystal Growth and Design 11:796-802 (2011).

Zhang, J. et al., 'Exceptional Framework Flexibility and Sorption Behavior of a Multifunctional Porous Cuprous Triazolate Framework,' J. Am. Chem. Soc. 130:6010-6017 (2008).

Zhao, Office Action in Chinese Patent Application No. 20088031572, dated Aug. 5, 2011.

Zhao Wei, First Office Action for Chinese Application No. 200880003157.2, The State Intellectual Property Office of the People's Republic of China dated Aug 5, 2011.

Zhou et al., 'Introduction to Metal-Organic Frameworks,' Chemical Reviews 112:673-674 (Jan. 26, 2012).

Zhou, X et al., 'Hydrothermal Syntheses and Structures of Three Novel Coordination Polymers Assembled from 1,2,3-Triazolate Ligands,' CrystEngComm. 11:1964-1970 (2009).

Zhu, A. et al., 'Isomeric Zinc(II) Triazolate Frameworks with 3-Connected Networks: Syntheses, Structures, and Sorption Properties,' Inorg. Chem. 48:3882-3889 (2009).

Zou et al., "Novel Eclipsed 2D Cadmium(II) Coordination Polymers with Open-Channel Structure Constructed from Terephthalate and 3-(2-Pyridyl)pyrazole: Crystal Structures, Emission Properties, and Inclusion of Guest Molecules", Inorg. Chem. 2004, 43, 5382-5386.

* cited by examiner demetalated COF-505

BZ

COVALENT ORGANIC FRAMEWORKS WITH A WOVEN STRUCTURE

CROSS REFERENCE TO RELATED APPLICATIONS

This application is a U.S. National Stage Application filed under 35 U.S.C. § 371 and claims priority from International Application No. PCT/US2016/063774, filed Nov. 25, 2016, which application claims priority under 35 U.S.C. § 119 from Provisional Application Ser. No. 62/260,458, filed Nov. 27, 2015, the disclosures of which are incorporated herein by reference.

STATEMENT REGARDING FEDERAL SPONSORED RESEARCH

This invention was supported by the U.S. Government under Grant No. DE-SC0001015 awarded by the U.S. Department of Energy and Grant No. HDTRA1-12-1-0053 awarded by the U.S. Department of Defense. The U.S. Government has certain rights in the invention.

TECHNICAL FIELD

The disclosure provides for covalent organic frameworks (COFs) that constructed from weaving a plurality of long organic threads together. In particular, the disclosure provides for the construction of woven COFS, where long organic strands are connected together in a woven pattern using organic ligands/complexes that when orientated in certain geometries are capable of reversibly binding metal ions.

BACKGROUND

Making fabric by weaving is known as one of the oldest and most enduring methods. Nevertheless, such an important design concept still needs to be emulated in extended chemical structures. Linking molecules into weaving structures would be of a great help to create materials with exceptional mechanical properties and dynamics. COFs are structures created with organic building blocks that are linked together. They are appealing because their low density and high porosity has many promising applications, such as for storing gas or for optoelectronics, but previously, synthesized COFs have been too rigid. Creating more flexible COFs, those that resemble woven fabrics, has been challenging on a molecular level.

SUMMARY

Provided herein are three-dimensional covalent organic frameworks (such as COF-505) that are comprised of helical organic threads that have been woven together at regular or periodic intervals. In a particular embodiment, the helical organic treads can be woven together by forming an imine bond between aldehyde functionalized copper(I)-bisphenanthroline tetrafluoroborate, $Cu(PDB)_2(BF_4)$, and benzidine (BZ). The copper centers are topologically independent of the weaving within the COF structure and only serve as a weaving agent for bringing the threads into a woven pattern rather than the more commonly observed parallel arrangement. The copper(I) ions can be reversibly removed and added without loss of the COF structure, for which a ten-fold increase in elasticity accompanies its demetallation. The threads in COF-505 have many degrees of freedom for enormous deviations to take place between them, throughout the material, without undoing the weaving of the overall structure.

In a particular embodiment, the disclosure provides for a woven covalent organic framework that comprises a plurality of long organic threads that are mutually interlaced at regular intervals so as to form points-of-registry, wherein the long organic threads comprise organic linking ligands that have been covalently bound together and wherein at least some portion of the organic linking ligands further comprise heteroatoms and/or functional groups capable of coordinating a metal, metal ion or metal containing complex, and wherein the points-of-registry may be metalated to comprise coordinated metals, metal ions, or metal containing complexes, or may be de-metalated. In another embodiment, for a woven covalent organic framework disclosed herein, the points-of-registry comprise the general structure of Formula V:

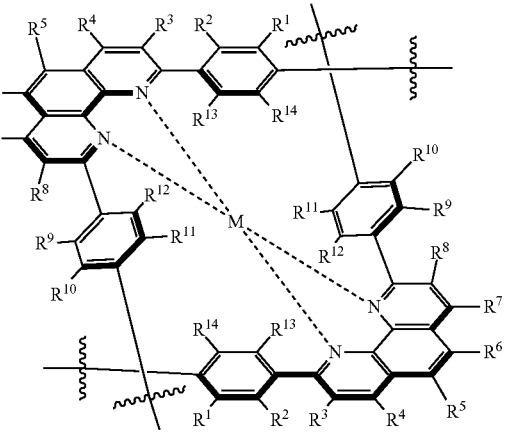

Formula V wherein, M is a metal ion, metal, or a metal complex that is bound to nitrogen atoms, or alternatively M is absent; $R^1$-$R^{10}$ are each independently selected from H, FG, ($C_1$-$C_{12}$)alkyl, substituted ($C_1$-$C_{12}$)alkyl, ($C_2$-$C_{12}$)alkenyl, substituted ($C_2$-$C_{12}$)alkenyl, ($C_2$-$C_{12}$)alkynyl, substituted ($C_2$-$C_{12}$)alkynyl, hetero-($C_1$-$C_{12}$)alkyl, substituted hetero-($C_1$-$C_{12}$)alkyl, hetero-($C_2$-$C_{12}$)alkenyl, substituted hetero-($C_2$-$C_{12}$)alkenyl, hetero-($C_2$-$C_{12}$)alkynyl, substituted hetero-($C_2$-$C_{12}$)alkynyl, ($C_3$-$C_{12}$)cycloalkyl, substituted ($C_3$-$C_{12}$)cycloalkyl, aryl, substituted aryl, heterocycle, substituted heterocycle, —C($R^{50}$)$_3$, —CH($R^{50}$)$_2$, —CH$_2$$R^5$, —C($R^{51}$)$_3$, —CH($R^{51}$), —CH$_2$$R^{51}$, —OC($R^{50}$)$_3$, —OCH($R^{50}$)$_2$, —OCH$_2$R, OC($R^{51}$)$_3$, —OCH($R^{51}$), —OCH$_2$$R^{51}$, or $R^1$-$R^{10}$ when adjacent can form a substituted or unsubstituted ring selected from the group comprising cycloalkyl, aryl and heterocycle; $R^{11}$-$R^{14}$ are each independently selected from H, D, FG, ($C_1$-$C_3$)alkyl, substituted ($C_1$-$C_3$)alkyl, hetero-($C_1$-$C_3$)alkyl, or substituted hetero-($C_1$-$C_3$)alkyl. $R^{50}$ is selected from the group comprising FG, ($C_1$-$C_{12}$)alkyl, ($C_1$-$C_{12}$)substituted alkyl, ($C_1$-$C_{12}$)alkenyl, substituted ($C_1$-$C_{12}$)alkenyl, ($C_1$-$C_{12}$)alkynyl, substituted ($C_1$-$C_{12}$)alkynyl, hetero-($C_1$-$C_{12}$)alkyl, substituted hetero-($C_1$-$C_{12}$)alkyl, hetero-($C_1$-$C_{12}$)alkenyl, substituted hetero-($C_1$-$C_{12}$)alkenyl, hetero-($C_1$-$C_{12}$)alkynyl, substituted hetero-($C_1$-$C_{12}$)alkynyl; $R^{51}$ is one or more substituted or unsubstituted rings selected from the group consisting of cycloalkyl, aryl, and heterocycle; and FG is selected from the group consisting of halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitrites, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_3$, $Ge(SH)_3$, $AsO_3H$, $AsO_3H$, $P(SH)_3$, $As(SH)_3$, $SO_3H$, $Si(OH)_3$, $Ge(OH)_3$, $Sn(OH)_3$, $Si(SH)_3$, $Ge(SH)_3$, $Sn(SH)_3$, $AsO_3H$, $AsO_3H$, $P(SH)_3$, and $As(SH)_3$. In a further embodiment, M is a metal or a metal ion selected from the group consisting of $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, Cr, $Mo^{6+}$, $Mo^{5+}$, $Mo^{4+}$, $Mo^{3+}$, $Mo^{2+}$, $Mo^+$, Mo, $W^{6+}$, $W^{5+}$, $W^{4+}$, $W^{3+}$, $W^{2+}$, $W^+$, W, $Mn^{7+}$, $Mn^{6+}$, $Mn^5$, $Mn^{4+}$, $Mn^{3+}$, $Mn^{2+}$, $Mn^+$, $Re^{7+}$, $Re^{6+}$, $Re^5$, $Re^{4+}$, $Re^{3+}$, $Re^{2+}$, $Re^+$, Re, $Fe^{6+}$, $Fe^{4+}$, $Fe^{3+}$, $Fe^{2+}$, $Fe^+$, Fe, $Ru^{8+}$, $Ru^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, Os, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^+$, $Ir^{4+}$, $Ir^{3+}$, $Ir^{2+}$, $Ir^+$, Ir, $Ni^{3+}$, $Ni^{2+}$, $Ni^+$, Ni, $Pd^{6+}$, $Pd^{4+}$, $Pd^{2+}$, $Pd^+$, Pd, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, Zn, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, Ge, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{5+}$, $Te^{4+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, $La^{3+}$, $La^{2+}$, and $La^+$. In a particular embodiment, M is a tetrahedrally coordinating metal ion or an octahedrally coordinating metal ion. In another embodiment, for a woven organic framework disclosed herein, the points-of-registry comprise the general structure of Formula V(a):

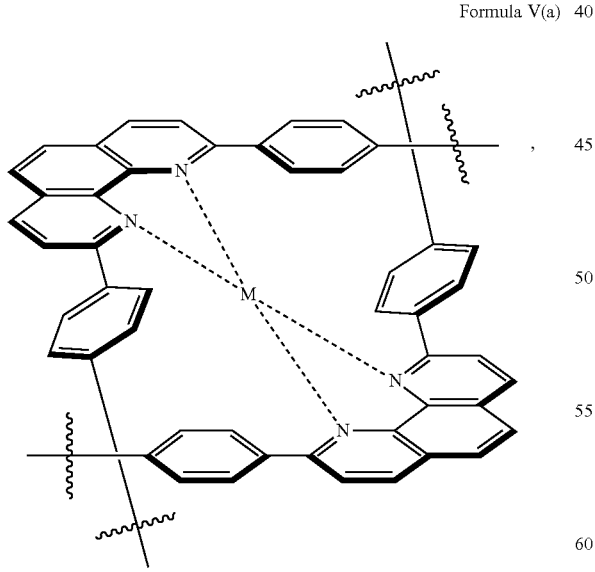

Formula V(a)

wherein, M is a tetrahedrally coordinating metal ion. In a further embodiment, M is $Cu^+$.

In another embodiment, for a woven covalent organic framework disclosed herein the points-of-registry comprise the general structure of Formula V(b):

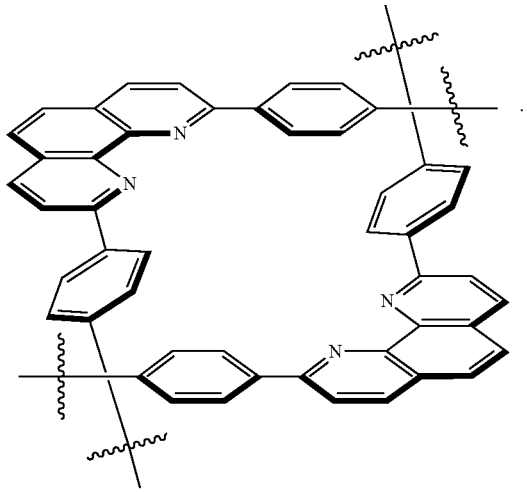

Formula V(b)

In a certain embodiment, the disclosure also provides for a woven covalent organic framework disclosed herein which comprises long organic helical threads comprising covalently bound alternating linking ligands, wherein the alternating linking ligands comprise linking ligands having the structure of Formula I:

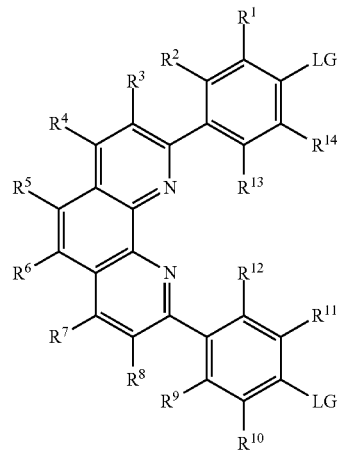

Formula I covalently bound to linking ligands comprising the structure of Formula II, III, or IV:

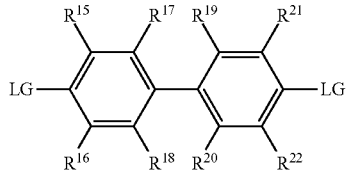

Formula II

-continued

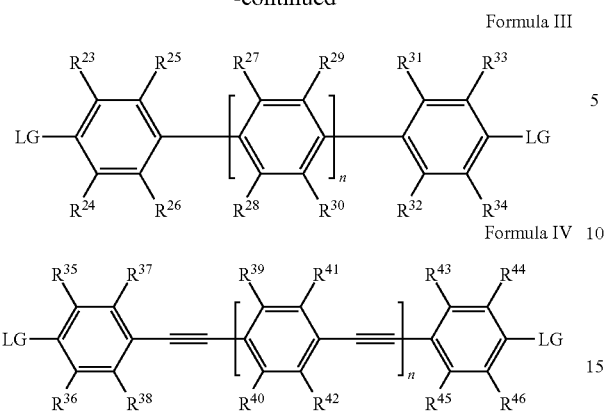

Formula III

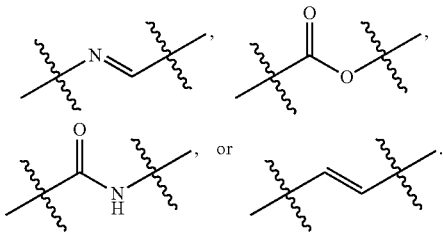

wherein, $R^1$-$R^{10}$, and $R^{15}$-$R^{46}$ are each independently selected from H, FG, $(C_1$-$C_{12})$alkyl, substituted $(C_1$-$C_{12})$ alkyl, $(C_2$-$C_{12})$alkenyl, substituted $(C_2$-$C_{12})$alkenyl, $(C_2$-$C_{12})$alkynyl, substituted $(C_2$-$C_{12})$alkynyl, hetero-$(C_1$-$C_{12})$ alkyl, substituted hetero-$(C_1$-$C_{12})$alkyl, hetero-$(C_2$-$C_{12})$ alkenyl, substituted hetero-$(C_2$-$C_{12})$alkenyl, hetero-$(C_2$-$C_{12})$ alkynyl, substituted hetero-$(C_2$-$C_{12})$alkynyl, $(C_3$-$C_{12})$ cycloalkyl, substituted $(C_3$-$C_{12})$cycloalkyl, aryl, substituted aryl, heterocycle, substituted heterocycle, —C($R^{50}$)$_3$, —CH($R^{50}$)$_2$, —CH$_2R^{50}$, —C($R^{51}$)$_3$, —CH($R^{51}$), —CH$_2R^{51}$, —OC($R^{50}$)$_3$, —OCH($R^{50}$)$_2$, —OCH$_2R^{50}$, —OC($R^{51}$)$_3$, —OCH($R^{51}$), —OCH$_2R^{51}$, or $R^1$-$R^{10}$ when adjacent can form a substituted or unsubstituted ring selected from the group comprising cycloalkyl, aryl and heterocycle; $R^{11}$-$R^{14}$ are each independently selected from H, D, FG, $(C_1$-$C_3)$ alkyl, substituted $(C_1$-$C_3)$alkyl, hetero-$(C_1$-$C_3)$alkyl, or substituted hetero-$(C_1$-$C_3)$alkyl; $R^{50}$ is selected from the group comprising FG, $(C_1$-$C_{12})$alkyl, $(C_1$-$C_{12})$substituted alkyl, $(C_1$-$C_{12})$alkenyl, substituted $(C_1$-$C_{12})$alkenyl, $(C_1$-$C_{12})$alkynyl, substituted $(C_1$-$C_{12})$alkynyl, hetero-$(C_1$-$C_{12})$alkyl, substituted hetero-$(C_1$-$C_{12})$alkyl, hetero-$(C_1$-$C_{12})$alkenyl, substituted hetero-$(C_1$-$C_{12})$alkenyl, hetero-$(C_1$-$C_{12})$alkynyl, substituted hetero-$(C_1$-$C_{12})$alkynyl; $R^{51}$ is one or more substituted or unsubstituted rings selected from the group consisting of cycloalkyl, aryl, and heterocycle; and FG is selected from the group consisting of halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitrites, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, Si(OH)$_3$, Ge(OH)$_3$, Sn(OH)$_3$, Si(SH)$_3$, Ge(SH)$_3$, AsO$_3$H, AsO$_3$H, P(SH)$_3$, As(SH)$_3$, SO$_3$H, Si(OH)$_3$, Ge(OH)$_3$, Sn(OH)$_3$, Si(SH)$_3$, Ge(SH)$_3$, Sn(SH)$_3$, AsO$_3$H, AsO$_3$H, P(SH)$_3$, and As(SH)$_3$; LG is each independently selected from the group consisting of boronic acid, nitriles, aldehyde, amine, halide, hydroxyl, acyl halide, carboxylic acid, and acetic anhydride; and n is an integer from 1 to 10, wherein the LG groups of Formula I and the LG groups of Formula II, III, or IV are covalently bound together. In a further embodiment, the covalent bond formed between the LG groups of Formula I and the LG groups of Formula II, III, or IV, has the structure of:

In a particular embodiment, the disclosure further provides for a woven covalent organic framework disclosed herein which comprises covalently bound alternating linking ligands, wherein the alternating linking ligands comprise linking ligands having the structure of Formula I(b):

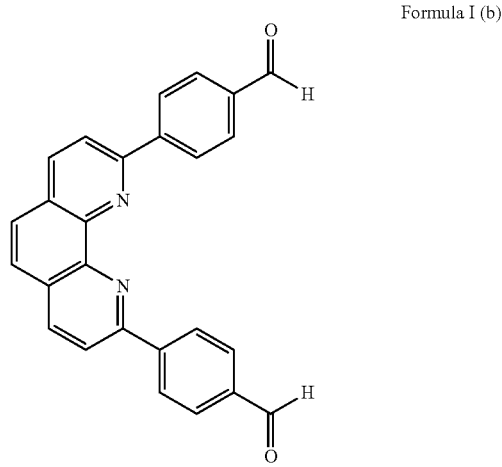 [SMILES: O=Cc1ccc(-c2ccc3ccc4ccc(-c5ccc(C=O)cc5)nc4c3n2)cc1]

Formula I(b)

covalently bound to linking ligands comprising the structure of Formula II(b), III(b), or IV(b):

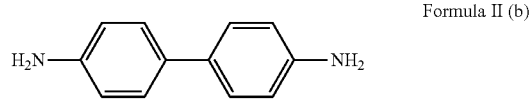

Formula II(b)

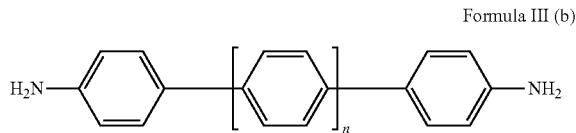

Formula III(b)

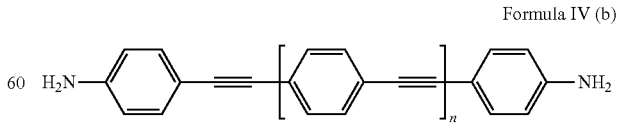

Formula IV(b)

wherein, n is an integer from 1 to 10; and wherein the linking ligands having the structure of Formula I(b) are covalently bound to the linking ligands having the structure of Formula II(b), III(b) or IV(b) via an imine bond:

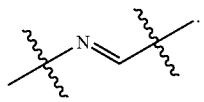 [SMILES: */C=N/*]

In another embodiment, the disclosure provides for a woven covalent organic framework that is de-metalated. In an alternate embodiment, the disclosure also provides for a woven framework that is metalated or re-metalated. In a further embodiment, a woven covalent organic framework disclosed herein exhibits a fold increase in elasticity when the woven covalent organic framework is de-metalated, where in the fold increase in elasticity between a metalated vs. de-metalated woven covalent organic framework is at least 2, 3, 4, 5, 6, 7, 8, 9, 10, or a range between any two numbers of the foregoing. In a further embodiment, the disclosure provides for a woven organic framework that has the structure and properties of COF-505. In another embodiment, the disclosure provides for a woven covalent organic framework where the points of registry comprise tetrahedrally coordinated metal ions. In a further embodiment, a woven covalent organic framework which has points of registry comprising tetrahedrally coordinated metal ions has a topology selected from pnf, qtz, and sod. In an alternate embodiment, the disclosure provides for a woven covalent organic framework where the points of registry comprise octahedrally coordinated metal ions. In a further embodiment, a woven covalent organic framework which has points of registry comprising octahedrally coordinated metal ions has a topology selected from kgm and pcu.

In a particular, embodiment the disclosure provides for a resilient material which comprising a woven covalent organic framework disclosed herein. Examples of such resilient materials include, but are not limited to shape-memory material development or biomedical applications.

The details of one or more embodiments of the disclosure are set forth in the accompanying drawings and the description below. Other features, objects, and advantages will be apparent from the description and drawings, and from the claims.

DETAILED DESCRIPTION

Figure 1A:
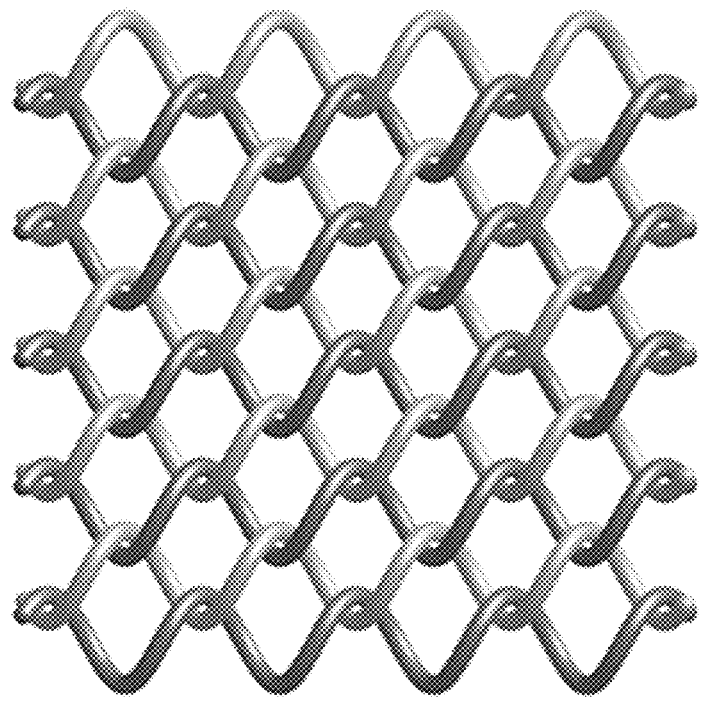
FIG. 1A-D provides an embodiment of weaving and entanglement of structures described herein. Illustrations of weaving of threads in (A) two-dimensions, and (B) three-dimensions, compared with (C) entanglements of sheets, (D) three-dimensional arrangements. Expanded views of interlocking of rings (insets).

As used herein and in the appended claims, the singular forms "a," "an," and "the" include plural referents unless the context clearly dictates otherwise. Thus, for example, reference to "a linking moiety" includes a plurality of such linking moieties and reference to "the core" includes reference to one or more cores and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which may be used in connection with the description herein. However, with respect to any similar or identical terms found in the incorporated publications and those expressly defined in this application, then the terms' definition as expressly put forth in this application shall control in all respects.

A bond indicated by a straight line and a dashed line indicates a bond that may be a single covalent bond or alternatively a double covalent bond. But in the case where an atom's maximum valence would be exceeded by forming a double covalent bond, then the bond would be a single covalent bond.

The term "alkyl", refers to an organic group that is comprised of carbon and hydrogen atoms that contain single covalent bonds between carbons. Typically, an "alkyl" as used in this disclosure, refers to an organic group that contains 1 to 30 carbon atoms, unless stated otherwise. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkenyl", refers to an organic group that is comprised of carbon and hydrogen atoms that contains at least one double covalent bond between two carbons. Typically, an "alkenyl" as used in this disclosure, refers to organic group that contains 2 to 30 carbon atoms, unless stated otherwise. While a $C_2$-alkenyl can form a double bond, an alkenyl group of three or more carbons can contain more than one double bond. In certain instances the alkenyl group will be conjugated, in other cases an alkenyl group will not be conjugated, and yet other cases the alkenyl group may have stretches of conjugation and stretches of nonconjugation. Additionally, if there is more than 2 carbon, the carbon atoms may be connected in a linear manner, or alternatively if there are more than 3 carbon atoms then the carbons may also be linked in a branched fashion so that the parent chain contains one or more secondary, tertiary, or quaternary carbons. An alkenyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains 2 to 30 carbon atoms, unless stated otherwise. While a $C_2$-alkynyl can form a triple bond, an alkynyl group of three or more carbons can contain more than one triple bond. Where if there are more than 2 carbon atoms, the carbons may be connected in a linear manner, or alternatively if there are more than 4 carbon atoms then the carbon atoms may also be linked in a branched fashion so that the parent chain contains one or more secondary, tertiary, or quaternary carbons. An alkynyl may be substituted or unsubstituted, unless stated otherwise.

The term "aryl", as used in this disclosure, refers to a conjugated planar ring system with delocalized pi electron clouds that contain only carbon as ring atoms. An "aryl" for the purposes of this disclosure encompass from 1 to 12 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

As used herein, a "core" refers to a repeating unit or units found in a network. A network can comprise a homogenous repeating core, a heterogeneous repeating core or a combination of homogenous and heterogeneous cores.

The term "cycloalkyl", as used in this disclosure, refers to an alkyl that contains at least 3 carbon atoms but no more than 12 carbon atoms connected so that it forms a ring. A "cycloalkyl" for the purposes of this disclosure encompass from 1 to 12 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "cycloalkenyl", as used in this disclosure, refers to an alkene that contains at least 4 carbon atoms but no more than 12 carbon atoms connected so that it forms a ring. A "cycloalkenyl" for the purposes of this disclosure encompass from 1 to 12 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

The term "framework" as used herein, refers to an ordered structure comprised of secondary building units (SBUs) that can be linked together in defined, repeated and controllable manner, such that the resulting structure is characterized as being porous, periodic and crystalline. Typically, "frameworks" are two dimensional (2D) or three dimensional (3D) structures. Examples of "frameworks" include, but are not limited to, "metal-organic frameworks" or "MOFs", "zeolitic imidazolate frameworks" or "ZIFs", or "covalent organic frameworks" or "COFs". While MOFs and ZIFs comprise SBUs of metals or metal ions linked together by forming covalent bonds with linking clusters on organic linking ligands, COFs are comprised of SBUs of organic linking ligands that are linked together by forming covalent bonds via linking clusters. "Frameworks", as used herein, are highly ordered and extended structures that are not based upon a centrally coordinated ion, but involve many repeated secondary building units (SBUs) linked together. Accordingly, "frameworks" are orders of magnitude much larger than coordination complexes, and have different structural and chemical properties due to the framework's open and ordered structure.

The term "functional group" or "FG" refers to specific groups of atoms within molecules that are responsible for the characteristic chemical reactions of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Examples of FGs that can be used in this disclosure, include, but are not limited to, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_3$, $Ge(SH)_3$, $AsO_3H$, $AsO_3H$, $P(SH)_3$, $As(SH)_3$, $SO_3H$, $Si(OH)_3$, $Ge(OH)_3$, $Sn(OH)_3$, $Si(SH)_4$, $Ge(SH)_4$, $Sn(SH)_3$, $AsO_3H$, $AsO_3H$, $P(SH)_3$, and $As(SH)_3$.

The term "heterocycle", as used in this disclosure, refers to ring structures that contain at least 1 non-carbon ring atom, and typically comprise from 3 to 12 ring atoms. A "heterocycle" for the purposes of this disclosure encompass from 1 to 12 heterocycle rings wherein when the heterocycle is greater than 1 ring the heterocycle rings are joined so that they are linked, fused, or a combination thereof. A heterocycle may be a hetero-aryl or nonaromatic, or in the case of more than one heterocycle ring, one or more rings may be nonaromatic, one or more rings may be hetero-aryls, or a combination thereof. A heterocycle may be substituted or unsubstituted, or in the case of more than one heterocycle ring one or more rings may be unsubstituted, one or more rings may be substituted, or a combination thereof. Typically, the non-carbon ring atom is N, O, S, Si, Al, B, or P. In case where there is more than one non-carbon ring atom, these non-carbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "hetero-aryl" used alone or as a suffix or prefix, refers to a heterocycle or heterocyclyl having aromatic character. Examples of heteroaryls include, but are not limited to, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O.

The term "linking group" or "LG" as used herein refers to functional groups that are found on organic linking ligands (typically, two or more LG groups) that are used to form covalent bonds with one or more additional organic linking ligands. While organic linking ligands may all comprise the same LG groups, e.g., boronic acid, typically, the FG groups differ either on the same organic linking ligand or between organic linking ligands. The linking ligands are chosen to have high selectivity's for each other under defined reaction conditions (e.g., imine bond formation, Fischer esterification, Michael additions, Schotten-Baumann Reaction, etc.). Examples of LG, include functional groups like boronic acid, nitriles, aldehydes, amines, halides, hydroxyls, acyl halides, carboxylic acids, and acetic anhydrides.

The term "linking cluster" refers to one or more atoms capable of forming an association, e.g. covalent bond, polar covalent bond, ionic bond, and Van Der Waal interactions, with one or more atoms of another linking moiety or core. For example, a linking cluster can comprise NN(H)N, N(H)NN, $CO_2H$, $CS_2H$, $NO_2$, $SO_3H$, $Si(OH)_3$, $Ge(OH)_3$, $Sn(OH)_3$, $Si(SH)_3$, $Ge(SH)_3$, $Sn(SH)_3$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, wherein R is an alkyl group having from 1 to 5 carbon atoms, or an aryl group comprising 1 to 2 phenyl rings and $CH(SH)_2$, $C(SH)_3$, $CH(NH_2)_2$, $C(NH_2)_3$, $CH(OH)_2$, $C(OH)_3$, $CH(CN)_2$, and $C(CN)_3$.

The term "long organic threads" as used herein refers to extended structures that comprise organic linking ligands that have been covalently linked together to form a long organic strand, where the long organic strand comprises at least 20, 30, 40, 50, or 100 organic linking ligands. Furthermore, a "long organ threads" as used herein do not refer to naturally occurring polymers like polynucleotides, polypeptides, and the like.

The term "long helical organic threads" refers to long organic threads as defined above that further have a helical twist.

A "metal" refers to a solid material that is typically hard, shiny, malleable, fusible, and ductile, with good electrical and thermal conductivity. "Metals" used herein refer to metals selected from alkali metals, alkaline earth metals, lanthanides, actinides, transition metals, and post transition metals.

A "metal ion" refers to an ion of a metal. Metal ions are generally Lewis Acids and can form coordination complexes. Typically, the metal ions used for forming a coordination complex in a framework are ions of transition metals.

The term "mixed ring system" refers to optionally substituted ring structures that contain at least two rings, and wherein the rings are joined together by linking, fusing, or a combination thereof. A mixed ring system comprises a combination of different ring types, including cycloalkyl, cycloalkenyl, aryl, and heterocycle.

The term "organic linking ligand" or "linking ligand" as used herein refers to an organic molecule that comprises a hydrocarbon and/or heterocycle parent chain that comprise at least two or more functional groups wherein these functional groups are used to form covalent bonds with other organic linking ligands. In the structure presented herein, these functional groups have been designated as LG ('linking groups') to distinguish these groups from other substitutions.

The term "substituted" with respect to hydrocarbons, heterocycles, and the like, refers to structures wherein hydrogen atoms have been replaced by a substituent.

The term "substituent" refers to an atom or group of atoms substituted in place of a hydrogen atom. For purposes of this disclosure, a substituent would include deuterium atoms.

The term "unsubstituted" with respect to hydrocarbons, heterocycles, and the like, refers to structures wherein the parent chain comprises no substituents.

The term "weaving agent" as used refers to an agent that can be used for bringing organic threads into a woven pattern so that the organic threads are mutually interlaced at regular or periodic intervals. In a particular embodiment, a "weaving agent" comprises metals, metal ions, or metal containing complexes that interact (e.g., form coordinate bonds) with two or more organic threads at certain geometries (e.g., tetrahedral, octahedral, paddle-wheel, etc.) so that the threads are assembled into a three-dimensional (3D) covalent organic framework. In a further embodiment, the organic threads have points-of-registry at the location of the weaving agents. While not being bound by any particular theory, the metal, metal ions, or metal containing complexes are postulated as seeking parts of the organic threads that are equally spaced from each other in order to bring together two organic threads in an up and down pattern like a weave. Examples of metals, metal ions that can be used as a weaving agent, include, but are not limited to, $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Sc^{2+}$, $Sc^+$, $Y^{3+}$, $Y^{2+}$, $Y^+$, $Ti^{4+}$, $Ti^{3+}$, $Ti^{2+}$, $Zr^{4+}$, $Zr^{3+}$, $Zr^{2+}$, $Hf^{4+}$, $Hf^{3+}$, $V^{5+}$, $V^{4+}$, $V^{3+}$, $V^{2+}$, $Nb^{5+}$, $Nb^{4+}$, $Nb^{3+}$, $Nb^{2+}$, $Ta^{5+}$, $Ta^{4+}$, $Ta^{3+}$, $Ta^{2+}$, $Cr^{6+}$, $Cr^{5+}$, $Cr^{4+}$, $Cr^{3+}$, $Cr^{2+}$, $Cr^+$, $Cr$, $Mo^{6+}$, $Mo^{5+}$, $Mo^{4+}$, $Mo^{3+}$, $Mo^{2+}$, $Mo^+$, $Mo$, $W^{6+}$, $W^{5+}$, $W^{4+}$, $W^{3+}$, $W^{2+}$, $W^+$, $W$, $Mn^{7+}$, $Mn^{6+}$, $Mn^{5+}$, $Mn^{4+}$, $Mn^{3+}$, $Mn^{2+}$, $Mn^+$, $Re^{7+}$, $Re^{6+}$, $Re^{5+}$, $Re^{4+}$, $Re^{3+}$, $Re^{2+}$, $Re^+$, $Re$, $Fe^{6+}$, $Fe^{4+}$, $Fe^{3+}$, $Fe^{2+}$, $Fe^+$, $Fe$, $Ru^{8+}$, $R^{7+}$, $Ru^{6+}$, $Ru^{4+}$, $Ru^{3+}$, $Ru^{2+}$, $Os^{8+}$, $Os^{7+}$, $Os^{6+}$, $Os^{5+}$, $Os^{4+}$, $Os^{3+}$, $Os^{2+}$, $Os^+$, $Os$, $Co^{5+}$, $Co^{4+}$, $Co^{3+}$, $Co^{2+}$, $Co^+$, $Rh^{6+}$, $Rh^{5+}$, $Rh^{4+}$, $Rh^{3+}$, $Rh^{2+}$, $Rh^+$, $Ir^{6+}$, $Ir^{5+}$, $Ir^{4+}$, $Ir^{3+}$, $Ir^{2+}$, $Ir^+$, $Ir$, $Ni^{3+}$, $Ni^{2+}$, $Ni^+$, $Ni$, $Pd^{6+}$, $Pd^{4+}$, $Pd^{2+}$, $Pd^+$, $Pd$, $Pt^{6+}$, $Pt^{5+}$, $Pt^{4+}$, $Pt^{3+}$, $Pt^{2+}$, $Pt^+$, $Cu^{4+}$, $Cu^{3+}$, $Cu^{2+}$, $Cu^+$, $Ag^{3+}$, $Ag^{2+}$, $Ag^+$, $Au^{5+}$, $Au^{4+}$, $Au^{3+}$, $Au^{2+}$, $Au^+$, $Zn^{2+}$, $Zn^+$, $Zn$, $Cd^{2+}$, $Cd^+$, $Hg^{4+}$, $Hg^{2+}$, $Hg^+$, $B^{3+}$, $B^{2+}$, $B^+$, $Al^{3+}$, $Al^{2+}$, $Al^+$, $Ga^{3+}$, $Ga^{2+}$, $Ga^+$, $In^{3+}$, $In^{2+}$, $In^{1+}$, $Tl^{3+}$, $Tl^+$, $Si^{4+}$, $Si^{3+}$, $Si^{2+}$, $Si^+$, $Ge^{4+}$, $Ge^{3+}$, $Ge^{2+}$, $Ge^+$, $Ge$, $Sn^{4+}$, $Sn^{2+}$, $Pb^{4+}$, $Pb^{2+}$, $As^{5+}$, $As^{3+}$, $As^{2+}$, $As^+$, $Sb^{5+}$, $Sb^{3+}$, $Bi^{5+}$, $Bi^{3+}$, $Te^{6+}$, $Te^{6+}$, $Te^{5+}$, $Te^{2+}$, $La^{3+}$, $La^{2+}$, $Ce^{4+}$, $Ce^{3+}$, $Ce^{2+}$, $Pr^{4+}$, $Pr^{3+}$, $Pr^{2+}$, $Nd^{3+}$, $Nd^{2+}$, $Sm^{3+}$, $Sm^{2+}$, $Eu^{3+}$, $Eu^{2+}$, $Gd^{3+}$, $Gd^{2+}$, $Gd^+$, $Tb^{4+}$, $Tb^{3+}$, $Tb^{2+}$, $Tb^+$, $Db^{3+}$, $Db^{2+}$, $Ho^{3+}$, $Er^{3+}$, $Tm^{4+}$, $Tm^{3+}$, $Tm^{2+}$, $Yb^{3+}$, $Yb^{2+}$, $Lu^{3+}$, $La^{3+}$, $La^{2+}$, and $La^+$. Typically, the weaving agent is a tetrahedrally or octahedrally coordinating metal ion. In a particular embodiment, the weaving agent is $Cu^+$.

Weaving, the mutual interlacing of long threads is one of the oldest and most enduring methods of making fabric, but this important design concept is yet to be emulated in extended chemical structures. Learning how to link molecular building units by strong bonds through reticular synthesis into weaving forms would be a boon to making materials with exceptional mechanical properties and dynamics. In order to successfully design weaving of chains into two- and three-dimensional (2D and 3D) chemical structures (see FIGS. 1A and B), long threads of covalently linked molecules should be able to cross at regular intervals. It would also be desirable if such crossings serve as points-of-registry so that the threads can have many degrees of freedom to move away and back to such points without collapsing the overall structure.

Figure 1B:
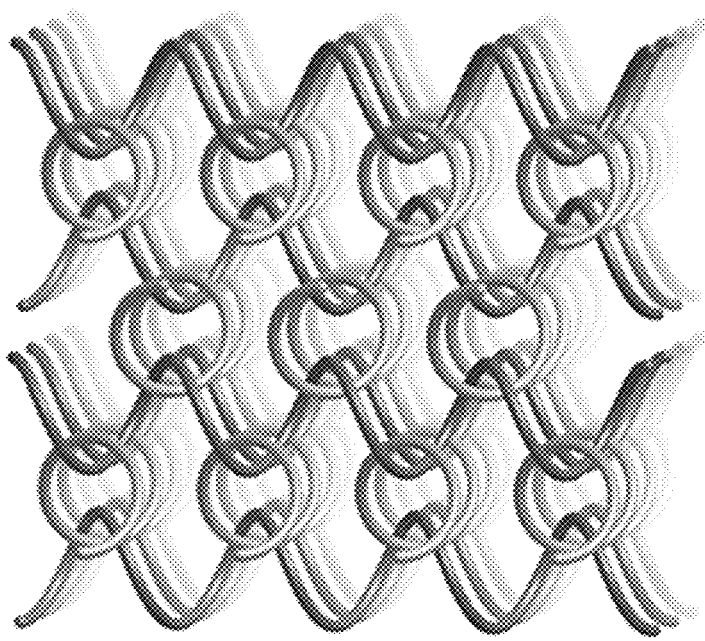
Figure 1C:
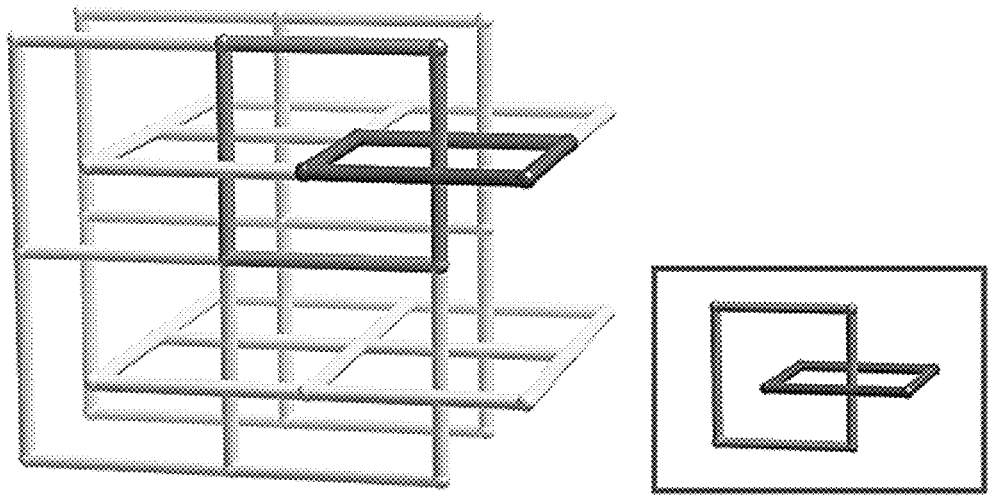
Figure 1D:
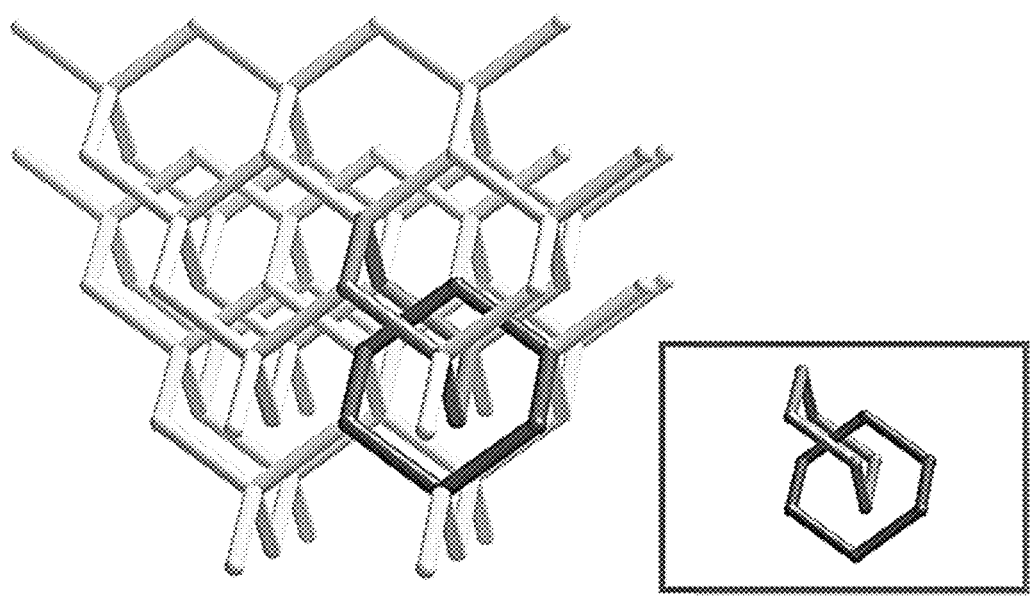

Provided herein is a general strategy and its implementation for the designed synthesis of a woven material (e.g., covalent organic framework-505, COF-505). For example, the disclosure teaches the synthesis of COF-505 which comprises helical organic threads interlacing to make a weaved crystal structure with the basic topology of FIG. 1B. It was further shown herein, that this woven material (e.g., COF-505) exhibited heretofore elasticity that was has not been previously seen in non-woven materials. Although terms such as interweaving, polycatenated and interpenetrating have been used to describe interlocking of 2D and 3D extended objects (see FIGS. 1C and D), most commonly found in MOFs, the "weaving" as used herein is used to describe exclusively the interlacing of units to make 2D and 3D structures (see FIGS. 1A and B). "Weaving" therefore differs from the commonly observed interpenetrating and polycatenated frameworks as the latter is topologically interlocking (i.e. interlocking rings, FIGS. 1C and D, insets). The woven constructs described herein have many more degrees of freedom than interweaving, polycatenated and interpenetrating materials. Thus, the woven constructs provided herein are capable of enormous spatial deviations by each of the threads that can take place independently and still preserve the underlying topology. Such freedom allows for reversible control over the mechanical properties of materials.

In a particular embodiment, the disclosure provides for a woven covalent organic framework (COF) that comprises a plurality of long organic helical threads that mutual interlace with each other together at regular or periodic intervals.

In a further embodiment, the disclosure provides for a long organic helical thread comprising linking ligands comprising the structure of Formula I:

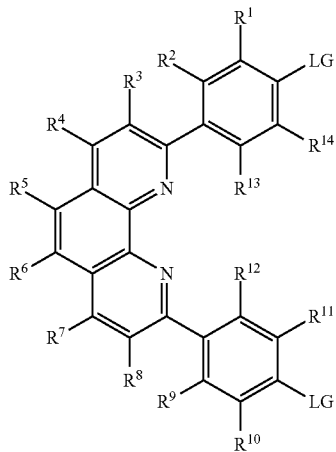

Formula I that are covalently linked with linking ligands comprising the structure of Formula II, III, or IV via a covalent bond formed between the LG groups of Formula I and the LG groups of Formula II, III, or IV:

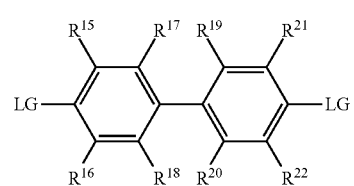

Formula II

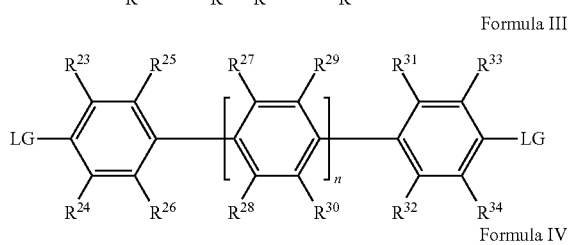

Formula III

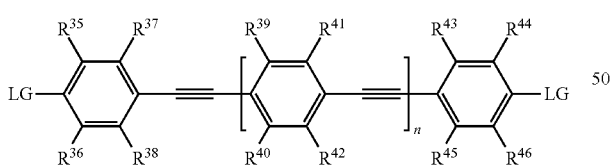

Formula IV wherein, $R^1$-$R^{10}$, and $R^{15}$-$R^{46}$ are each independently selected from H, FG, $(C_1$-$C_{12})$alkyl, substituted $(C_1$-$C_{12})$alkyl, $(C_2$-$C_{12})$alkenyl, substituted $(C_2$-$C_{12})$alkenyl, $(C_2$-$C_{12})$alkynyl, substituted $(C_2$-$C_{12})$alkynyl, hetero-$(C_1$-$C_{12})$alkyl, substituted hetero-$(C_1$-$C_{12})$alkyl, hetero-$(C_2$-$C_{12})$alkenyl, substituted hetero-$(C_2$-$C_{12})$alkenyl, hetero-$(C_2$-$C_{12})$alkynyl, substituted hetero-$(C_2$-$C_{12})$alkynyl, $(C_3$-$C_{12})$cycloalkyl, substituted $(C_3$-$C_{12})$cycloalkyl, aryl, substituted aryl, heterocycle, substituted heterocycle, —$C(R^{50})_3$, —$CH(R^{50})_2$, —$CH_2R^{50}$, —$C(R^{51})_3$, —$CH(R^{51})$, —$CH_2R^{51}$, —$OC(R^{50})_3$, —$OCH(R^{50})_2$, —$OCH_2R^{50}$, —$OC(R^{51})_3$, —$OCH(R^{51})$, —$OCH_2R^{51}$, or $R^1$-$R^{10}$ when adjacent can form a substituted or unsubstituted ring selected from the group comprising cycloalkyl, aryl and heterocycle;

$R^{11}$-$R^{14}$ are each independently selected from H, D, FG, $(C_1$-$C_3)$alkyl, substituted $(C_1$-$C_3)$alkyl, hetero-$(C_1$-$C_3)$alkyl, or substituted hetero-$(C_1$-$C_3)$alkyl.

$R^{50}$ is selected from the group comprising FG, $(C_1$-$C_{12})$ alkyl, $(C_1$-$C_{12})$substituted alkyl, $(C_1$-$C_{12})$alkenyl, substituted $(C_1$-$C_{12})$alkenyl, $(C_1$-$C_{12})$alkynyl, substituted $(C_1$-$C_{12})$alkynyl, hetero-$(C_1$-$C_{12})$alkyl, substituted hetero-$(C_1$-$C_{12})$alkyl, hetero-$(C_1$-$C_{12})$alkenyl, substituted hetero-$(C_1$-$C_{12})$alkenyl, hetero-$(C_1$-$C_{12})$alkynyl, substituted hetero-$(C_1$-$C_{12})$alkynyl;

$R^{51}$ is one or more substituted or unsubstituted rings selected from the group consisting of cycloalkyl, aryl, and heterocycle; and FG is selected from the group consisting of halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitrites, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_3$, $Ge(SH)_3$, $AsO_3H$, $AsO_3H$, $P(SH)_3$, $As(SH)_3$, $SO_3H$, $Si(OH)_3$, $Ge(OH)_3$, $Sn(OH)_3$, $Si(SH)_3$, $Ge(SH)_3$, $Sn(SH)_3$, $AsO_3H$, $AsO_3H$, $P(SH)_3$, and $As(SH)_3$; and n is an integer from 1 to 10. Examples of bonds that can result from reacting the FG groups of Formula I with the FG groups of Formula II, III, or IV include, but are not limited to:

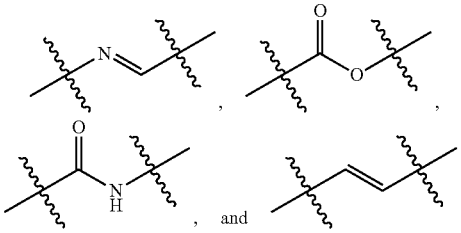

In yet a further embodiment, the disclosure provides for a long organic helical thread comprising linking ligands that have the structure of Formula I(a):

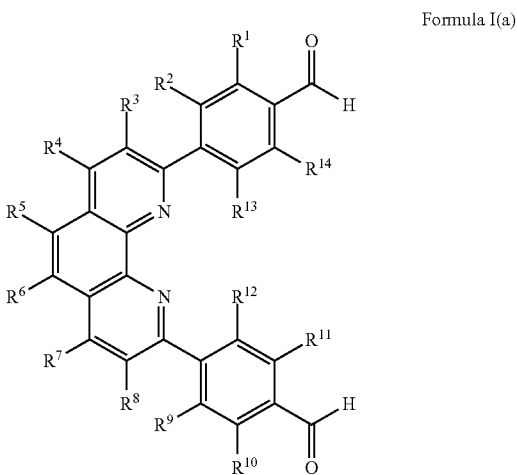

Formula I(a)

that are covalently linked with linking ligands comprising the structure of Formula II(a), III(a), or IV(a):

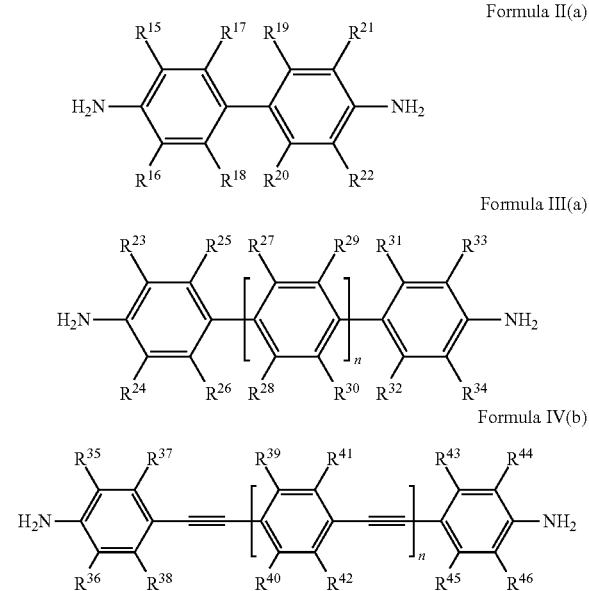

Formula II(a)

Formula III(a)

Formula IV(b)

wherein, $R^1$-$R^{10}$, and $R^{15}$-$R^{46}$ are each independently selected from H, FG, $(C_1$-$C_{12})$alkyl, substituted $(C_1$-$C_{12})$alkyl, $(C_2$-$C_{12})$alkenyl, substituted $(C_2$-$C_{12})$alkenyl, $(C_2$-$C_{12})$alkynyl, substituted $(C_2$-$C_{12})$alkynyl, hetero-$(C_1$-$C_{12})$alkyl, substituted hetero-$(C_1$-$C_{12})$alkyl, hetero-$(C_2$-$C_{12})$alkenyl, substituted hetero-$(C_2$-$C_{12})$alkenyl, hetero-$(C_2$-$C_{12})$alkynyl, substituted hetero-$(C_2$-$C_{12})$alkynyl, $(C_3$-$C_{12})$cycloalkyl, substituted $(C_3$-$C_{12})$cycloalkyl, aryl, substituted aryl, heterocycle, substituted heterocycle, —OC($R^{50}$)$_3$, —CH($R^{50}$)$_2$, —CH$_2$$R^{50}$, —C($R^{51}$)$_3$, —CH($R^{51}$), —CH$_2$$R^{51}$, —OC($R^{50}$)$_3$, —OCH($R^{50}$)$_2$, —OCH$_2$$R^{50}$, —OC($R^{51}$)$_3$, —OCH($R^{51}$), —OCH$_2$$R^{51}$, or $R^1$-$R^{10}$ when adjacent can form a substituted or unsubstituted ring selected from the group comprising cycloalkyl, aryl and heterocycle;

$R^{11}$-$R^{14}$ are each independently selected from H, D, FG, $(C_1$-$C_3)$alkyl, substituted $(C_1$-$C_3)$alkyl, hetero-$(C_1$-$C_3)$alkyl, or substituted hetero-$(C_1$-$C_3)$alkyl.

$R^{50}$ is selected from the group comprising FG, $(C_1$-$C_{12})$alkyl, $(C_1$-$C_{12})$substituted alkyl, $(C_1$-$C_{12})$alkenyl, substituted $(C_1$-$C_{12})$alkenyl, $(C_1$-$C_{12})$alkynyl, substituted $(C_1$-$C_{12})$alkynyl, hetero-$(C_1$-$C_{12})$alkyl, substituted hetero-$(C_1$-$C_{12})$alkyl, hetero-$(C_1$-$C_{12})$alkenyl, substituted hetero-$(C_1$-$C_{12})$alkenyl, hetero-$(C_1$-$C_{12})$alkynyl, substituted hetero-$(C_1$-$C_{12})$alkynyl;

$R^{51}$ is one or more substituted or unsubstituted rings selected from the group consisting of cycloalkyl, aryl, and heterocycle; and FG is selected from the group consisting of halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitrites, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, Si(OH)$_3$, Ge(OH)$_3$, Sn(OH)$_3$, Si(SH)$_3$, Ge(SH)$_3$, AsO$_3$H, AsO$_3$H, P(SH)$_3$, As(SH)$_3$, SO$_3$H, Si(OH)$_3$, Ge(OH)$_3$, Sn(OH)$_3$, Si(SH)$_3$, Ge(SH)$_3$, Sn(SH)$_3$, AsO$_3$H, AsO$_3$H, P(SH)$_3$, and As(SH)$_3$;

LG is each independently selected from the group consisting of boronic acid, nitriles, aldehyde, amine, halide, hydroxyl, acyl halide, carboxylic acid, and acetic anhydride; and n is an integer from 1 to 10. Examples of the foregoing, include the structure of:

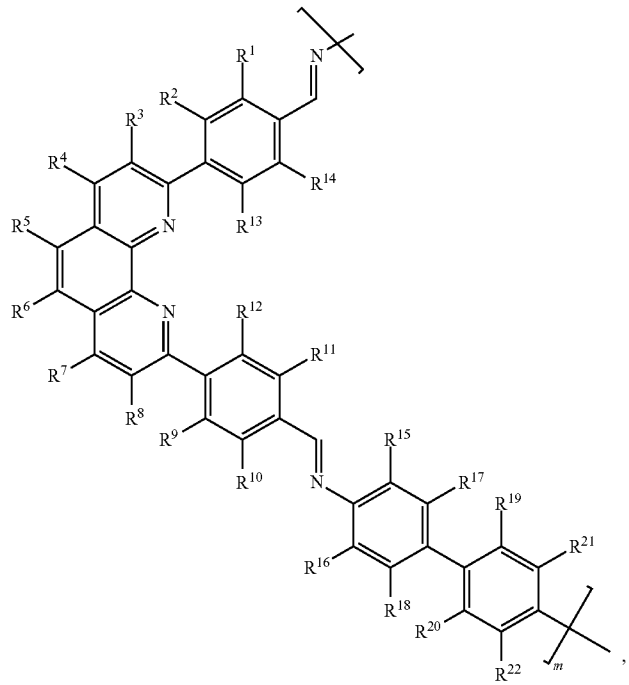

-continued
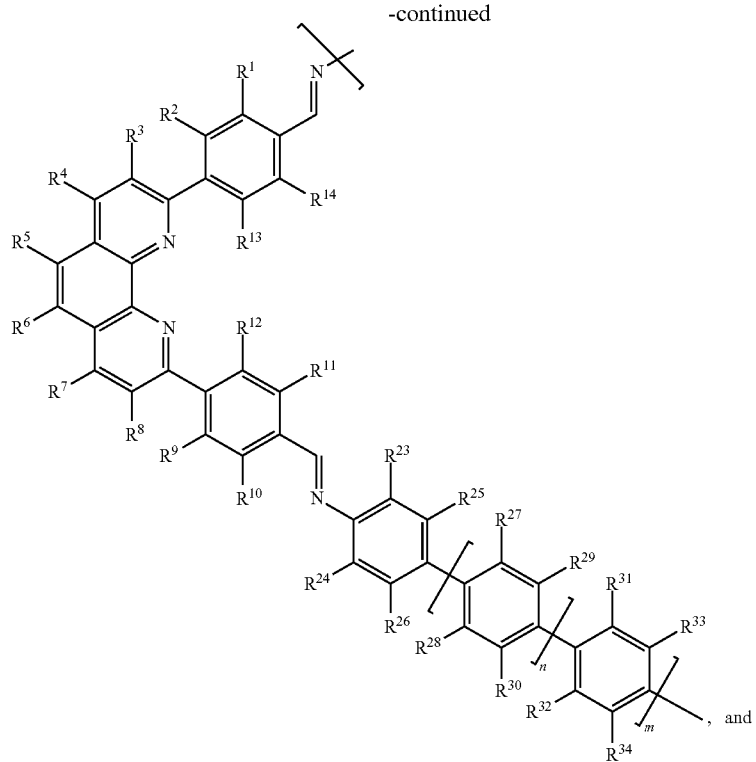
, and
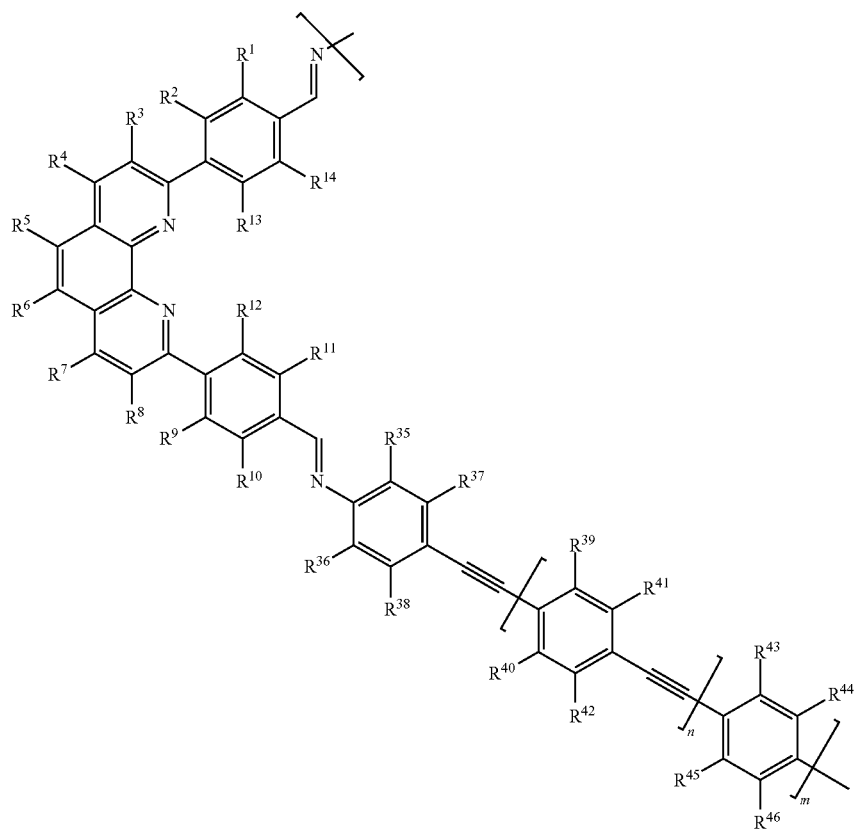
where m is an integer greater than 10, 20, 50 or 100.

In yet a further embodiment, the disclosure provides for a long organic helical thread that comprises linking ligands comprising the structure of Formula I(b):

Formula I(b)

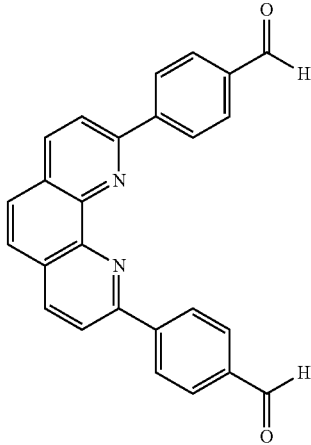

that are covalently linked with linking ligands comprising the structure of Formula II(b), III(b), or IV(b):

Formula II(b)

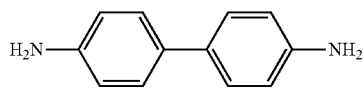

Formula III(b)

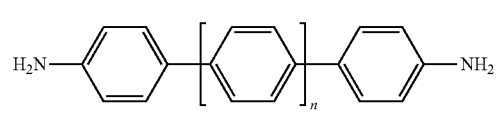

Formula IV(b)

wherein,
n is an integer from 1 to 10.

In a further embodiment, the disclosure provides for a woven covalent organic framework (COF) that comprises a plurality of long organic helical threads that mutual interlace with each other at regular intervals to form points-of-registry, wherein the points-of-registry comprise the general structure of Formula V:

Formula V

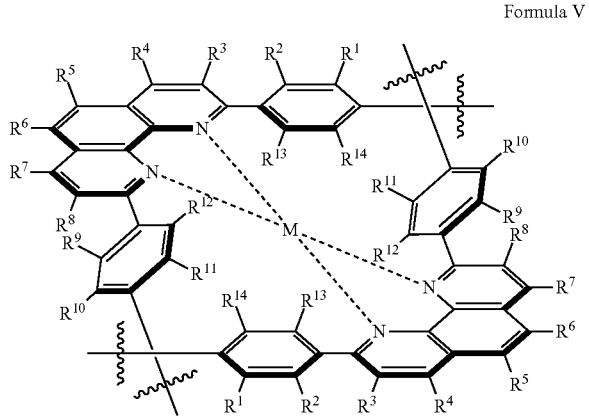

wherein,

M is a metal ion, metal, or a metal complex that is bound to nitrogen atoms, or alternatively M is absent;

$R^1$-$R^{10}$ are each independently selected from H, FG, $(C_1$-$C_{12})$alkyl, substituted $(C_1$-$C_{12})$alkyl, $(C_2$-$C_{12})$alkenyl, substituted $(C_2$-$C_{12})$alkenyl, $(C_2$-$C_{12})$alkynyl, substituted $(C_2$-$C_{12})$alkynyl, hetero-$(C_1$-$C_{12})$alkyl, substituted hetero-$(C_1$-$C_{12})$alkyl, hetero-$(C_2$-$C_{12})$alkenyl, substituted hetero-$(C_2$-$C_{12})$alkenyl, hetero-$(C_2$-$C_{12})$alkynyl, substituted hetero-$(C_2$-$C_{12})$alkynyl, $(C_3$-$C_{12})$cycloalkyl, substituted $(C_3$-$C_{12})$cycloalkyl, aryl, substituted aryl, heterocycle, substituted heterocycle, —C$(R^{50})_3$, —CH$(R^{50})_2$, —CH$_2R^{50}$, —C$(R^{51})_3$, —CH$(R^{51})$, —CH$_2R^{51}$, —OC$(R^{50})_3$, —OCH$(R^{50})_2$, —OCH$_2R^{50}$, —OC$(R^{51})_3$, —OCH$(R^{51})$, —OCH$_2R^{51}$, or $R^1$-$R^{10}$ when adjacent can form a substituted or unsubstituted ring selected from the group comprising cycloalkyl, aryl and heterocycle;

$R^{11}$-$R^{14}$ are each independently selected from H, D, FG, $(C_1$-$C_3)$alkyl, substituted $(C_1$-$C_3)$alkyl, hetero-$(C_1$-$C_3)$alkyl, or substituted hetero-$(C_1$-$C_3)$alkyl.

$R^{50}$ is selected from the group comprising FG, $(C_1$-$C_{12})$alkyl, $(C_1$-$C_{12})$substituted alkyl, $(C_1$-$C_{12})$alkenyl, substituted $(C_1$-$C_{12})$alkenyl, $(C_1$-$C_{12})$alkynyl, substituted $(C_1$-$C_{12})$alkynyl, hetero-$(C_1$-$C_{12})$alkyl, substituted hetero-$(C_1$-$C_{12})$alkyl, hetero-$(C_1$-$C_{12})$alkenyl, substituted hetero-$(C_1$-$C_{12})$alkenyl, hetero-$(C_1$-$C_{12})$alkynyl, substituted hetero-$(C_1$-$C_{12})$alkynyl;

$R^{51}$ is one or more substituted or unsubstituted rings selected from the group consisting of cycloalkyl, aryl, and heterocycle; and FG is selected from the group consisting of halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitrites, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, Si(OH)$_3$, Ge(OH)$_3$, Sn(OH)$_3$, Si(SH)$_3$, Ge(SH)$_3$, AsO$_3$H, AsO$_3$H, P(SH)$_3$, As(SH)$_3$, SO$_3$H, Si(OH)$_3$, Ge(OH)$_3$, Sn(OH)$_3$, Si(SH)$_3$, Ge(SH)$_3$, Sn(SH)$_3$, AsO$_3$H, AsO$_3$H, P(SH)$_3$, and As(SH)$_3$. In a further embodiment, M is a metal, metal ion or metal complex comprising a metal or metal ion selected from the group consisting of Li$^+$, Na$^+$, K$^+$, Rb$^+$, Cs$^+$, Be$^{2+}$, Mg$^{2+}$, Ca$^{2+}$, Sr$^{2+}$, Ba$^{2+}$, Sc$^{3+}$, Sc$^{2+}$, Sc$^+$, Y$^{3+}$, Y$^{2+}$, Y$^+$, Ti$^{4+}$, Ti$^{3+}$, Ti$^{2+}$, Zr$^{4+}$, Zr$^{3+}$, Zr$^{2+}$, Hf$^{4+}$, Hf$^{3+}$, V$^{5+}$, V$^{4+}$, V$^{3+}$, V$^{2+}$, Nb$^{5+}$, Nb$^{4+}$, Nb$^{3+}$, Nb$^{2+}$, Ta$^{5+}$, Ta$^{4+}$, Ta$^{3+}$, Ta$^{2+}$, Cr$^{6+}$, Cr$^{5+}$, Cr$^{4+}$, Cr$^{3+}$, Cr$^{2+}$, Cr$^+$, Cr, Mo$^{6+}$, Mo$^{5+}$, Mo$^{4+}$, Mo$^{3+}$, Mo$^{2+}$, Mo$^+$, Mo, W$^{6+}$, W$^{5+}$, W$^{4+}$, W$^{3+}$, W$^{2+}$, W$^+$, W, Mn$^{7+}$, Mn$^{6+}$, Mn$^{5+}$, Mn$^{4+}$, Mn$^{3+}$, Mn$^{2+}$, Mn$^+$, Re$^7$, Re$^{6+}$, Re$^5$, Re$^{4+}$, Re$^{3+}$, Re$^{2+}$, Re$^+$, Re, Fe$^{6+}$, Fe$^{4+}$, Fe$^{3+}$, Fe$^{2+}$, Fe$^+$, Fe, Ru$^{8+}$, Ru$^{7+}$, Ru$^{6+}$, Ru$^{4+}$, Ru$^{3+}$, Ru$^{2+}$, Os$^{8+}$, Os$^{7+}$, Os$^{6+}$, Os$^{5+}$, Os$^{4+}$, Os$^{3+}$, Os$^{2+}$, Os$^+$, Os, Co$^{5+}$, Co$^{4+}$, Co$^{3+}$, Co$^{2+}$, Co$^+$, Rh$^{6+}$, Rh$^{5+}$, Rh$^{4+}$, Rh$^{3+}$, Rh$^{2+}$, Rh$^+$, Ir$^{6+}$, Ir$^{5+}$, Ir$^{4+}$, Ir$^{3+}$, Ir$^{2+}$, Ir$^+$, Ir, Ni$^{3+}$, Ni$^{2+}$, Ni$^+$, Ni, Pd$^{6+}$, Pd$^{4+}$, Pd$^{2+}$, Pd$^+$, Pd, Pt$^{6+}$, Pt$^{5+}$, Pt$^{4+}$, Pt$^{3+}$, Pt$^{2+}$, Pt$^+$, Cu$^{4+}$, Cu$^{3+}$, Cu$^{2+}$, Cu$^+$, Ag$^{3+}$, Ag$^{2+}$, Ag$^+$, Au$^{5+}$, Au$^{4+}$, Au$^{3+}$, Au$^{2+}$, Au$^+$, Zn$^{2+}$, Zn$^+$, Zn, Cd$^{2+}$, Cd$^+$, Hg$^{4+}$, Hg$^{2+}$, Hg$^+$, B$^{3+}$, B$^{2+}$, B$^+$, Al$^{3+}$, Al$^{2+}$, Al$^+$, Ga$^{3+}$, Ga$^{2+}$, Ga$^+$, In$^{3+}$, In$^{2+}$, In$^{1+}$, Tl$^{3+}$, Tl$^+$, Si$^{4+}$, Si$^{3+}$, Si$^{2+}$, Si$^+$, Ge$^{4+}$, Ge$^{3+}$, Ge$^{2+}$, Ge$^+$, Ge, Sn$^{4+}$, Sn$^{2+}$, Pb$^{4+}$, Pb$^{2+}$, As$^{5+}$, As$^{3+}$, As$^{2+}$, As$^+$, Sb$^{5+}$, Sb$^{3+}$, Bi$^{5+}$, Bi$^{3+}$, Te$^{6+}$, Te$^{5+}$, Te$^{4+}$, Te$^{2+}$, La$^{3+}$, La$^{2+}$, Ce$^{4+}$, Ce$^{3+}$, Ce$^{2+}$, Pr$^{4+}$, Pr$^{3+}$, Pr$^{2+}$, Nd$^{3+}$, Nd$^{2+}$, Sm$^{3+}$, Sm$^{2+}$, Eu$^{3+}$, Eu$^{2+}$, Gd$^{3+}$, Gd$^{2+}$, Gd$^+$, Tb$^{4+}$, Tb$^{3+}$, Tb$^{2+}$, Tb$^+$, Db$^{3+}$, Db$^{2+}$, Ho$^{3+}$, Er$^{3+}$, Tm$^{4+}$, Tm$^{3+}$, Tm$^{2+}$, Yb$^{3+}$, Yb$^{2+}$, Lu$^{3+}$, La$^{3+}$, La$^{2+}$, and La$^+$. In a particular embodiment, M is Cu$^+$.

In a further embodiment, the disclosure provides for a woven covalent organic framework (COF) that comprises a plurality of long organic helical threads that mutual interlace with each other at regular intervals to form points-of-registry, wherein the points-of-registry comprise the general structure of Formula V(a):

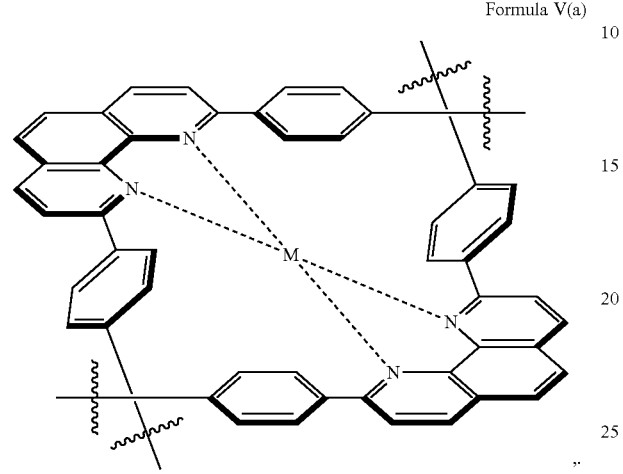

Formula V(a)

wherein,

M is a tetrahedrally coordinating metal ion.

In a further embodiment, the disclosure provides for a woven covalent organic framework (COF) that comprises a plurality of long organic helical threads that mutual interlace with each other at regular intervals to form points-of-registry, wherein the points-of-registry comprise the general structure of Formula V(b):

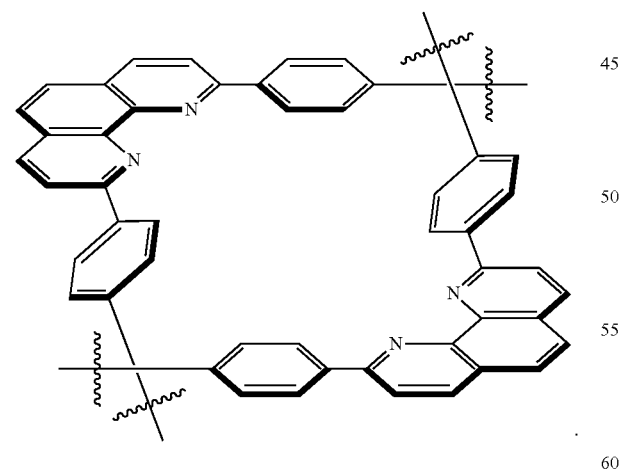

Formula V(b)

Various structures presented herein can be synthesized using methods known in the art or are commercially available. In a particular embodiment, a compound having the structure of Formula I can be made by scheme I:

SCHEME I

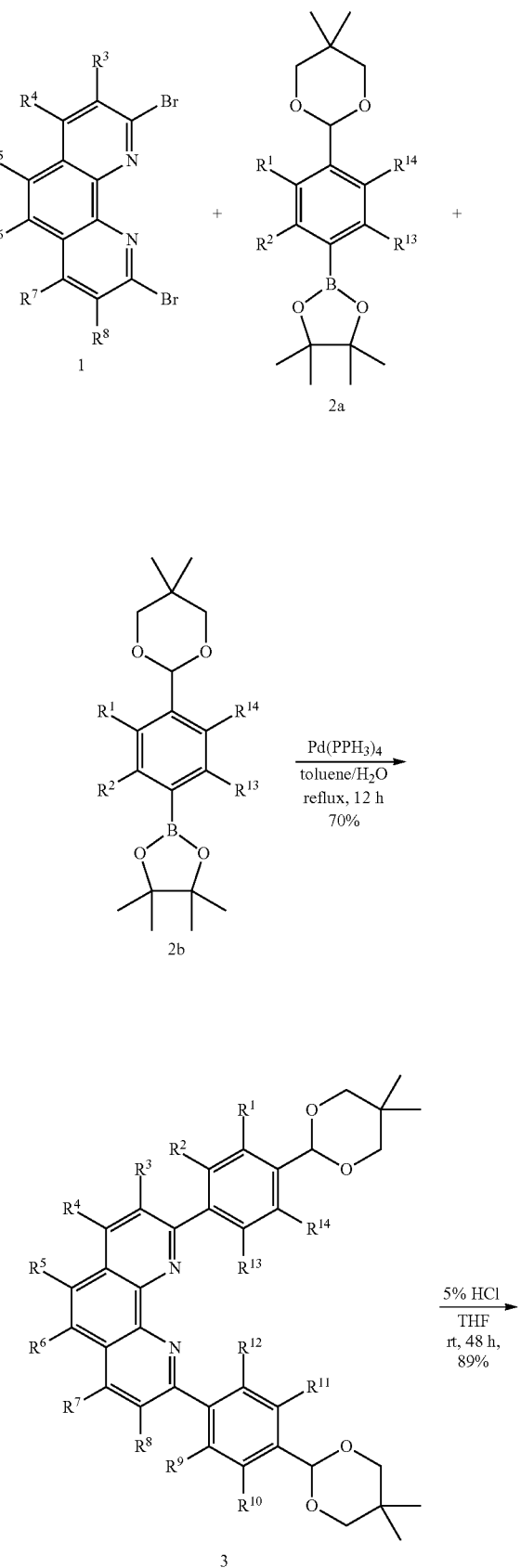

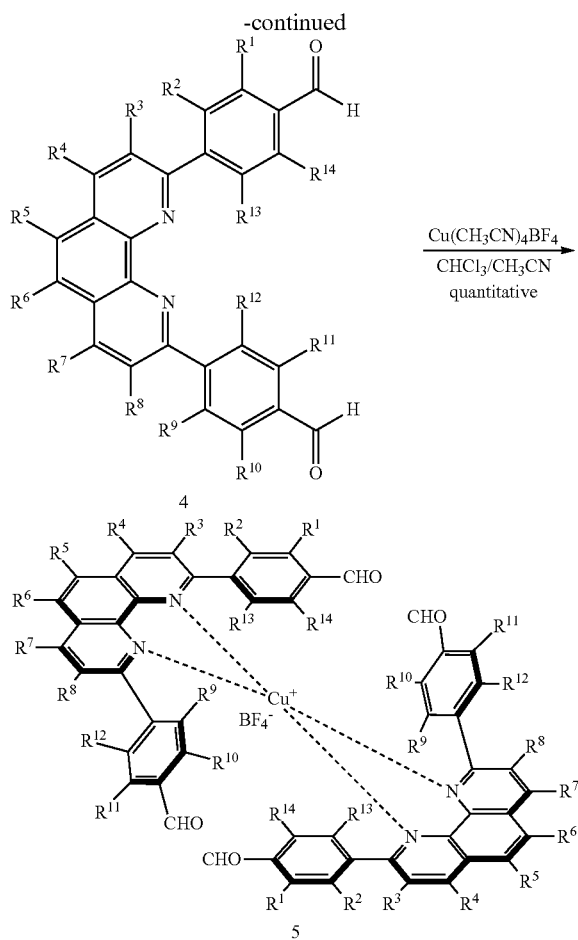

Figure 5:
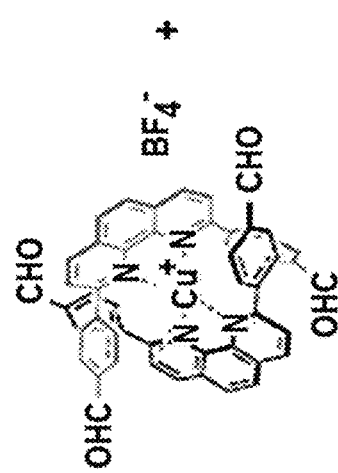
FIG. 5 presents the synthesis of the molecular analogue of COF-505, $Cu(PBM)_2$.
Figure 5:
Figure 5:
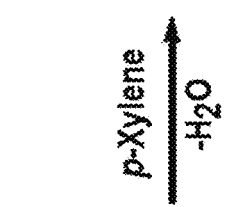
Figure 5:
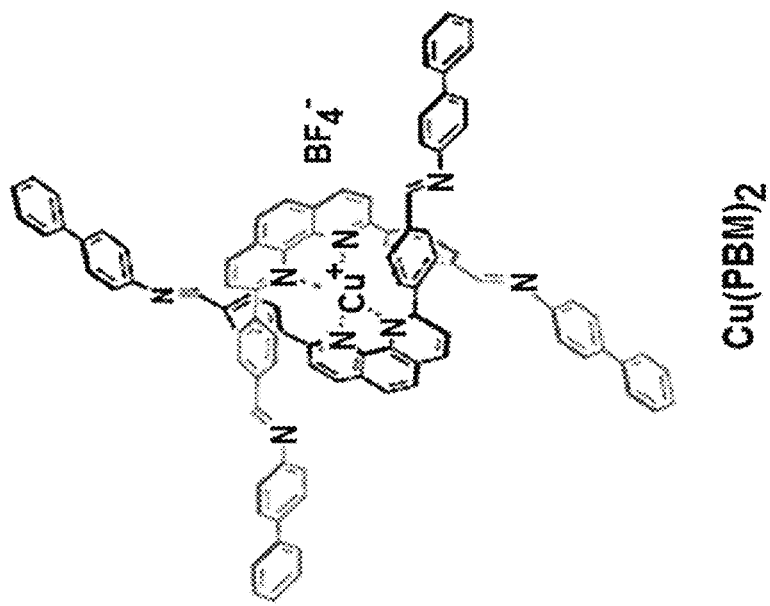

Additional embodiments for synthesize a linking ligand disclosed herein are presented in FIG. 5.

By using the linking moieties described herein, extended chemical structures with mutual interlacing of long organic helical threads was emulated. In order to successfully design weaving of chains into two- and three-dimensional (2D and 3D) chemical structures (see FIGS. 1A and 1B), long organic helical threads were designed to cross at regular intervals. These crossings served as points-of-registry so that the threads can have many degrees of freedom to move away and back to such points without collapsing the overall structure.

The disclosure provides a general strategy and its implementation for the designed synthesis of a woven chemical material (e.g., covalent organic framework-505, COF-505). COF-505 has helical organic threads interlacing to make a weaving crystal structure with the basic topology of FIG. 1B, and show that this material has an unusual behavior in elasticity. Although terms such as interweaving, polycatenated and interpenetrating have been used to describe interlocking of 2D and 3D extended objects (see FIGS. 1C and D), most commonly found in MOFs, the term weaving is used herein to describe exclusively the interlacing of 1D units to make 2D and 3D structures (see FIGS. 1A and B). Weaving differs from the commonly observed interpenetrating and polycatenated frameworks as the latter is topologically interlocked (i.e. interlocking rings, FIGS. 1C and D, insets), while the weaving constructs provided here have many more degrees of freedom for enormous spatial deviations, by each of the threads, to take place independently and still preserve the underlying topology. Such freedom enables reversible control over the mechanical properties of materials.

The weaving strategy reported here is potentially applicable to the conversion of other network topologies to weaving structures. In addition to the dia net of COF-505, a variety of other two- and three-dimensional topologies can also be achieved by weaving of threads (variously colored) using metal ions as points-of-registry. Tetrahedrally coordinated metal complexes with two ligands can be employed as tetratopic building units in reticular synthesis to construct weaving structures of corresponding topologies (e.g. pnf, qtz and sod). Metal ions with an octahedral coordination geometry, which provides another type of points-of-registry by coordinating three ligands, can also be used to synthesize weaving structures (e.g. kgm and pcu).

The materials provided herein provide tunable mechanical properties and dynamics, and thus, can be used towards synthesis of resilient materials for a variety of purposes including shape-memory material development, biomedical applications, etc.

The following examples are intended to illustrate but not limit the disclosure. While they are typical of those that might be used, other procedures known to those skilled in the art may alternatively be used.

EXAMPLES

All starting materials and solvents, unless otherwise specified, were obtained from Aldrich Chemical Co. and used without further purification. Tetrahydrofuran (HPLC grade, Aldrich) was passed through a PureSolv MD 7 Solvent Purification System before use. 4,4'-(1,10-Phenanthroline-2,9-diyl)dibenzaldehyde was synthesized according to published literature. All reactions were performed at ambient laboratory conditions, and no precautions taken to exclude atmospheric moisture, unless otherwise specified. Pyrex glass tube charged with reagents and flash frozen with liquid $N_2$ were evacuated using a Schlenk line by fitting the open end of the tube inside a short length of standard rubber hose that was further affixed to a ground glass tap which could be closed to insulate this assembly from dynamic vacuum when the desired internal pressure was reached. Tubes were sealed under the desired static vacuum using an oxygen propane torch.

Synthesis of 2,9-bis(4-(5,5-dimethyl-1,3-dioxan-2-yl)phenyl)-1,10-phenanthroline (3; scheme I)

To a dry 500 mL round bottom flask, 2,9-dibromo-1,10-phenanthroline (1, 800 mg, 2.37 mmol), 2-(4-(5,5-dimethyl-1,3-dioxan-2-yl)phenyl)-4,4,5,5-tetramethyl-1,3,2-dioxaborolane (2, 1.69 g, 5.33 mmol), tetrakis(triphenylphosphine)palladium(0) (191 mg, 0.170 mmol) were added and stirred in 150 mL of toluene for 1 h at ambient temperature under nitrogen. Subsequently, barium hydroxide (2.24 g, 7.10 mmol) and 150 mL of water was added. This mixture was heated at reflux overnight, after which the reaction was cooled to ambient temperature. The layers were separated and the aqueous layer was washed with dichloromethane (DCM, 50 mL×3). The organic layers were combined and dried over $MgSO_4$. The solvent was removed by evaporation in vacuo and the resulting crude product was purified using column chromatography was with DCM. Product 3 was isolated as a white solid (923 mg, 70% yield). 1H NMR (400 MHz, Chloroform-d) δ 8.49 (d, J=8.3 Hz, 4H), 8.29 (d, J=8.4 Hz, 2H), 8.15 (d, J=8.4 Hz, 2H), 7.78 (s, 2H), 7.73 (d, J=8.3 Hz, 4H), 5.52 (s, 2H), 3.84 (d, J=11.0 Hz, 4H), 3.72 (d, J=11.0 Hz, 4H), 1.36 (s, 6H), 0.84 (s, 6H).

Synthesis of 4,4'-(1,10-phenanthroline-2,9-diyl) dibenzaldehyde (4; Scheme I)

A 5% HCl aqueous solution (36 mL) was added to a stirring solution of 3 (900 mg, 1.61 mmol) in tetrahydrofuran (180 mL). The mixture was stirred at ambient temperature for 48 h, and then the solvent was evaporated in vacuo. The residue was suspended in a saturated $NaHCO_3$ aqueous solution (100 mL) and DCM (100 mL). The organic layer was collected and dried over $MgSO_4$. The solvent was removed by evaporation and resulting crude product was purified by column chromatography using DCM. Product 4 was isolated as a white solid (525 mg, 84% yield). 1H NMR (400 MHz, Chloroform-d) δ 10.15 (s, 2H), 8.63 (d, J=8.2 Hz, 4H), 8.40 (d, J=8.4 Hz, 2H), 8.23 (d, J=8.4 Hz, 2H), 8.12 (d, J=8.2 Hz, 4H), 7.88 (s, 2H).

Synthesis of $Cu(PDB)_2$ complex (5; Scheme I)

A degassed solution of $Cu(CH_3CN)_4BF_4$ (211 mg, 0.670 mmol) in $CH_3CN$ (12.5 mL) was added to a degassed solution of 4 (521 mg, 1.34 mmol) in $CHCl_3$ (25 mL). The solution immediately turned red, indicating complex formation. After the solution was stirred at ambient temperature for 0.5 h, the solvent was removed by evaporation in vacuo. Product 5 was isolated as a red solid (620 mg, quantitative yield). 1H NMR (400 MHz, DMSO-d6) δ 9.67 (s, 4H), 8.82 (d, J=8.3 Hz, 4H), 8.18 (d, J=8.3 Hz, 4H), 8.14 (s, 3H), 7.61 (d, J=7.8 Hz, 8H), 7.07 (d, J=7.8 Hz, 8H). Solution $^1$H nuclear magnetic resonance (NMR) spectra were recorded on a Bruker AVQ-400 (400 MHz) spectrometer operating with an Avance electronics console.

Synthesis of COF-505

Synthesis of Cu(I)-bis[4,4'-(1,10-phenanthroline-2,9-diyl)dibenzaldehyde] tetrafluoroborate $[Cu(PBD)_2]$: $[Cu(CH_3CN)_4]BF_4$ (388 mg, 1.00 mmol) was dissolved in anhydrous $CH_3CN$ (8 mL) under a $N_2$ atmosphere and then added to a solution of 4,4'-(1,10-phenanthroline-2,9-diyl) dibenzaldehyde (157 mg, 0.500 mmol) in $CHCl_3$ (16 mL), affording a dark red solution. After stirring the solution at ambient temperature for 30 min, the solution was then concentrated in vacuo to afford an analytically pure compound as a red solid (545 mg, quantitative). $^1$H NMR (400 MHz, $CDCl_3$) δ 9.69 (s, 4H), 8.29 (d, 3J=7.9 Hz, 8H), 8.18 (d, 3J=8.4 Hz, 4H), 8.07 (d, 3J=8.4 Hz, 4H), 7.70 (d, 3J=7.9 Hz, 8H), 7.60 (s, 4H). ESI-MS for $[C_{52}H_{32}CuN_4O_4]^+$ (Calcd. 839.17): m/z=839.17 ([M]$^+$, 100%); Elemental analysis: Calcd. For $C_{100}H_{68}BCuF_4N_8$: C, 67.36; H, 3.48; N, 6.04%. Found: C, 66.34; H, 3.37; N, 5.81%.

Synthesis and Activation of COF-505

A Pyrex tube measuring 10×8 mm (o.d×i.d) was charged with $Cu(PBD)_2$ (15 mg, 0.016 mmol), benzidine (6.0 mg, 0.032 mmol), anhydrous THF (1 mL) and 6 M aqueous acetic acid solution (0.1 mL). The tube was flash frozen at 77 K (liquid $N_2$ bath), evacuated to an internal pressure of 50 mTorr and flame sealed. Upon sealing, the length of the tube was reduced to 18-20 cm. The reaction was heated at 120° C. for 72 h yielding a brown solid at the bottom of the tube which was isolated by centrifugation and washed with anhydrous THF and dried at 120° C. under 50 mTorr for 12 h. This material is insoluble in water and common organic solvents such as hexanes, methanol, acetone, tetrahydrofuran, N,N-dimethylformamide, and dimethyl sulfoxide, indicating the formation of an extended structure. Yield: 18.7 mg, 94.4% based on $Cu(PBD)_2$. Elemental analysis: for $C_{76}H_{48}BCuF_4N_8 \cdot 4H_2O$: Calcd. C, 70.45; H, 4.36; N, 8.65%. Found: C, 70.13; H, 4.03; N, 8.50%.

Synthesis of the molecular analogue of COF-505, Cu(I)-bis[(1E,1'E)-1,1'-((1,10-phenanthroline-2,9-diyl)bis(4,1-phenylene))bis(N-([1,1'-biphenyl]-4-yl) methanimine)] tetrafluoroborate $[Cu(PBM)_2]$ A mixture of $Cu(PBD)_2$ (50.0 mg, 0.108 mmol) and 4-phenyl-aniline (110 mg, 0.648 mmol) in anhydrous p-xylene and $CHCl_3$ 1:1 mixture (15 mL) was stirred under reflux equipped with a Dean-Stark apparatus over 24 h. A dark grey solid was precipitated by adding additional p-xylene after cooling down the mixture to ambient temperature. The precipitant was collected by filtration and dried in vacuo(49 mg, 99% yield). 1H NMR (600 MHz, DMSO-d6) δ 8.81 (d, 3J=8.1 Hz, 4H), 8.33 (s, 4H), 8.19 (d, 3J=8.2 Hz, 4H), 8.12 (s, 4H), 7.76 (d, 3J=7.8 Hz, 8H), 7.72 (d, 3J=7.5 Hz, 8H), 7.60 (d, 3J=7.9 Hz, 8H), 7.49 (t, 3J=7.7 Hz, 8H), 7.39 (s, 4H), 7.37 (d, 3J=7.5 Hz, 8H), 7.13 (d, 3J=7.7 Hz, 8H). ESI-MS for $[C_{100}H_{68}CuN_8]^+$ (Calcd. 1444.49): m/z=1444.48 ([M]+, 100%); Elemental analysis: Calcd. For $C_{100}H_{68}BCuF_4N_8$: C, 78.40; H, 4.47; N, 7.31%. Found: C, 76.25; H, 4.55; N, 6.92%.

Single-Crystal X-Ray Diffraction.

Single-crystals of the complex were crystallized by the slow diffusion of hexane vapor into a $CH_2Cl_2$ solution of $Cu(PBD)_2$. A red block-shaped crystal (0.150×0.120×0.100 mm) was mounted on a Bruker D8 Venture X-ray diffractometer equipped with a fine-focus Mo target X-ray tube operated at 40 W power (40 kV, 1 mA) and a PHOTON 100 CMOS detector. The specimen was cooled to −123° C. using an Oxford Cryosystem chilled by liquid nitrogen. The Bruker APEX2 software package was used for data collection; the SAINT software package was used for data reduction; SADABS was used for absorption correction; no correction was made for extinction or decay. The structure was solved by direct methods in a triclinic space group P-1 with the SHELXTL software package and further refined with the least squares method. All non-hydrogen atoms were refined anisotropically, all hydrogens were generated geometrically. The details of crystallography data are shown in TABLE 1 and TABLE 2.

TABLE 1

Crystal data and structure refinement $Cu(PBD)_2$.

| | |
|---|---|
| Chemical formula | $C_{53}H_{34}BCl_2CuF_4N_4O_4$ |
| Formula weight | 1012.09 |
| Wavelength | 0.71073 Å |
| Crystal system | Triclinic |
| Space group | P-1 |
| Unit cell dimensions | a = 12.987(5) Å   α = 88.288(7)° |
| | b = 12.995(5) Å   β = 81.131(7)° |
| | c = 14.074(5) Å   γ = 67.000(6)° |
| Volume | 2159.1(13) Å$^3$ |
| Z | 2 |
| Absorption coefficient | 0.703 mm$^{-1}$ |
| Crystal size | 0.150 × 0.120 × 0.100 mm$^3$ |
| Theta Min-Max | 1.465 to 25.427° |
| Reflections collected | 73691 |
| Independent reflections | 7942 [R(int) = 0.0510] |

TABLE 1-continued

Crystal data and structure refinement Cu(PBD)$_2$.

| | |
|---|---|
| Completeness to theta = 25.000° | 100.0% |
| Goodness-of-fit on F$^2$ | 1.046 |
| Final R indices [I > 2σ(I)] | R$_1$ = 0.0358, wR$_2$ = 0.0961 |
| R indices (all data) | R$_1$ = 0.0399, wR$_2$ = 0.0999 |
| Largest diff. peak and hole | 0.782 and −0.485 e · Å$^{-3}$ |

The geometry around the copper can be described as distorted tetrahedral with approximate C$_2$ symmetry. The C$_2$ symmetry is indicated by the six N—Cu—N bond angles and the four Cu—N bonds in similar lengths (TABLE 2).

TABLE 2

Selected Structural Data for Complex Cu(PBD)$_2$.

| | Distances/Å |
|---|---|
| N(1)—Cu(1) | 2.0624(18) |
| N(2)—Cu(1) | 2.0626(18) |
| N(3)—Cu(1) | 2.1011(18) |
| N(4)—Cu(1) | 2.0349(18) |
| | Angles/° |
| N(4)—Cu(1)—N(1) | 142.26(7) |
| N(4)—Cu(1)—N(2) | 126.80(7) |
| N(1)—Cu(1)—N(2) | 82.22(7) |
| N(4)—Cu(1)—N(3) | 81.55(7) |
| N(1)—Cu(1)—N(3) | 123.16(7) |
| N(2)—Cu(1)—N(3) | 95.82(7) |

Figure 6:
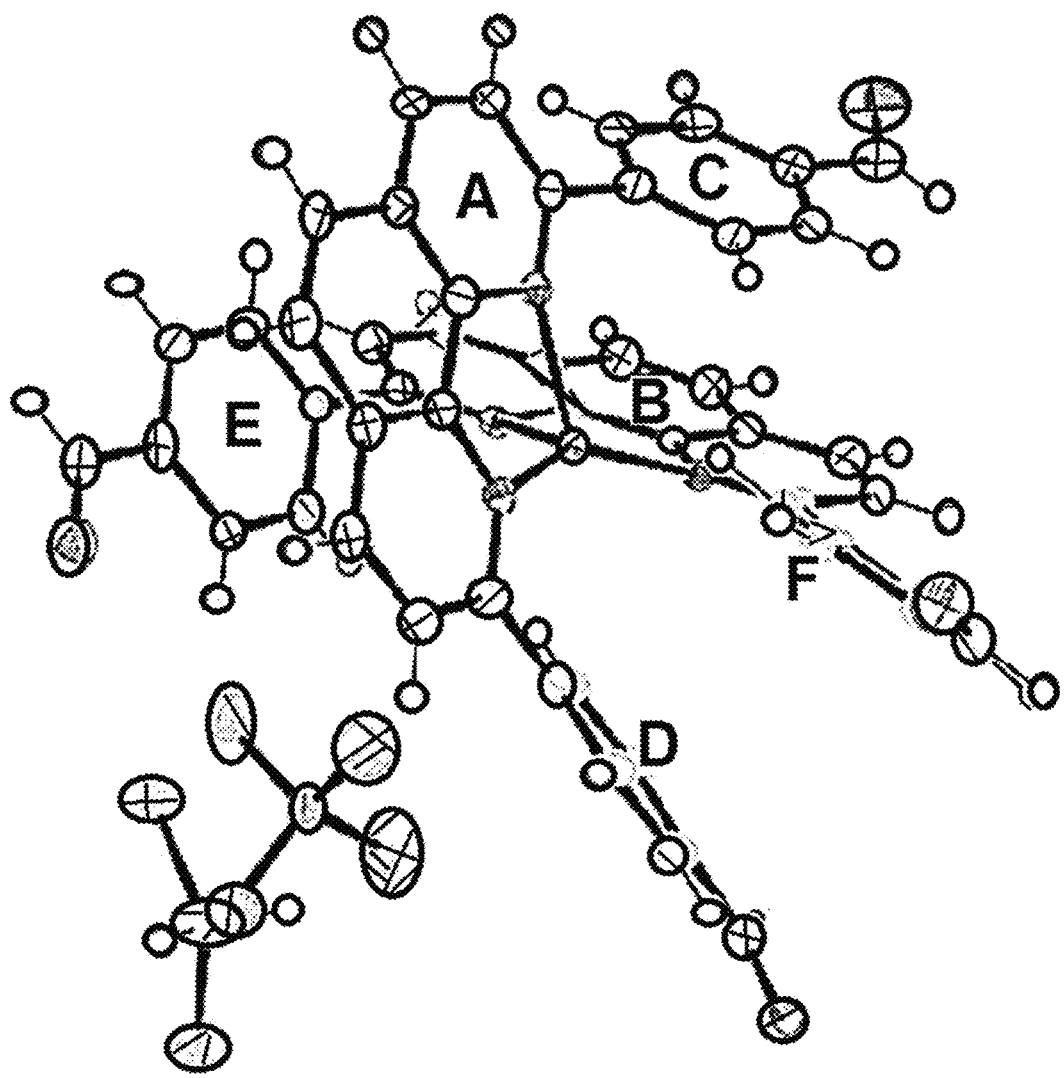
FIG. 6 provides an ORTEP drawing of the crystal structure of $Cu(PBD)_2$. Thermal ellipsoids are shown with 50% probability.
Figure 7:
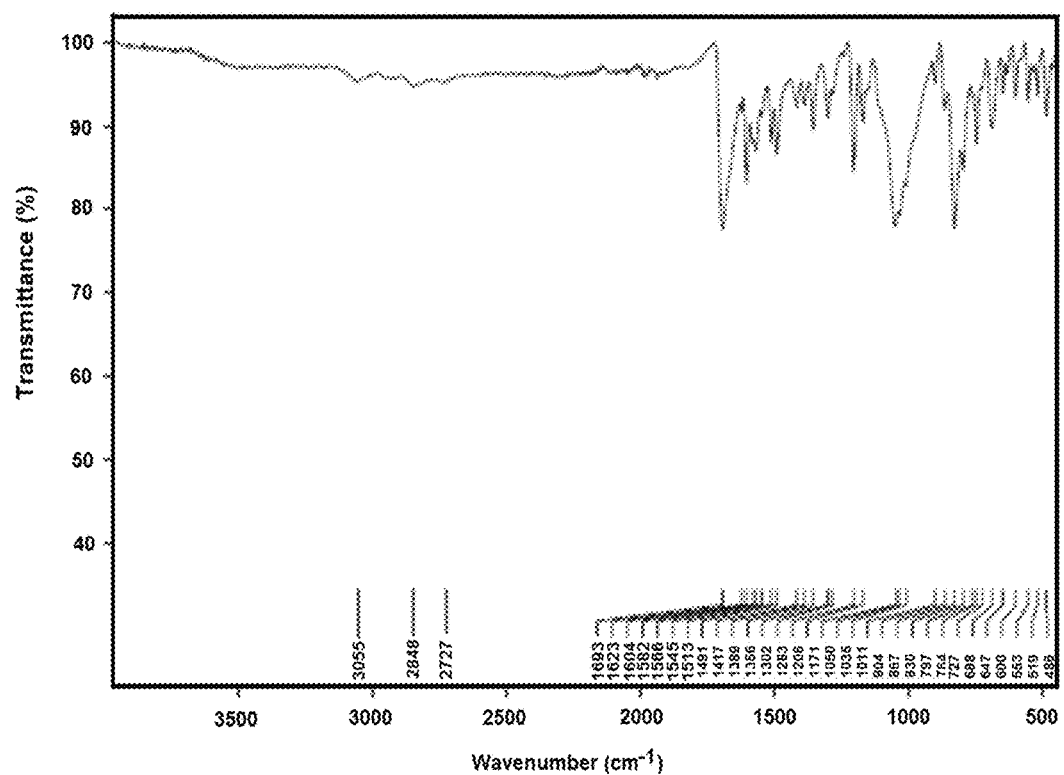
FIG. 7 presents a FT-IR spectrum of $Cu(PBD)_2$.
Figure 8:
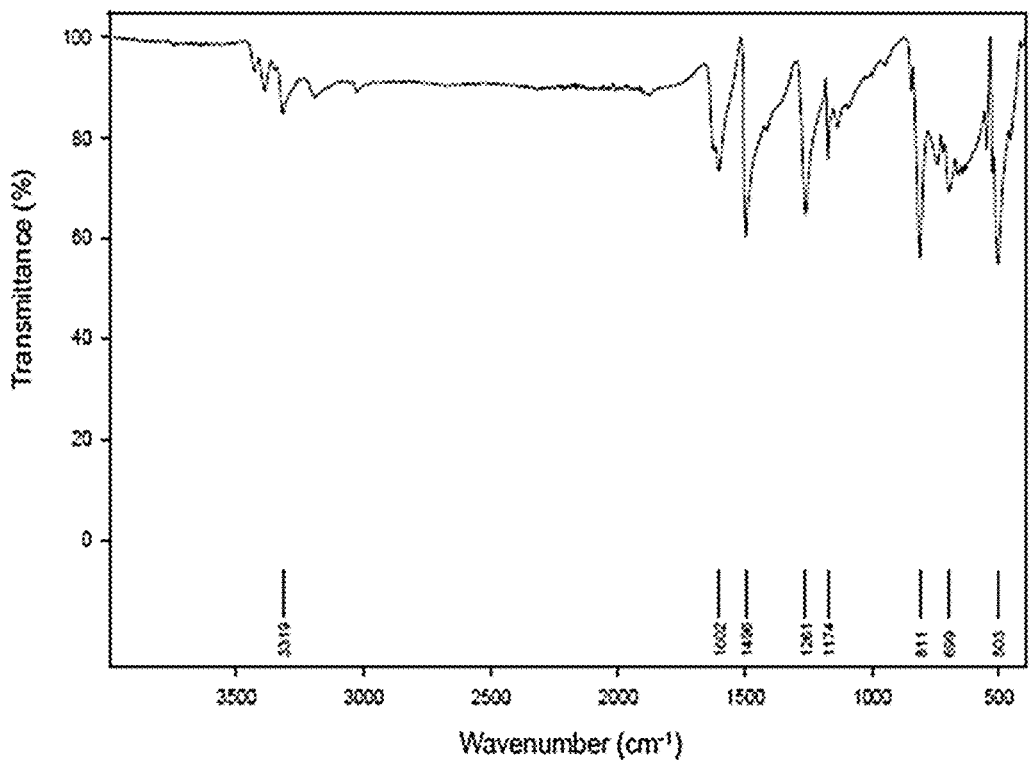
FIG. 8 displays a FT-IR spectrum of BZ.
Figure 9:
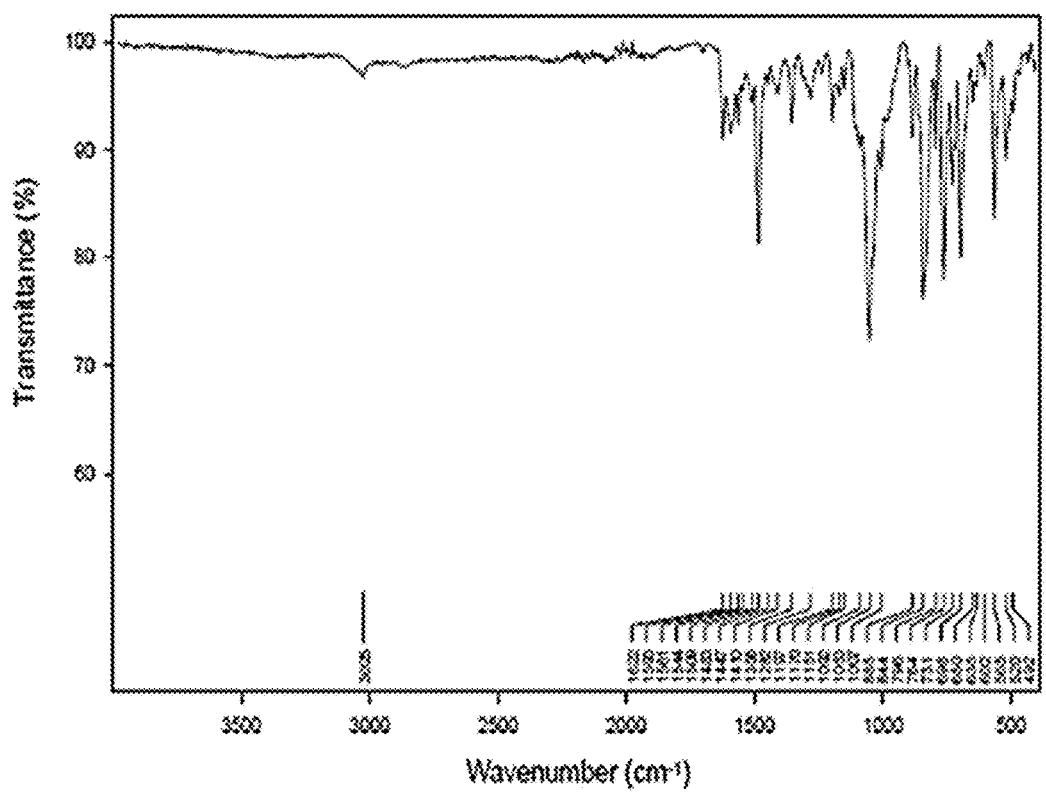
FIG. 9 presents a FT-IR spectrum of molecular analogue $Cu(PBM)_2$.
Figure 10:
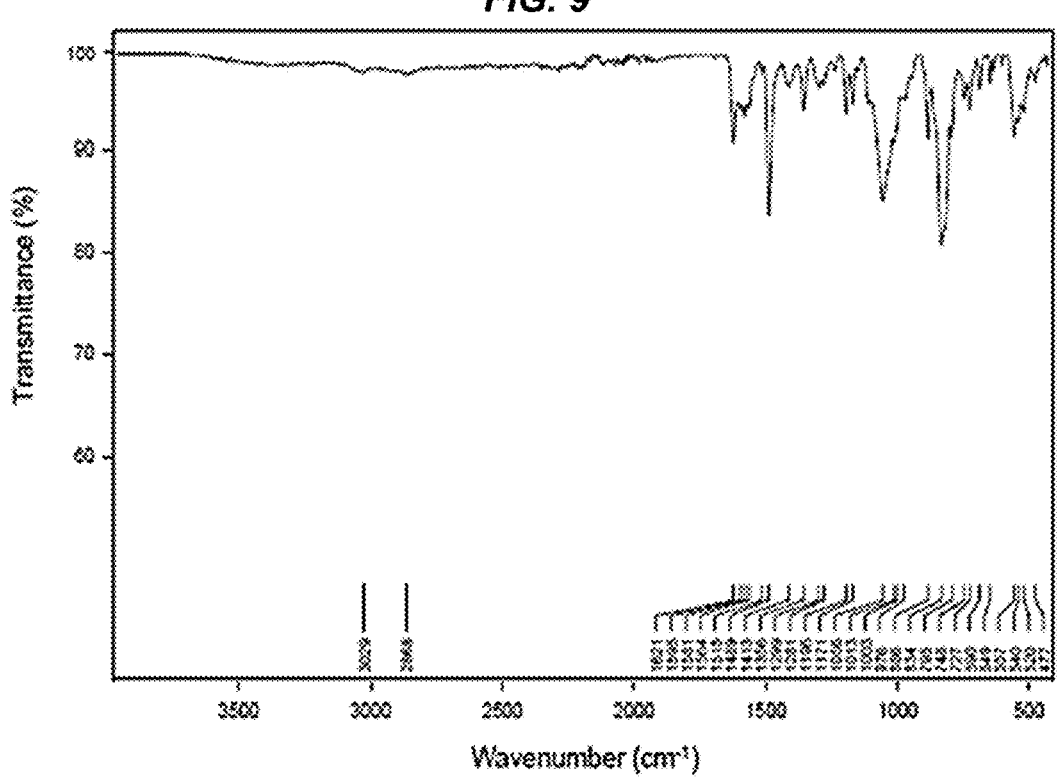
FIG. 10 displays a FT-IR spectrum of activated COF-505.
Figure 11:
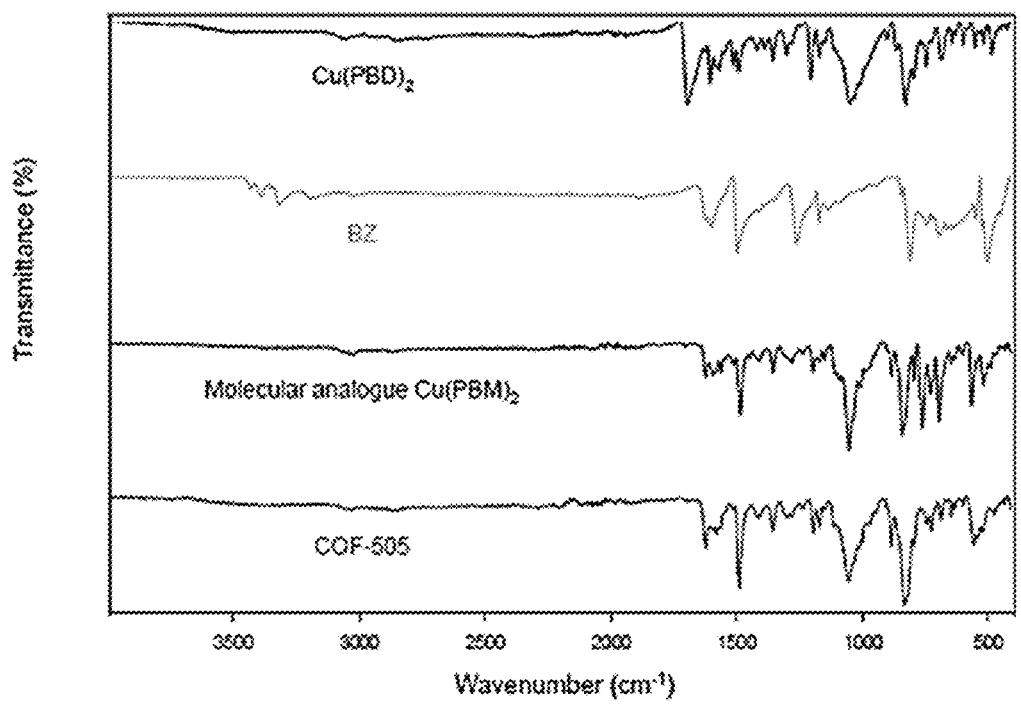
FIG. 11 presents a stack plot of FT-IR spectra for the comparison between starting materials, molecular analogue, and activated COF-505.
Figure 12:
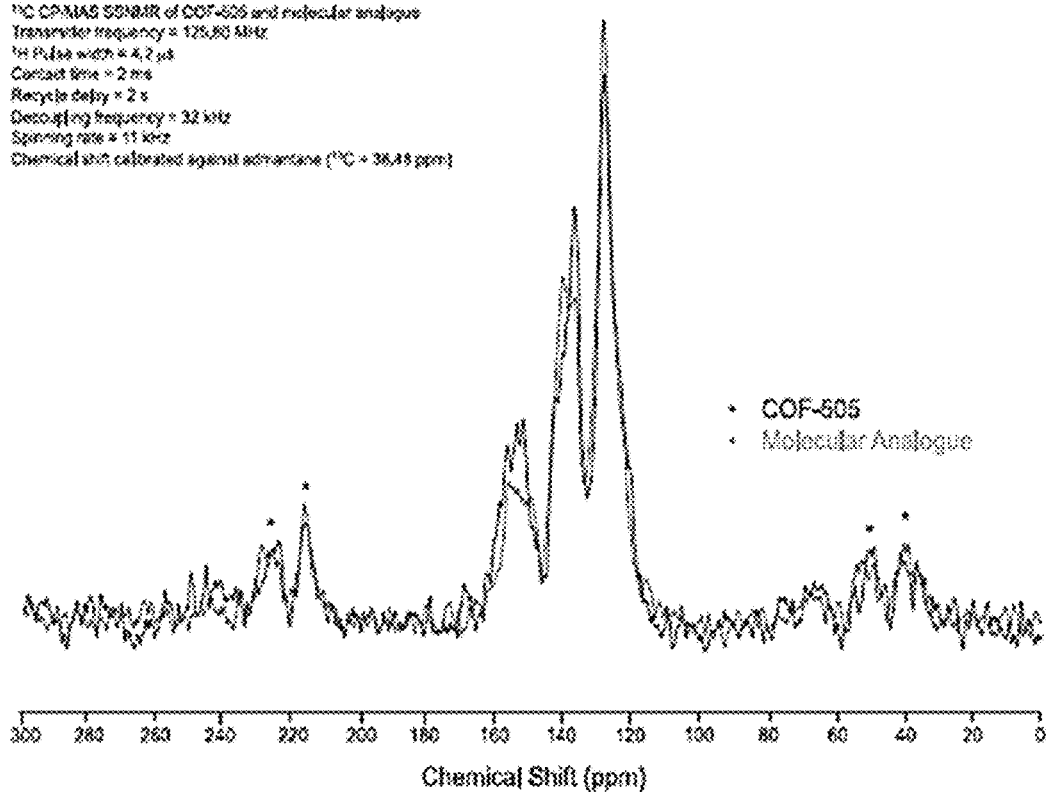
FIG. 12 presents a solid-state $^{13}C$ CP/MAS NMR spectrum of COF-505 and its molecular analogue.
Figure 13:
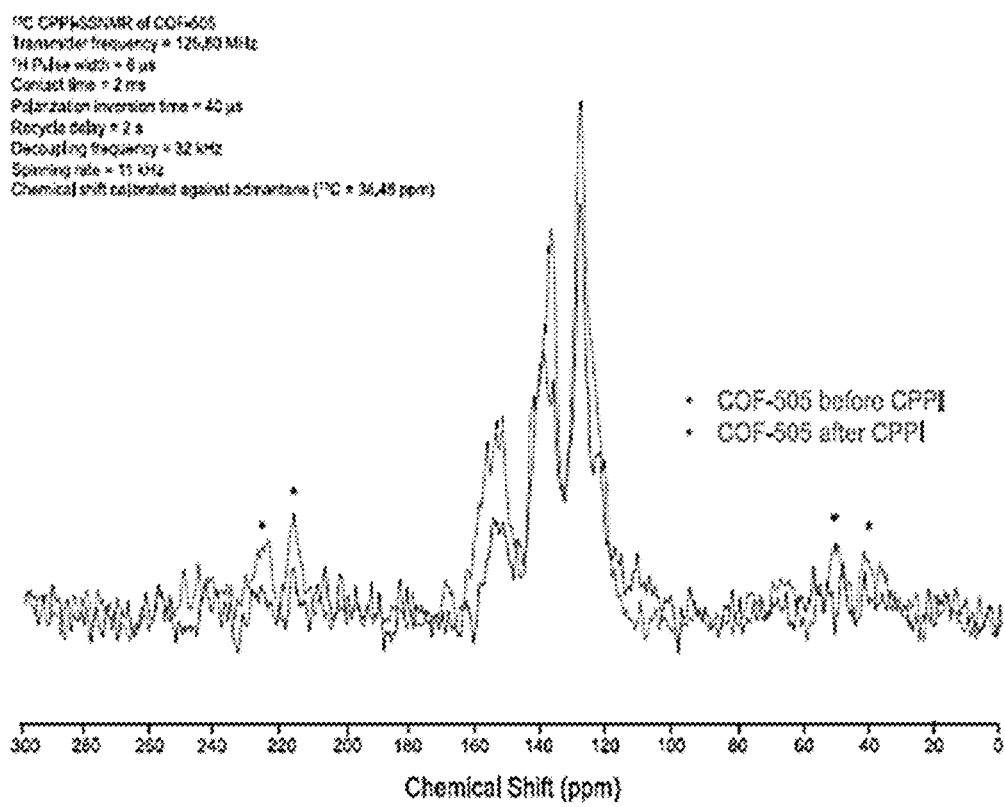
FIG. 13 presents a solid-state $^{13}C$ NMR spectrum of COF-505 before and after CPPI technique.
Figures 14A, 14B:
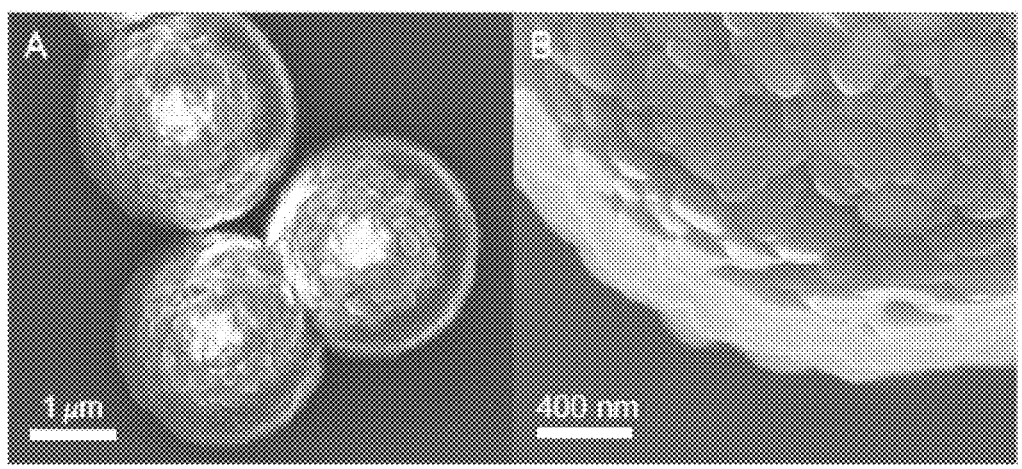
FIG. 14A-B displays the morphology of COF-505 by SEM. (A) Crystalline spheres from aggregated crystallites. (B) Crystal plates on the surface of a sphere.

The C$_2$ axis bisects the N1B—Cu—N1A angle, thus relating the two phenanthroline ligands and resulting in approximate molecular C$_2$ symmetry. A significant feature of the structure is the n-stacking interactions at 3.4 Å and 3.8 Å between phenanthrolines A and B and phenyl groups E and C, respectively (see FIG. 6). In addition, intermolecular phenyl-phenyl n-stacking interactions at 4.0 Å are also present, resulting in phenyl-phenanthroline-phenyl-phenyl-phenanthroline-phenyl n-stacks in the unit cell.

Fourier Transform Infrared Spectroscopy.

The FT-IR spectra of starting materials, molecular analogue, and activated COFs were collected on a Bruker ALPHA FT-IR Spectrometer equipped with ALPHA's Platinum ATR single reflection diamond ATR module, which can collect IR spectra on neat samples. The signals are given in wavenumbers (cm$^{-1}$) and described as: very strong (vs), strong (s), medium (m), shoulder (sh), weak (w), very weak (vw) or broad (br) (see TABLE 3).

TABLE 3

Peak assignment for the FT-IR spectrum of COF-505. Notes and discussion are provided to correlate the spectra of starting material.

| Peak (cm$^{-1}$) | Assignment and Notes |
|---|---|
| 3029 (vw) | Aromatic C—H stretch from phenyl rings in complex Cu(PBD)$_2$. Present in model compound Cu(PBM)$_2$. |
| 2868 (vw) | Alkene C—H stretching from imine. Present in Cu(PBM)$_2$. |
| 1621 (m) | Imine C═N stretching. Present in Cu(PBM)$_2$. This bond is confirmed by the disappearance of the $v_{N-H}$ stretching mode from tetraanilylmethane (3319 cm$^{-1}$) and of the $v_{C=O}$ stretching mode from biphenyldicarboxaldehyde (1693 cm$^{-1}$). |

TABLE 3-continued

Peak assignment for the FT-IR spectrum of COF-505. Notes and discussion are provided to correlate the spectra of starting material.

| Peak (cm$^{-1}$) | Assignment and Notes |
|---|---|
| 1595 (m) | Aromatic C═C ring stretching from benzidine. |
| 1581 (m) | Aromatic C═C ring stretching from phenyl rings in complex Cu(PBD)$_2$. |
| 1564 (m) | Aromatic C═C ring stretching from Cu(PBD)$_2$. |
| 1515 (m) | Aromatic C═C ring stretching from Cu(PBD)$_2$. |
| 1489 (s) | Aromatic C—C ring stretching from Cu(PBD)$_2$. |
| 1413 (w) | Aromatic C—C ring stretching from Cu(PBD)$_2$. |
| 1356 (m) | Aromatic C—C ring stretching from Cu(PBD)$_2$. |
| 1299 (w) | Aromatic ring stretching from Cu(PBD)$_2$. |
| 1281 (w) | Aromatic ring stretching from Cu(PBD)$_2$. |
| 1196 (m) | Imine C—C═N—C stretching. This mode is the stretching of the C—C and C—N single bonds. |
| 1171 (m) | C—Ph breathing and C—C stretching from benzidine, characteristic of biphenyl. |
| 1056 (w) | B—F stretching from BF$_4$ anions. |
| 1013 (sh) | Aromatic C—H in-plane bending from phenyl rings in Cu(PBD)$_2$. |
| 1003 (sh) | Aromatic C—H in-plane bending from phenyl rings in Cu(PBD)$_2$. |
| 976 (sh) | Aromatic C—H in-plane bending from phenyl rings in Cu(PBD)$_2$. |
| 886 (m) | Aromatic C—H phenyl ring substitution bands from biphenyl rings in benzidine. |
| 834 (s) | Aromatic ring stretching from Cu(PBD)$_2$. |
| 795 (m) | Aromatic ring stretching from Cu(PBD)$_2$. |
| 748 (m) | Aromatic ring C—H out-of-plane bending from Cu(PBD)$_2$. |
| 727 (m) | Aromatic ring C—H out-of-plane bending from Cu(PBD)$_2$. |
| 690 (w) | Aromatic ring C—H out-of-plane bending from Cu(PBD)$_2$. |
| 649 (w) | Aromatic ring C—H out-of-plane bending from Cu(PBD)$_2$. |
| 557 (m) | Aromatic ring C—H out-of-plane bending from Cu(PBD)$_2$. |
| 540 (m) | Aromatic ring C—H out-of-plane bending from BZ. |
| 520 (m) | Aromatic ring C—H out-of-plane bending from Cu(PBD)$_2$. |
| 477 (w) | Aromatic ring C—H out-of-plane bending from BZ. |

Solid-State Nuclear Magnetic Resonance Spectroscopy.

Solid-state nuclear magnetic resonance (NMR) spectra were recorded at ambient pressure on a Bruker AV-500 spectrometer using a standard Bruker magic angle-spinning (MAS) probe with 4 mm (o.d.) zirconia rotors. The magic angle was adjusted by maximizing the number and amplitudes of the signals of the rotational echoes observed in the $^{79}$Br MAS FID signal from KBr. The transmitter frequency of $^{13}$C NMR is 125.80 MHz.

The solid-state $^{13}$C NMR spectra were acquired using cross-polarization (CP) MAS technique with the ninety degree pulse of $^1$H with 4.2 μs pulse width. The CP contact time was 2 ms. High power two-pulse phase modulation (TPPM)$^1$H decoupling was applied during data acquisition. The decoupling frequency corresponded to 32 kHz. The MAS sample spinning rates was 11 kHz. Recycle delays between scans were 2 s. The $^{13}$C chemical shifts are given relative to neat tetramethylsilane as zero ppm, calibrated using the methylene carbon signal of adamantane assigned to 38.48 ppm as secondary reference.

The experimental setup for cross-polarization and polarization inversion (CPPI) spectral editing is the same as the CPMAS experiment. Pulse sequences are included in work by Zilm and co-workers. Spectral editing parameters were determined as $^1$H with 6 μs pulse width, cross-polarization times of 2 ms, and a polarization inversion time of 40 μs.

Scanning Electron Microscopy.

Samples of COF-505 for SEM study were prepared by drop casting the acetone dispersion of the material onto a 1 cm² silicon wafer. SEM images were recorded on a Zeiss Gemini Ultra-55 Analytical scanning electron microscope with accelerating voltage of 5 kV with a working distance of 5 mm. Primary crystallites of size of 0.2×0.2 μm were aggregated into spheres with diameter of approximately 2 μm. No other forms were observed in the surveyed samples, and from morphology of primary crystallites were in the same phase.

Electron Diffraction Analyses by Transmission Electron Microscopy.

A cold field emission JEM-2100F equipped with a DELTA $C_s$ corrector operated at 60 kV was used for HRTEM imaging. Since COF materials are electron beam sensitive, the electron beam damage to the specimen was minimized as much as possible (in this study, the beam density during the observations was less than 500 electrons/(nm²·s)). A Gatan 894 CCD camera was used for digital recording of the HRTEM images. A single HRTEM image with an exposure time of 2 seconds or a sequence of images (up to 20 frames) was recorded, with a 1 or 2 seconds exposure time for each. After drift compensation, some frames can be superimposed to increase the signal-to-noise (SN) ratio for display. HRTEM images are filtered by a commercial software named HREM-Filters Pro (HREM Research Inc. Japan).

COF-505 crystals were dispersed into ethanol by ultrasonic oscillation and then dropped on a carbon film supported TEM grid. 3D electron diffraction tomography (3D-EDT) data were collected on a JEOL JEM-2100, with LaB6 filament and the control of EDT-collect program. The data was further processed by EDT-process program (see TABLE 4).

TABLE 4

Plane group of projection along [1-10] and multiplicities of general site for five different space groups

| Space group | Cm2a | Cmma | Cmca | Cc2a | Ccca |
|---|---|---|---|---|---|
| Plane group projected along [1-10] | pg | pg | pgg | pgg | pmg |
| Multiplicity for general site | 8 | 16 | 16 | 8 | 16 |

Powder X-Ray Diffraction Analysis.

Powder X-ray diffraction data of complex A and benzidine B were collected using a Bruker D8-advance θ-θ diffractometer in parallel beam geometry employing Cu Kα1 line focused radiation at 1600 W (40 kV, 40 mA) power and equipped with a position sensitive detector with at 6.0 mm radiation entrance slit. Samples were mounted on zero background sample holders by dropping powders from a wide-blade spatula and then leveling the sample with a razor blade. The best counting statistics were achieved by collecting samples using a 0.02° 2θ step scan from 1-40° with exposure time of 5 s per step.

PXRD of COF-505 was obtained by wide angle X-ray scattering (WAXS) using Pilatus 2M (Dectris) instrument on beamline 7.3.3 at the Advanced Light Source, Lawrence Berkeley National Laboratory (λ=1.24 Å). The sample-detector distance and beam center were calibrated using silver behenate. 1-D scattering profiles were reduced from the 2-d data using the Nika package for IGOR Pro (Wavemetrics). The 1-D plot shown in this material are plotted from WAXS data converted to 2θ values assuming λ=1.5406 Å (Cu Kα1).

Structural Modeling:

Unit cell parameters and possible space groups were determined using the electron diffraction experiments. The unit cell parameters were refined against the PXRD pattern with a Pawley refinement (a=18.6419 Å, b=21.4075 Å, c=30.2379 Å, orthorhombic, space group Cc2a). The initial positions of copper ions were obtained at the maxima of reconstructed 3D potential map from Fourier analysis of HRTEM image. A crystal model was built accordingly with the use of Materials Studio v6.0. Eight complex $Cu(PDB)_2$ molecules were put into one unit cell as a rigid body with copper positions fixed. The orientation of complex was initially refined using PXRD pattern. To make it an extended structure and according to the spectroscopic characterization, one $Cu(PDB)_2$ was connected to its four neighbors through BZ molecules. Then the crystal structure was optimized through a combination of energy and geometrical minimization and PXRD Rietveld refinement. Anions $BF_4^-$ were finally introduced into the model to compensate the charge of the Cu complexes, and to account for the missing electron density from electron diffraction studies. Since the position of the $BF_4^-$ anions does not affect the overall framework, the accurate positions of the anions may vary. The structure was further refined with the Rietvled method (Rwp=6.23%, Rp=4.35%).

The chemical content in one unit cell is $B_8C_{608}Cu_8F_{32}H_{384}N_{64}$, consisting of eight symmetrically equivalent $Cu(PBD)_2$, BZ and $BF_4$ units. The geometry of $Cu(PBD)_2$ in COF-505 was similar to that in its molecular crystal. The building units $Cu(PBD)_2$ are connected to each other through imine bonds with biphenyl linkers BZ. The closest distance between two Cu atoms is 8.5 Å. This short distance does not allow the connection between these two $Cu(PBD)_2$ and two mutually weaving nets are formed. The continuous connection of PDB and BZ units formed a helical thread along [110] or [−110] directions. As a result, COF-505 is a weaved framework consisting of helical threads.

The two frameworks are mutually woven in a way that is different to the commonly observed interpenetration and polycatenation modes. In the normally observed 2-fold dia interpenetration every 6-ring of one network is crossed by one and only one edge of the other network. However, some 6-rings are crossed by three edges of the other network and some edges pass through more than one rings in COF-505 network. This mode of polycatenation and interpenetration makes the particular weaving pattern in the structure COF-505.

Figure 15:
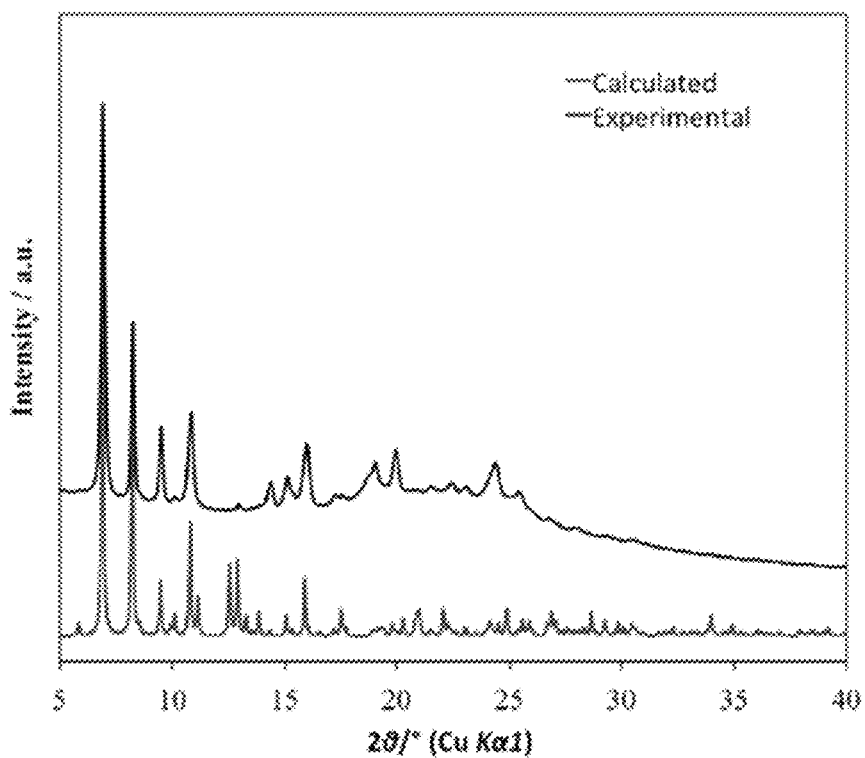
FIG. 15 provides a comparison of experimental and calculated PXRD patterns for COF-505.
Figure 16:
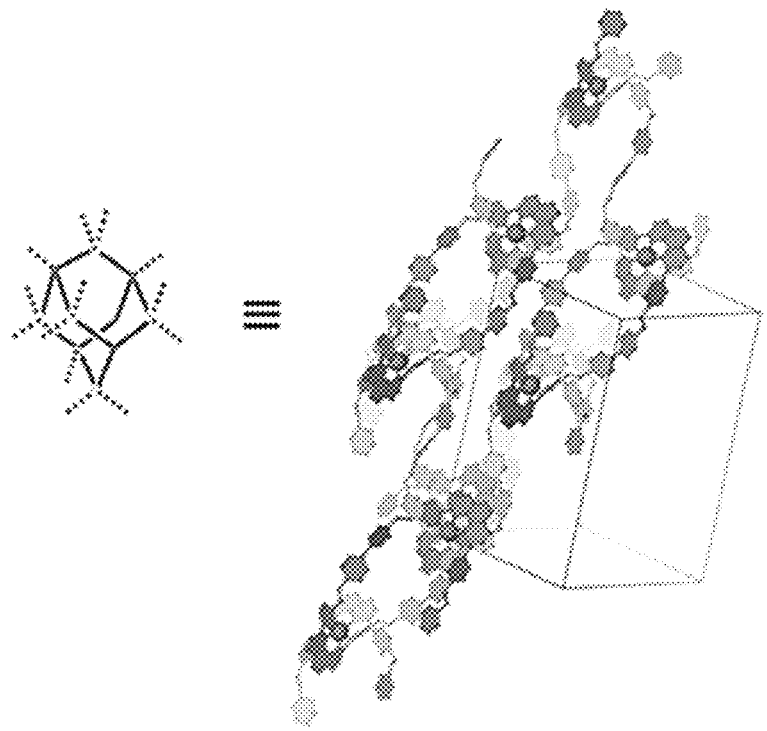
FIG. 16 presents the weaving adamantane cage of COF-505.
Figure 17:
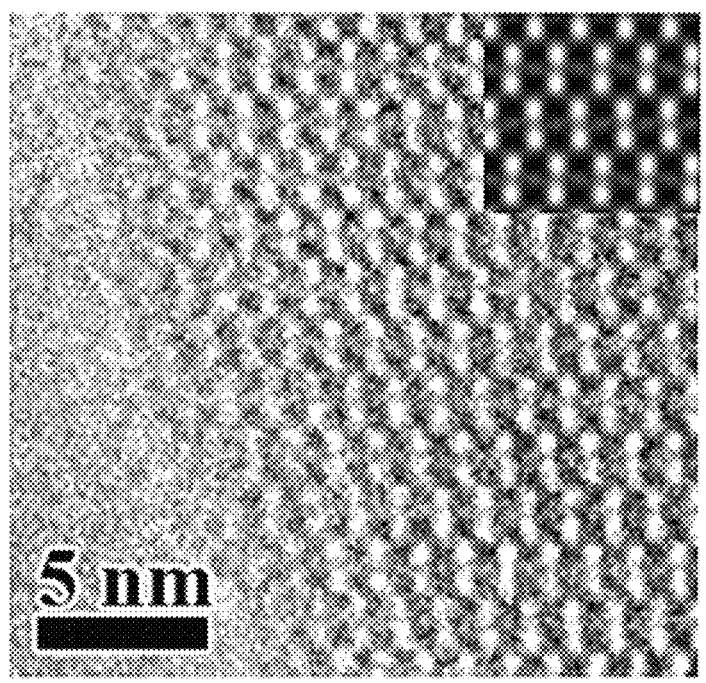
FIG. 17 displays an HRTEM image of a nano-crystal. The image can be explained if the crystal has the same space group symmetry with slightly different lattice constants from COF-505.
Figure 18:
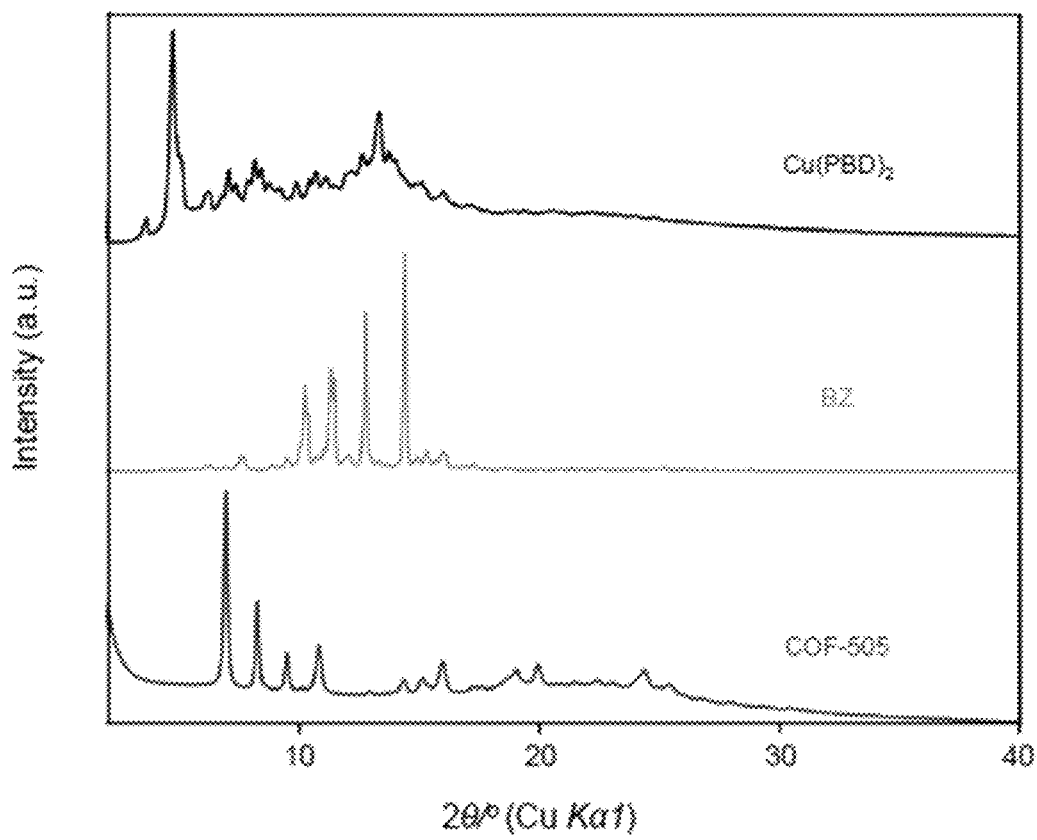
FIG. 18 provides a PXRD comparison of $Cu(PDB)_2$, BZ, and COF-505.

There is a minor phase found in HRTEM observations, which displays the same plane group symmetry as COF-505 along [1-10], but with slightly different lattice constants (see FIG. 15). The structure cannot be solved without whole 3d diffraction data, however this image can be explained if this nano-crystal has the same structure as the COF-505 with slight changes in lattice constants ($d_{110}/d_{001}$=12/31), i.e. contraction along [110] direction ($d_{110}$=12 Å compared to 14.2 Å for COF-505 if lattice constant c is kept constant) and/or expansion of lattice parameter c.

Thermalgravimetric Analysis.

Samples were run on a TA Instruments Q-500 series thermal gravimetric analyzer with samples held in a platinum pan under nitrogen atmosphere. A ramp rate of 5° C./min was used.

Synthetic Procedure for De-Metalation and Re-Metalation.

Figure 19:
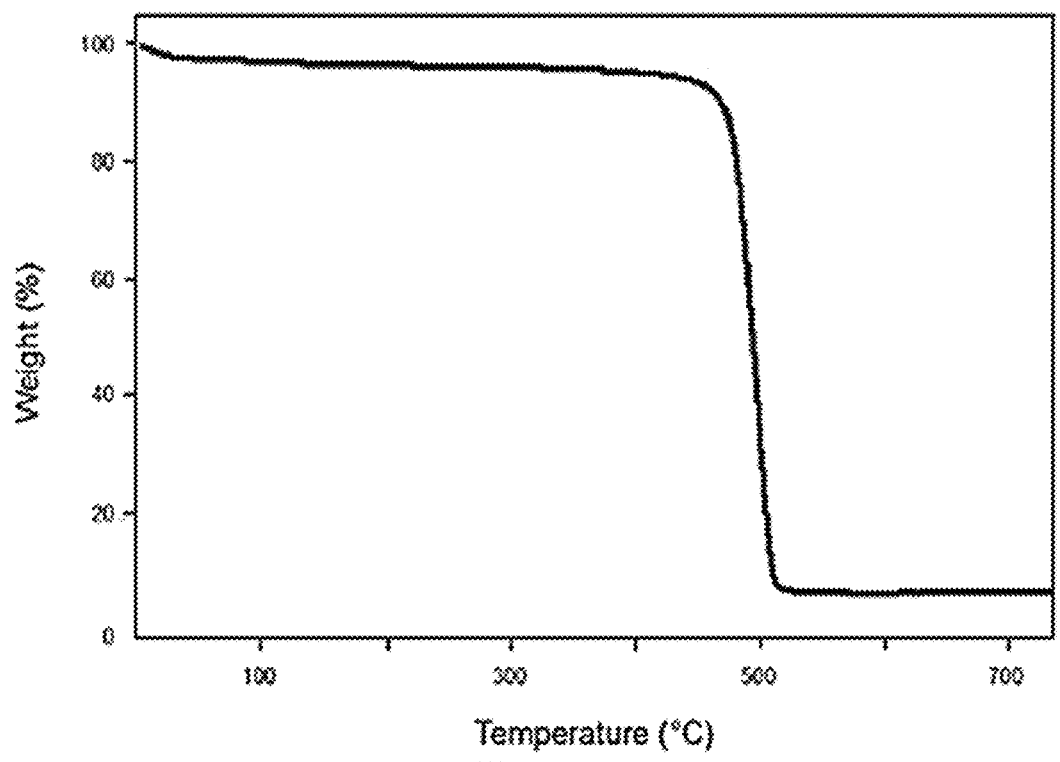
FIG. 19 provides a TGA trace for activated COF-505.
Figure 20:
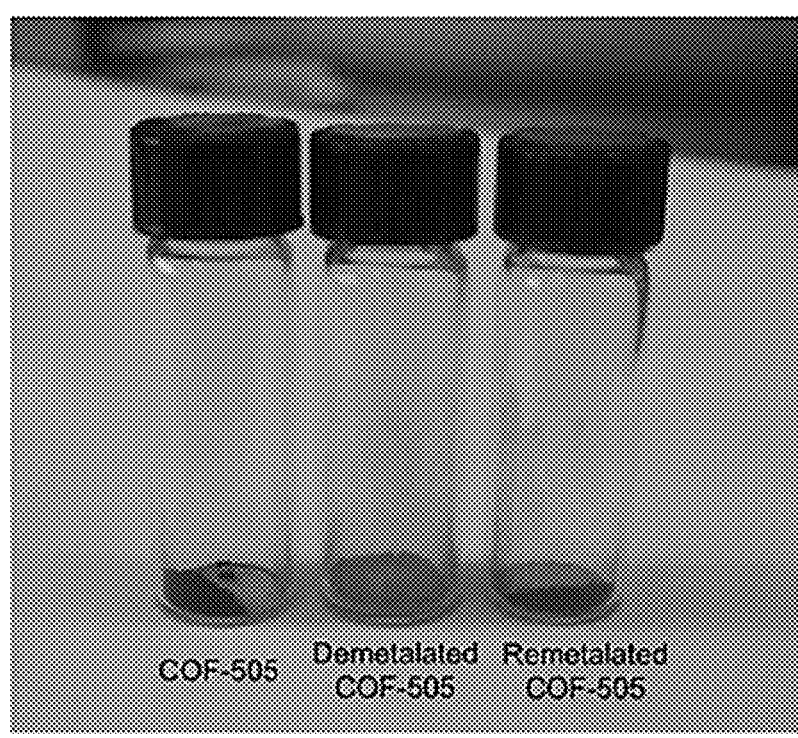
FIG. 20 provides images of vials comprising crystalline powder of COF-505 (left), de-metalated COF-505 (middle), and re-metalated COF-505 (right). The COF-505 sample changed color from dark brown to yellow as it was de-metalated and after re-metalation, the dark color was recovered.
Figure 21:
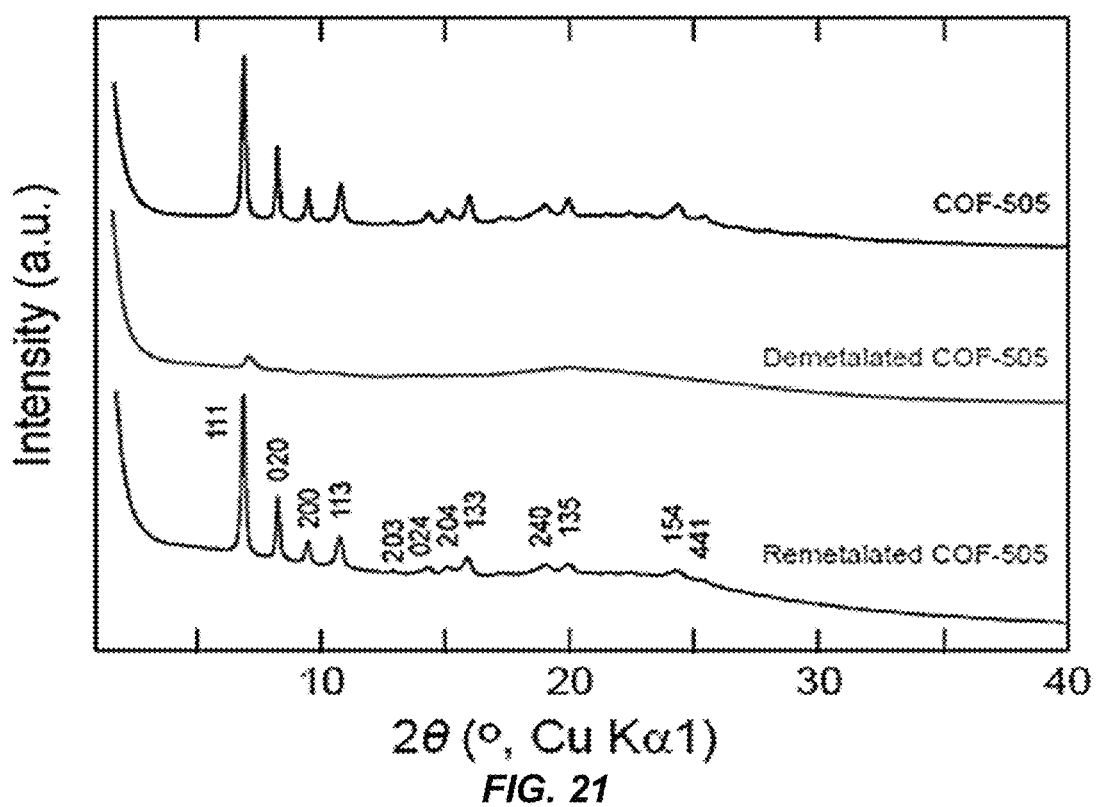
FIG. 21 presents PXRD patterns of as-synthesized COF-505, the de-metalated and re-metalated materials. The crystallinity of COF-505 decreases upon de-metalation and can be fully restored after re-metalation with copper(I) ions.
Figure 22:
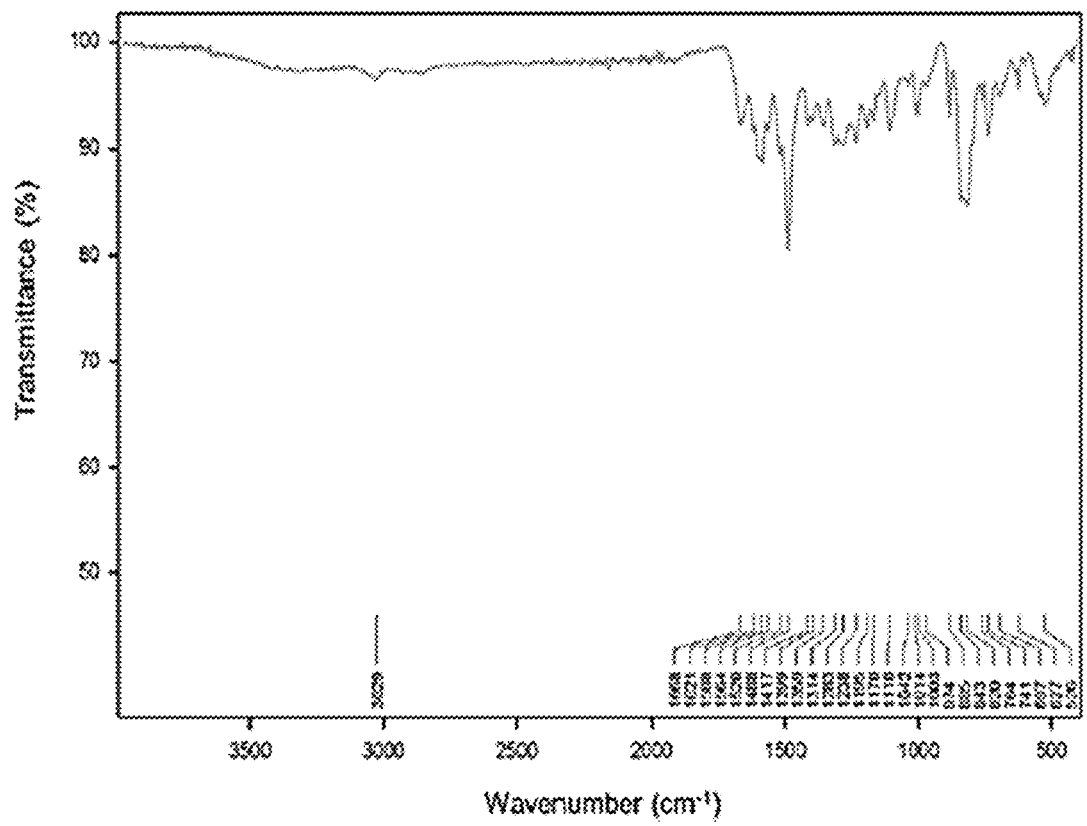
FIG. 22 provides a FT-IR spectrum of the de-metalated COF-505.
Figure 23:
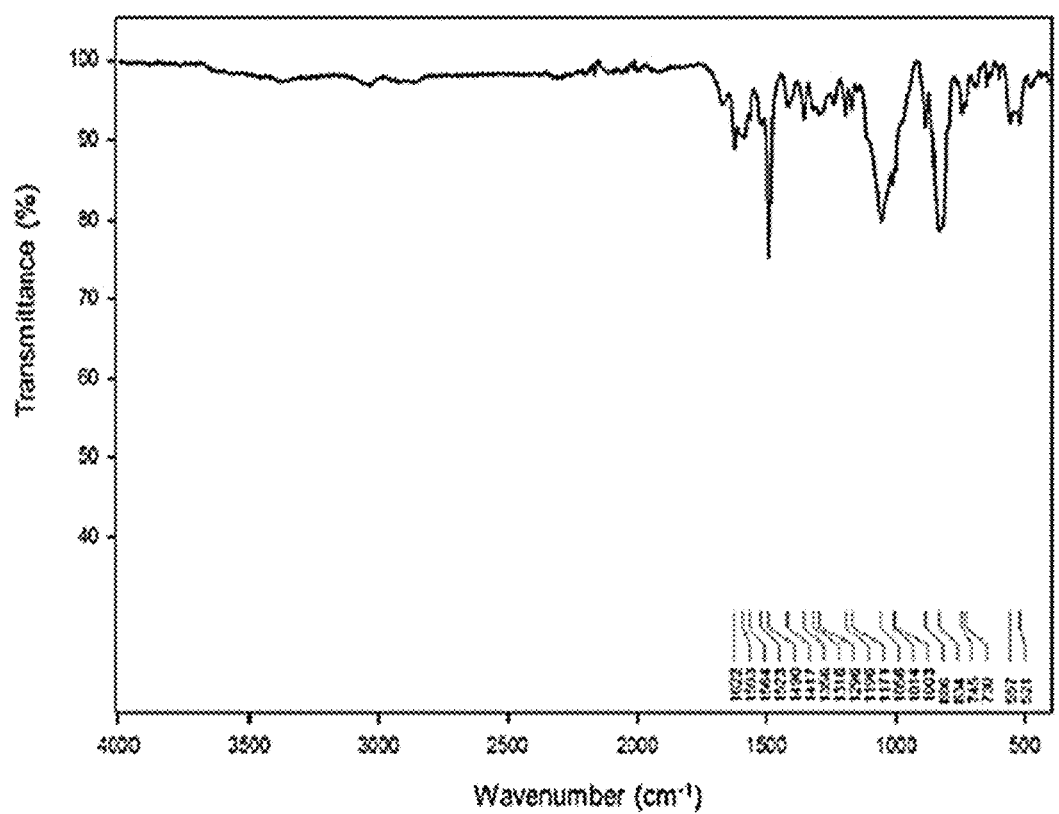
FIG. 23 provides a FT-IR spectrum of recovered COF-505 after re-metalation.
Figure 24:
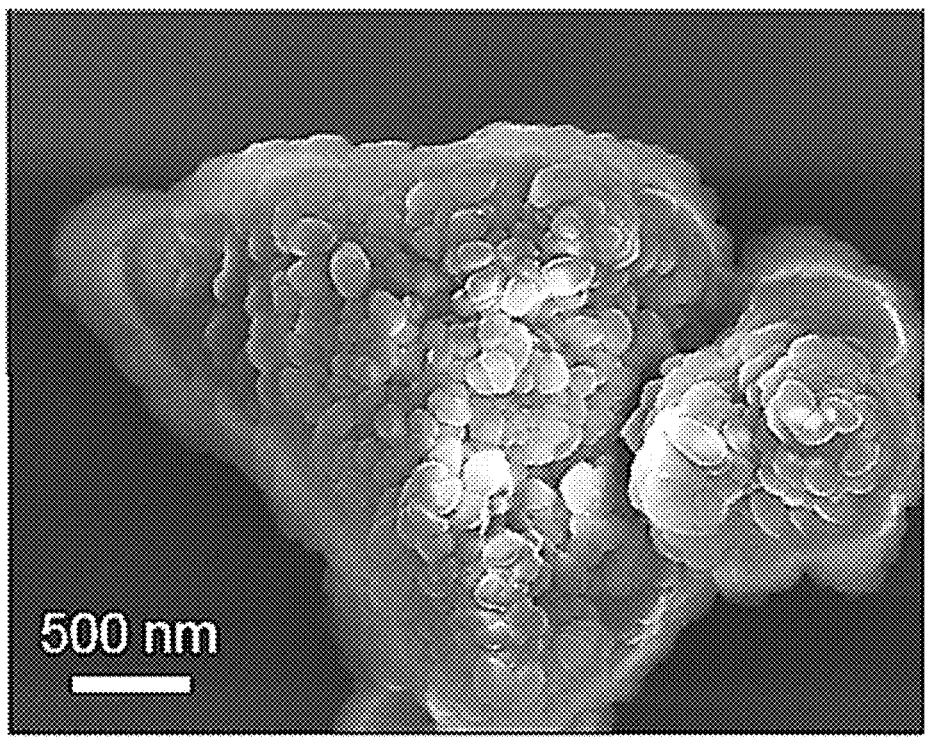
FIG. 24 presents a SEM image of the de-metalated material, which shows similar morphology to COF-505.

A 0.3 M KCN solution in a 1:5 mixture of MeOH and $H_2O$ was added to a suspension of COF-505 powder. The solution was heated at 90° C. The solution was replaced by a fresh solution of KCN every 24 h and this procedure was repeated three times. Control experiments without KCN solution was also conducted under otherwise identical conditions. Subsequently, both samples were washed with anhydrous CH$_3$OH and dried at 120° C. under 50 mTorr for 12 h. The de-metalated material was observed to be pale-yellow in color, in contrast to the dark brown color of COF-505 (see FIG. 19).

The re-metalation process was carried out in similar conditions with the complexation reaction to yield complex Cu(PBD)$_2$. Dried powder of the de-metalated material was immersed in anhydrous CHCl$_3$, to which was added a 0.01 M Cu(CH$_3$CN)BF$_4$ solution in CH$_3$CN. This mixture was stirred for 12 h under N$_2$ at ambient temperature and dark brown color was recovered (see FIG. 19).

Inductively Coupled Plasma Atomic Emission Spectroscopy.

Inductively coupled plasma atomic emission spectroscopy (ICP-AES) was used to determine the copper content in these materials. Samples were dissolved in OPTIMA grade nitric acid. The stock solutions were then diluted to 1:10 (v/v) with H$_2$O, which were analyzed on an Agilent 7500ce ICP-AES using helium collision gas mode. The copper content in COF-505 (C$_{76}$H$_{48}$BCuF$_4$N$_8$.4H$_2$O) is calculated to be 4.9% and measured to be 4.8%, while in the de-metalated material, it was determined to be in the range of 0.15% to 0.38%, approximately 3-8% of the original Cu concentration. After re-metalation, the Cu content was determined to be 3.9% to 4.2%, which is 82-88% of COF-505.

Atomic Force Microscopy.

Figure 25A:
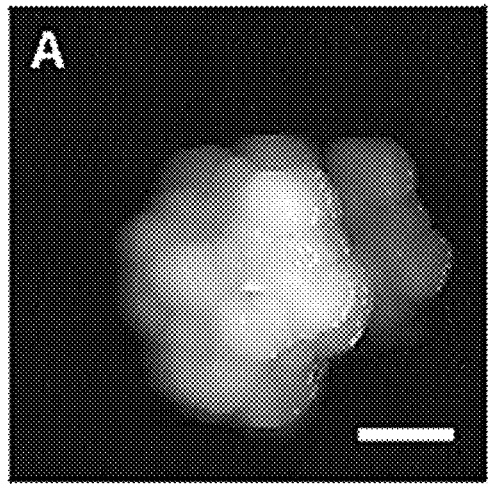
FIG. 25A-D provides AFM images of the COF particles (A) before and (B) after de-metalation. Scale bar: 200 nm. Grey scale range: 240 nm. (C) The load of indentation P for COF particles before and (D) after de-metalation as a function of elastic displacement Δh.
Figure 25B:
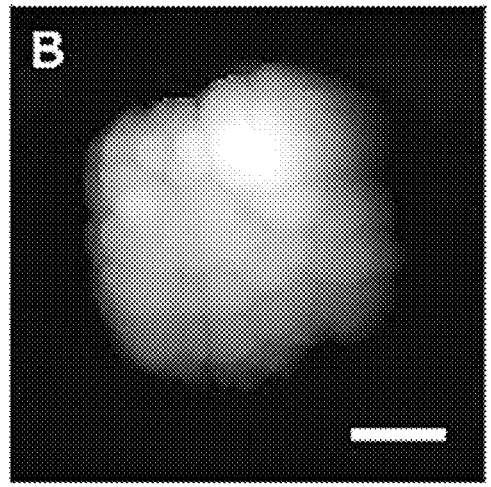

Nano-indentation based on AFM (Nanoscope Dimension 3100) was employed to measure Young's modulus of COF-505 and the de-metalated material. AFM images of the particles were first acquired under non-contact mode (see FIGS. 25A and B), followed by indentation at the summit of the aggregate which is relatively flat.

Following the standard procedure of nano-indentation, the Young's modulus is related to the indentation curve by Eq. (1):

$$S = \frac{dP}{dh} = \beta \frac{2}{\pi} E_{eff} \sqrt{A} \quad (1)$$

Where $$\frac{1}{E_{eff}} = \frac{1-v^2}{E} + \frac{1-v_i^2}{E_i}$$

is the effective elastic modulus of the system, $E_{eff}$, reflecting both the mechanical response of the sample, $E$, and the indenter, $E_i$, and $v$ is Poisson's ratio.

Synthesis and Characterization of COF-505

Figure 2A:
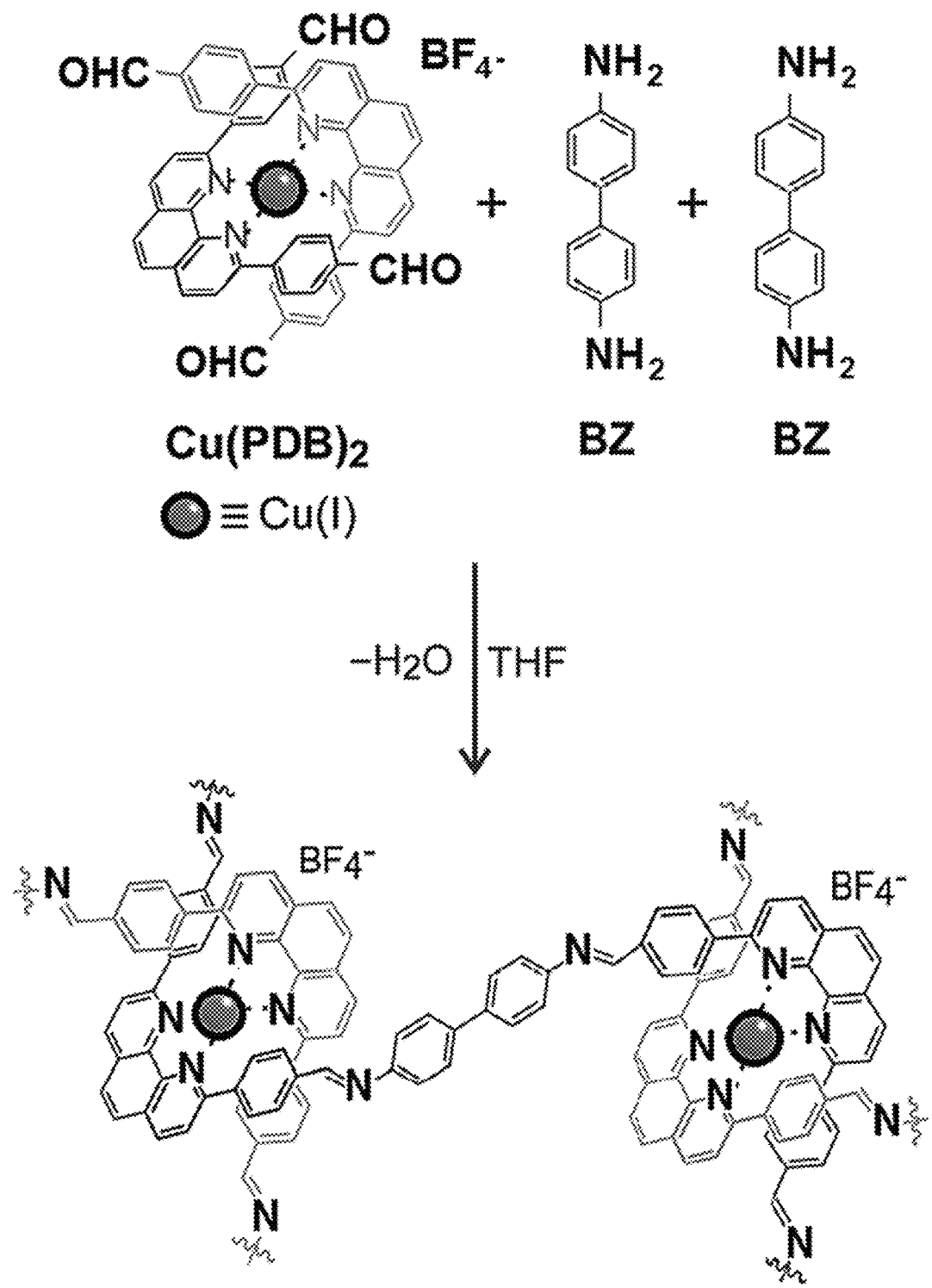
FIG. 2A-B provides an embodiment of a general strategy for the design and synthesis of weaving structures. COF-505 was constructed from organic threads using copper(I) as a template (A) to make an extended weaving structure (B), which can be subsequently de-metalated and re-metalated.
Figure 2B:
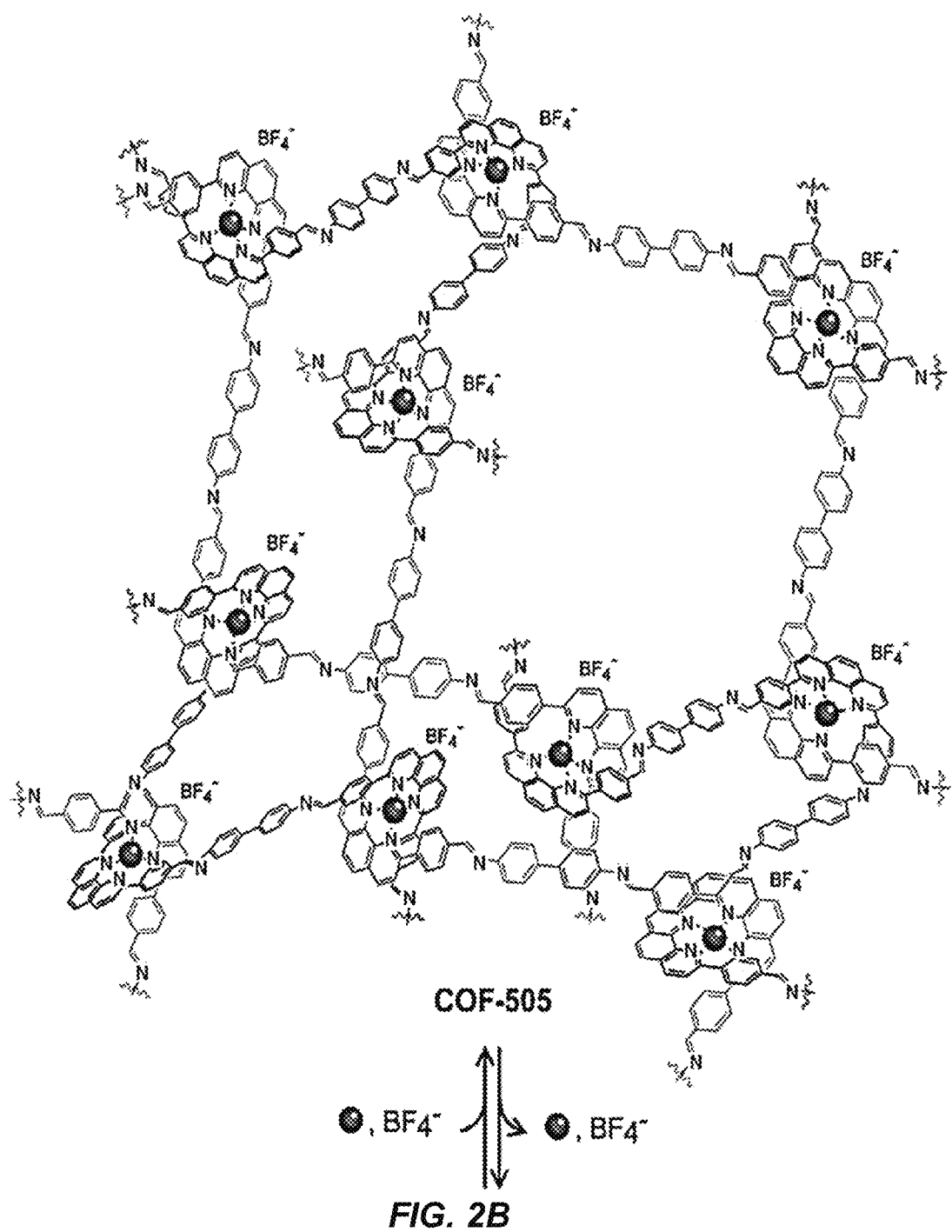
Figure 2B:
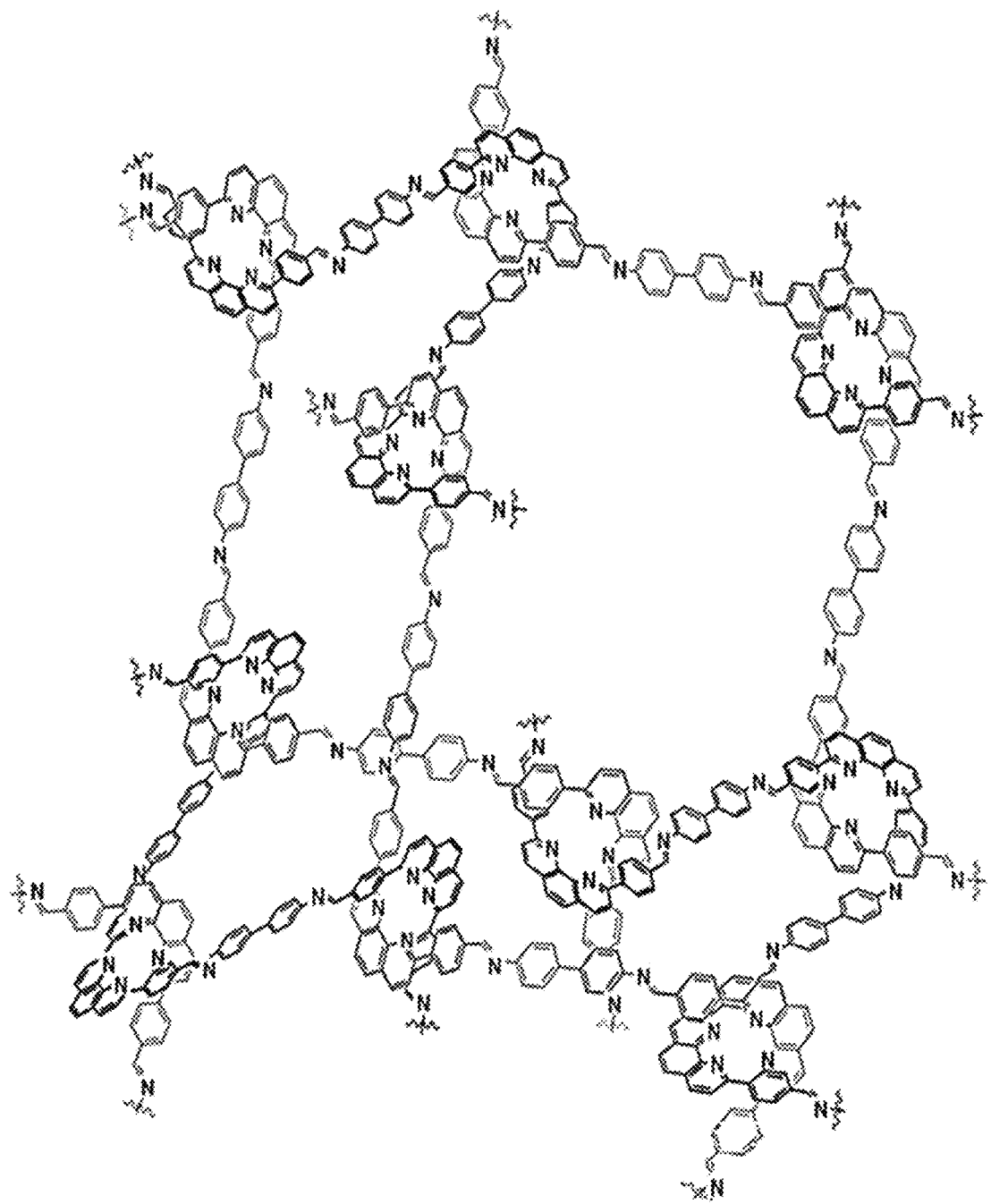

A synthetic strategy to produce COF-505 is presented in FIG. 2, where an aldehyde functionalized derivative is used to exemplify the well-known complex salt Cu(I)-bis[4,4'-(1,10-phenanthroline-2,9-diyl)dibenzaldehyde] tetrafluoroborate, Cu(PBD)$_2$(BF$_4$) (see FIG. 2A). The position of the aldehyde groups approximates a tetrahedral geometry which can be used in reticular synthesis as a building block to be linked with benzidine (BZ) to generate imine-bonded PDB-BZ threads in a woven arrangement with the tetrafluoroborate anions occupying the pores (see FIG. 2B). The orientation of the PDB units in a mutually interlacing fashion ensures that the threads produced from linking of the building units are entirely independent, with the Cu(I) ions serving as templates (points-of-registry) to bring those threads together in a precise manner at well-defined intervals. Because the PDB-BZ threads are topologically independent of the Cu(I) ions, the resulting woven structure is formally a COF (termed COF-505). The overall tetrahedral geometry of the aldehyde units ensures the assembly of the threads into a 3D framework (see FIG. 2B). The topology of this framework is that of diamond as expected from the principles of reticular chemistry. In addition, even after the removal of the Cu(I) ions, the structure and its topology remain intact irrespective of how the threads deviate from their points-of-registry, and upon re-metalating the overall structure is reversibly restored. A ten-fold increase in elasticity was found when going from the metalated to the de-metalated forms of the material.

The copper(I)-bisphenanthroline core of the Cu(PDB)$_2$ (without the aldehyde functionality) has been studied extensively as a discrete molecule for the formation of supramolecular complexes; however, as yet, it has not been used to make extended structures especially of the type discussed here. The tolerance for robust reaction conditions makes this complex suitable for imine COF synthesis, especially in weak acidic conditions. Thus, the tetrahedral building unit, Cu(PDB)$_2$, was designed bearing aldehyde groups in the para positions of the two phenyl substituents (see FIG. 2A). The synthesis of Cu(PDB)$_2$(BF$_4$) molecular complex was carried out by air-free Cu(I) complexation of 4,4'-(1,10-phenanthroline-2,9-diyl)dibenzaldehyde according to a previously reported procedure. The single-crystal structure of this complex revealed a distorted tetrahedral geometry around the Cu(I) center, with a dihedral angle of 57° between the two phenanthroline planes. This distortion likely arises from the n-n interaction between the phenanthroline and neighboring phenyl planes.

COF-505 was synthesized via imine condensation reactions by combining a mixture of Cu(PDB)$_2$(BF$_4$) (15 mg, 0.016 mmol) and BZ (6.0 mg, 0.032 mmol) in tetrahydrofuran (THF, 1 mL) and aqueous acetic acid (6 mol/L, 100 µL). The reaction mixture was sealed in a Pyrex tube and heated at 120° C. for 3 days. The resulting precipitate was collected by centrifugation, washed with anhydrous THF, and then evacuated at 120° C. for 12 h to yield 18.7 mg [94.4% based on Cu(PDB)$_2$(BF$_4$)] of a dark brown crystalline solid (COF-505), which was insoluble in common polar and nonpolar organic solvents.

Fourier-transform infrared spectroscopy (FT-IR) and solid-state nuclear magnetic resonance (NMR) spectroscopy studies were performed on COF-505 to confirm the formation of imine linkages. A molecular analog of COF-505 fragment, Cu(I)-bis[(1,10-phenanthroline-2,9-diyl)bis(phenylene)bis(biphenyl)methanimine)] tetrafluoroborate, Cu(PBM)$_2$(BF$_4$), was used as a model compound and synthesized by condensation of Cu(PDB)$_2$(BF$_4$) and 4-aminobiphenyl. The FT-IR spectrum of COF-505 shows peaks at 1621 and 1196 cm$^{-1}$ [1622 and 1197 cm$^{-1}$ for Cu(PBM)$_2$(BF$_4$)], which are characteristic C=N stretching modes for imine bonds. Furthermore, the $^{13}$C cross-polarization with magic-angle spinning (CPMAS) solid-state NMR spectrum acquired for COF-505 displays a series of peaks from 140 to 160 ppm, similar in shape and occurring at chemical shifts characteristic of those expected for C=N double bonds. In order to differentiate imine bonds from C=N double bonds of the phenanthroline unit, a cross-polarization and polarization inversion (CPPI) technique was applied, which leaves the signal for quaternary $^{13}$C groups unchanged, while the residual tertiary $^{13}$CH signal should approach zero. The decreased intensity of the $^{13}$CH signal under these conditions confirmed the existence of imine CH=N double bond. Overall, these observations served as initial confirmation of having covalently linked imine extended threads in COF-505.

Figure 3A:
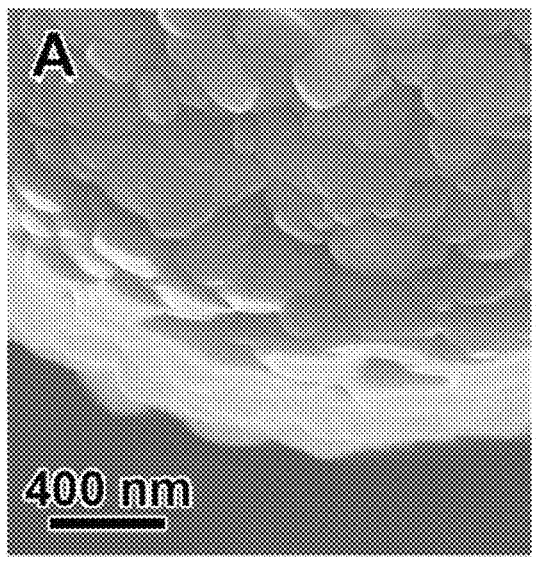
FIG. 3A-G presents morphology and electron microscopy studies of COF-505. (A) Crystallites aggregated on a crystalline sphere observed by SEM. (B) TEM image of a single sub-μm crystal used for 3D-EDT. (C) 2D projection of the reconstructed reciprocal lattice of COF-505 obtained at 298 K from a set of 3D-EDT data. (D) HRTEM image of COF-505 taken with the [1-10] incidence. (E) 2D projected potential map obtained by imposing pgg plane group symmetry on FIG. 1D. (F) Reconstructed 3D electrostatic potential map (threshold: 0.8). (G) Indexed PXRD pattern of the activated sample of COF-505 (black) and the Pawley fitting (gray) from the modeled structure.

Prior to determining the single crystal structure of COF-505, the morphology and purity of the as-synthesized material was analyzed. Using scanning electron microscopy (SEM), crystallites of ~200 nm are aggregated into spheres of 2 μm in diameter (see FIG. 3A), which possibly arises from weak interactions of the synthesized material with the solvent, THF. No other phase was observed from SEM images taken throughout the material.

Figure 3B:
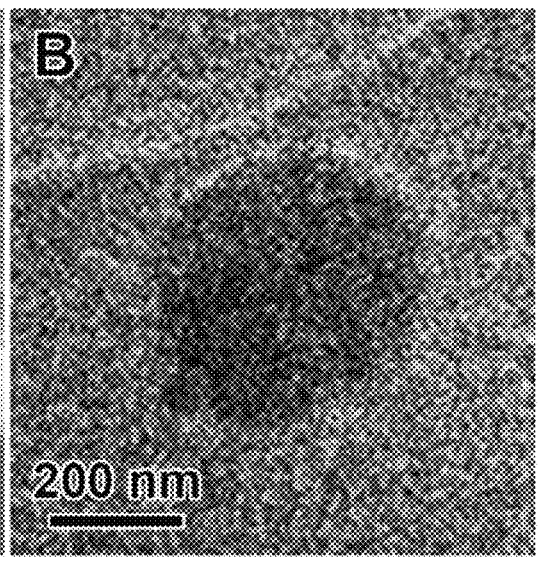
Figure 3C:
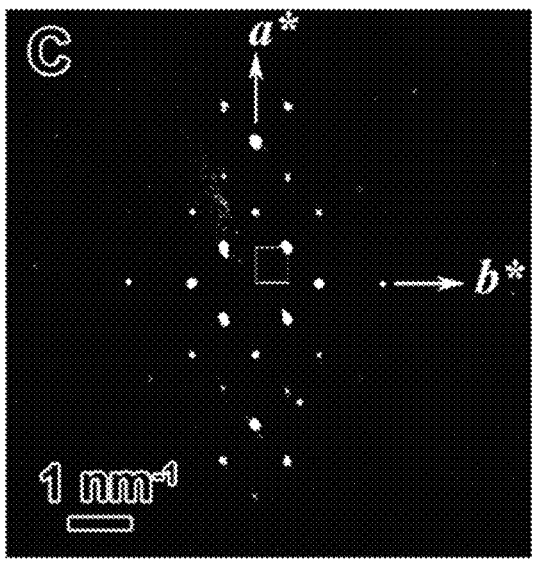
Figure 3D:
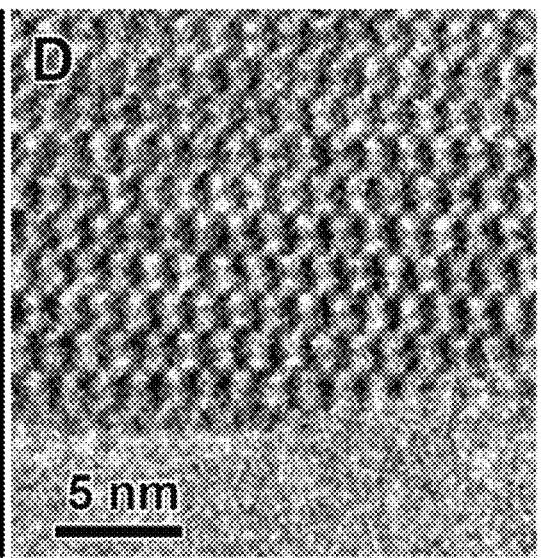
Figure 3E:
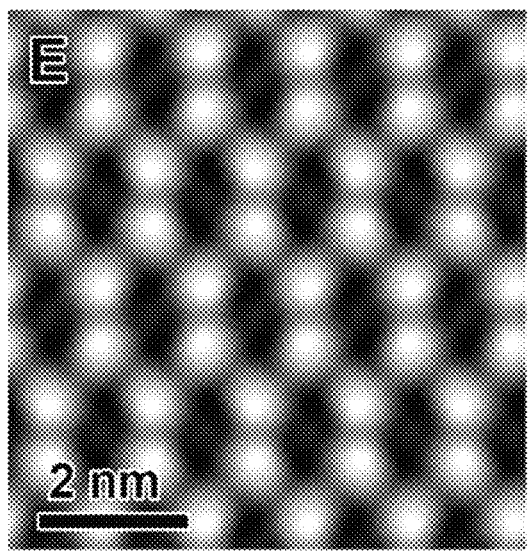
Figure 3F:
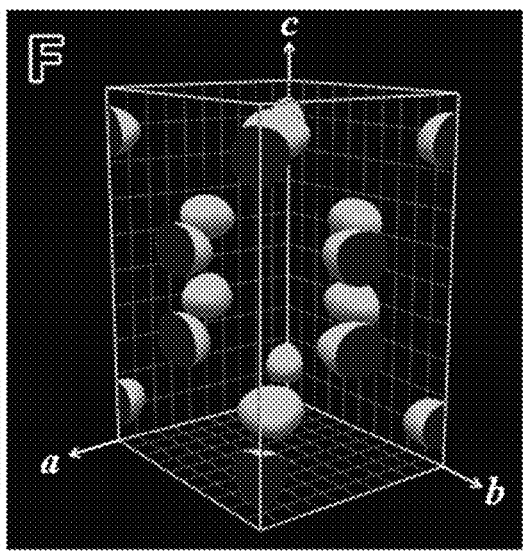
Figure 3G:
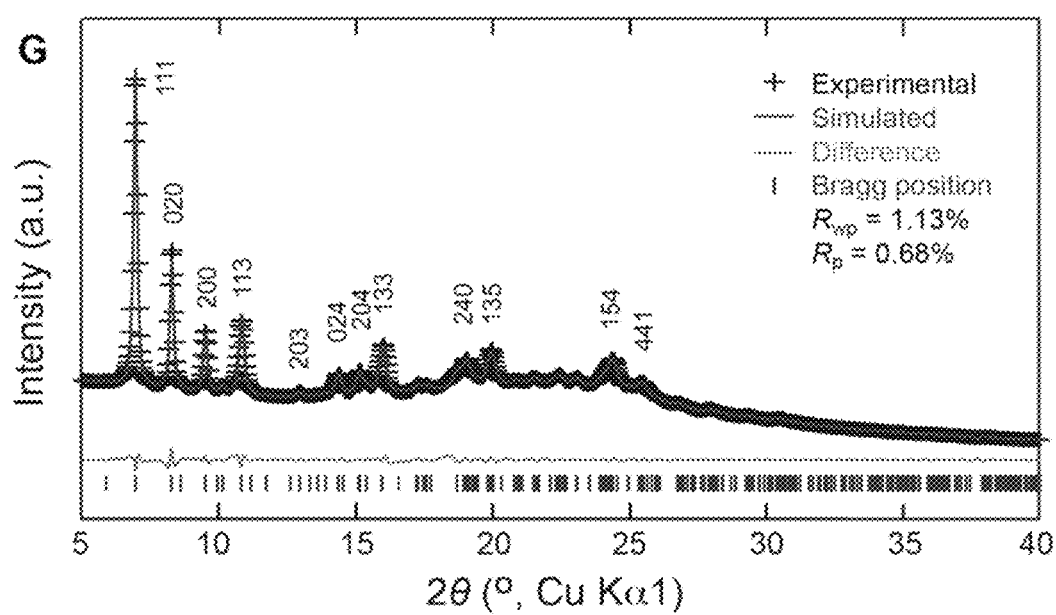

A single submicrometer-sized crystal (see FIG. 3B) from this sample was studied by 3D electron diffraction tomography (3D-EDT). One EDT data set was collected from the COF-505 (see FIG. 3C) by combining specimen tilt and electron-beam tilt in the range of −41.3° to +69.1° with a beam-tilt step of 0.2°. From the acquired data set, 3D reciprocal lattice of COF-505 was constructed that was identified as a C-centered orthorhombic Bravais lattice. The unit cell parameters were a=18.9 Å, b=21.3 Å, c=30.8 Å and V=12399 Å$^3$, which were used to index reflections observed in both powder x-ray diffraction (PXRD) pattern and Fourier diffractograms of high-resolution TEM images (see FIG. 3D to F). The unit cell parameters were further refined to be a=18.6 Å, b=21.4 Å, c=30.2 Å, V=12021 Å$^3$ by Pawley refinement of PXRD pattern (see FIG. 3G). The observed reflection conditions were summarized as hkl: h+k=2n; hk0: h,k=2n; h0l: h=2n; 0kl: k=2n, suggesting five possible space groups, Cm2a (No. 39), Cmma (No. 67), Cmca (No. 64), Cc2a (No. 41) and Ccca (No. 68). Three of them, Cm2a, Cmma, and Ccca, were excluded, as their projected symmetries along [1-10] did not coincide with that of HRTEM image, pgg (see FIG. 3E). Furthermore, by performing Fourier analysis of the HRTEM images and imposing symmetry to the reflections, Cu(I) positions were determined from the reconstructed 3D potential map (see FIG. 3F). The structure of COF-505 was built in Materials Studio by putting Cu(PDB)$_2$ units at copper positions and connecting them through biphenyl (reacted BZ) molecules. The chemical compositions were determined by elemental analysis, therefore once the number of copper atoms in one unit cell was obtained, the numbers of other elements in one unit cell were also determined, which indicates that the unit-cell framework is constructed by 8 Cu(PDB)$_2$ and 16 biphenyl units. However, symmetry operations of the space group Cmca requires two PDB units connected to one copper onto a mirror plane perpendicular to a axis, which is not energetically favorable geometry. The final space group determined, Cc2a, was used to build and optimize a structure model. The PXRD pattern calculated from this model is consistent with the experimental pattern of activated COF-505.

According to the refined model, COF-505 crystallizes in a diamond (dia) network with the distorted tetrahedral building units Cu(PBD)$_2$ and biphenyl linkers BZ linked through trans imine bonds. As a result, covalently linked adamantane-like cages 19 Å by 21 Å by 64 Å are obtained and elongated along the c-axis (dimensions are calculated based on Cu-to-Cu distances). This size allows two diamond networks of identical frameworks to form the crystal. These frameworks are mutually interpenetrating (when the Cu centers are considered) in COF-505 crystals along the c direction, where the frameworks are related by a C$_2$ rotation along the b-axis, leaving sufficient space for BF$_4^-$ counterions. When the structure is de-metalated, as demonstrated below, the COF is mutually woven (see FIG. 2B).

Figure 4A:
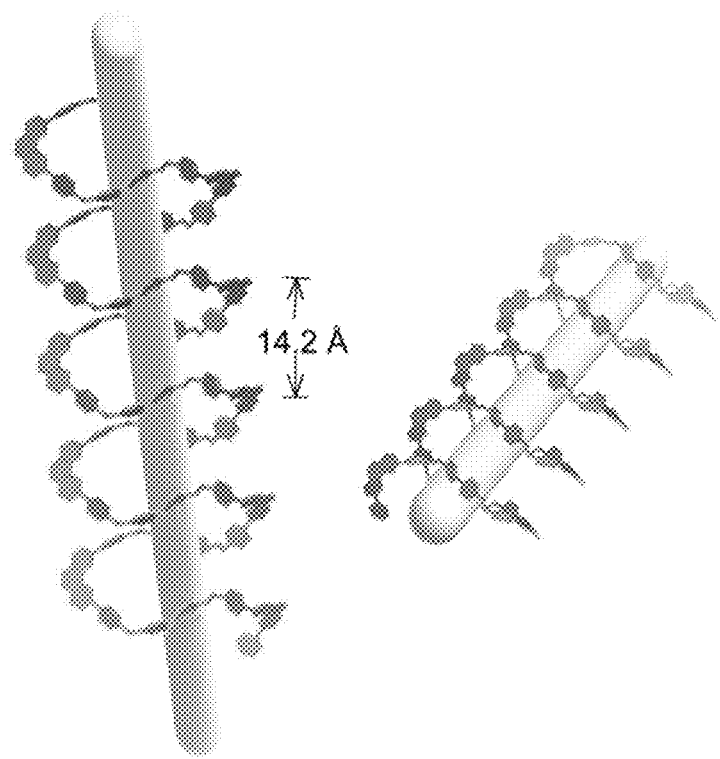
FIG. 4A-D presents an embodiment of a single crystal structure of COF-505. (A) The weaving structure of COF-505 consists of chemically identical helices (as shown, helices that have opposite chirality) with the pitch of 14.2 Å. (B) Helices (top) propagate in the [1-10] direction, while the helices (bottom) propagate in the [110] direction with copper (I) ions as the points-of-registry. (C) Neighboring helices are weaved with helices having opposite chirality to form the overall framework. (D) Dark gray and medium gray helices and their $C_2$ symmetry related lighter gray and light gray copies are mutually weaved. Additional parallel helices in (C) and (D) are omitted for clarity.
Figure 4B:
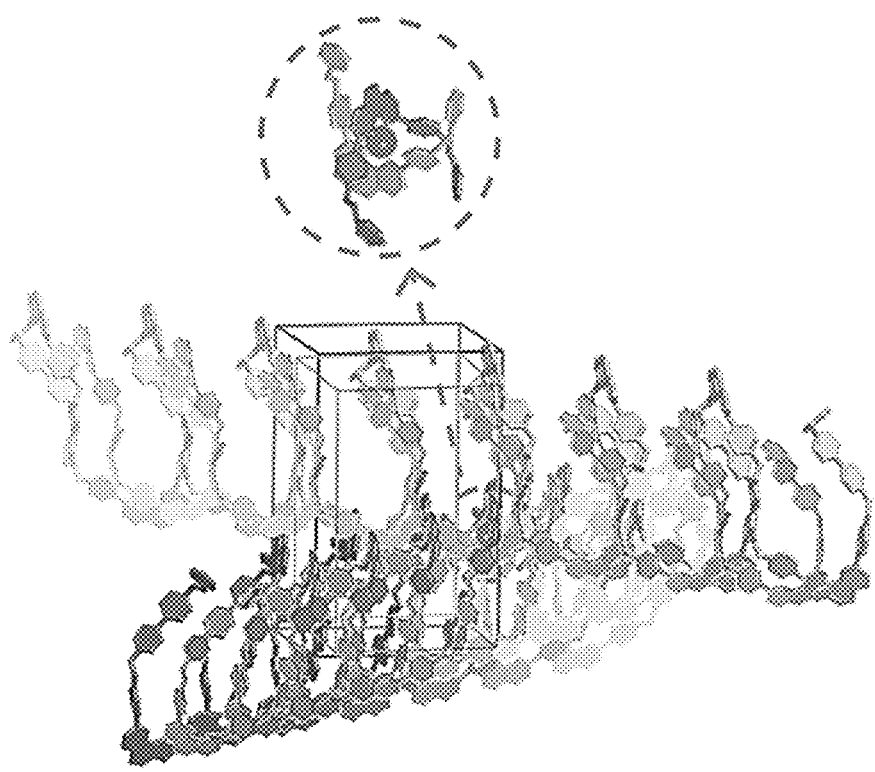
Figure 4C:
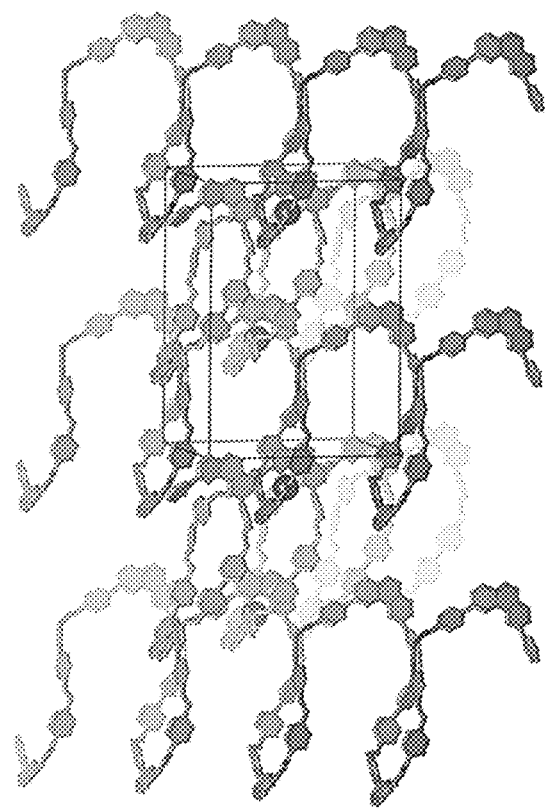
Figure 4D:
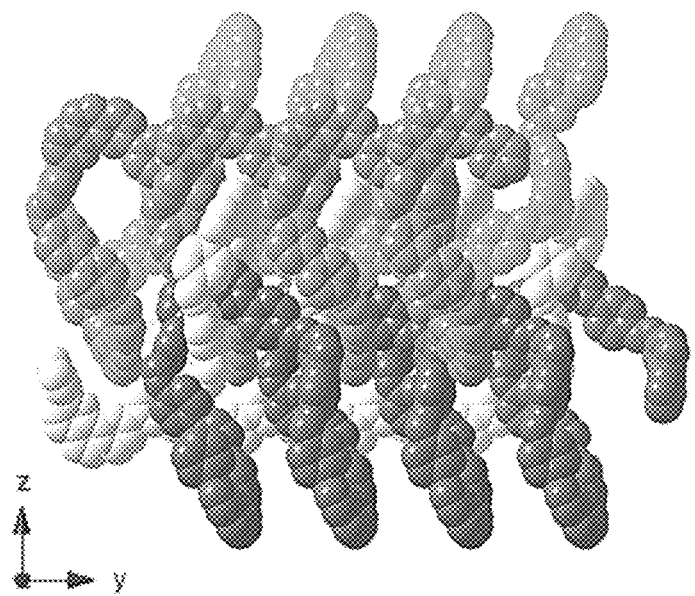

Fundamentally, each of the threads making up the framework is a helix (see FIG. 4A). For clarity, only a fragment of one weaving framework is shown. The helices are entirely made of covalently linked organic threads. As expected, they are weaving and being held by Cu(I) ions at their points-of-registry (see FIG. 4B). These threads are propagating in two different directions along [110] and [−110]. Although the helices are chemically identical, they have opposite chirality giving rise to an overall racemic weaving framework (see FIGS. 4C and D) of the same topology as in FIG. 1B. It was noted that in the context of reticular chemistry, the points-of-registry play an important role in crystallizing otherwise difficult to crystallize threads and to do so into two- or three-dimensional frameworks. This arrangement is in stark contrast to the parallel manner in which such one-dimensional objects commonly pack in the solid-state.

The exemplary COF-505 structure is a woven fabric of helices. Experiments were performed to remove the Cu centers and examine the properties of the material before and after de-metalation. Heating COF-505 in a KCN methanol-water solution yielded a de-metalated material. Using inductively coupled plasma (ICP) analysis, 92-97% of the Cu(I) copper ions had been removed. The dark brown color of COF-505 [from the copper-phenanthroline metal-to-ligand charge transfer (MLCT)] changed to pale-yellow as de-metalation proceeded. Although the crystallinity of de-metalated material decreased compared to COF-505, SEM images show similar morphology before and after de-metalation. Additionally, the imine linkages were also maintained; the FT-IR peaks at 1621 and 1195 cm$^{-1}$ are consistent with those of COF-505 (1621 and 1196 cm$^{-1}$). Furthermore, the material could be re-metalated with Cu(I) ions by stirring in a CH$_3$CN/CH$_3$OH solution of Cu(CH$_3$CN)$_4$(BF$_4$) to give back crystalline COF-505. This re-metalated COF-505 has identical crystallinity to the original as-synthesized COF-505 as evidenced by the full retention of the intensity and positions of the peaks in the PXRD. In the FT-IR spectrum, the peak representing imine C=N stretch was retained, indicating that the framework is chemically stable and robust under such reaction conditions.

Given the facileness with which de-metalation can be carried out and the full retention of the structure upon re-metalation can be achieved, the elastic behavior of the metalated and de-metalated COF-505 was examined. A single particle of each of these two samples was indented by a conical tip of an atomic force microscope and the load-displacement curves were recorded for both loading and unloading process. The effective Young's moduli (neglecting the anisotropy of the elasticity) of the two COF-505 materials was ~12.5 GPa and 1.3 GPa for the metalated and de-metalated particles, respectively. Remarkably, this ten-fold ratio in elasticity upon de-metalation of COF-505 is similar to the elasticity ratio for porous MOFs to polyethylene. The distinct increase of elasticity could be attributed to the loose interaction between the threads upon removal of copper. Moreover, the elasticity of the original COF-505 could be fully recovered after the process of de-metalation and re-metalation, being facilitated by the structure of weaving helical threads that easily 'zip' and 'unzip' at their points-of-registry. The large difference in elasticity modulus is caused by loss of Cu(I) ions, which in total only represent a minute mole percentage (0.67 mol %) of the COF-505 structure.

Figure 25C:
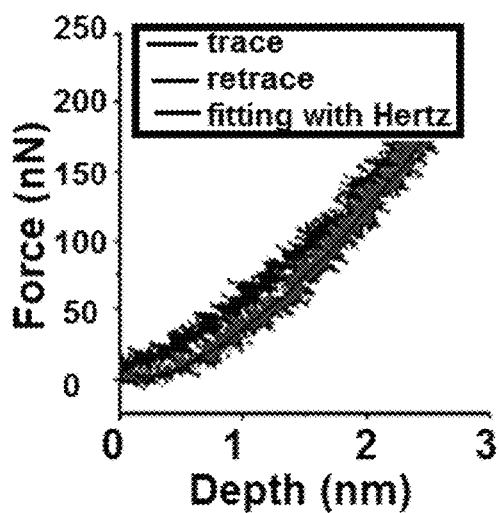
Figure 25D:
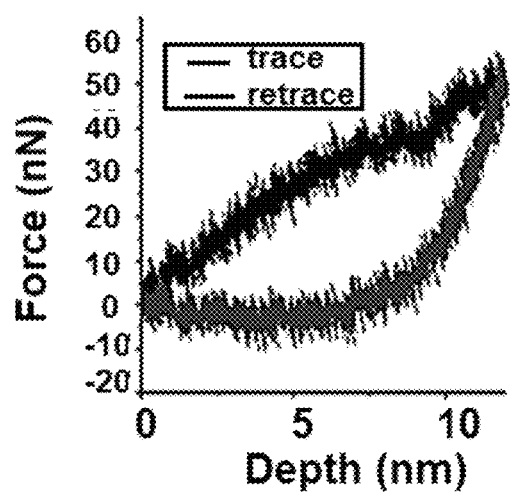

For COF-505, it was found that the indentation curve is close to pure elastic deformation at small depth described by the Hertz theory (see FIG. 25C). Its Young's modulus is calculated to be 12.5 GPa using a tip radius of 15 nm, and Poisson's ratio of v=0.3. This value lies within the typical range of MOFs. The measured Young's moduli of other COF-505 particles and re-metalated COF-505 are within 30% deviation. On the contrary, the de-metalated material is very soft and shows significant plastic deformation under moderate force (see FIGS. 25C and D). Applying Eq. (1) a Young's modulus around 1.3 GPa was obtained when assuming a tip radius of 15 nm and a tip angle of 30°.

Figure 26:
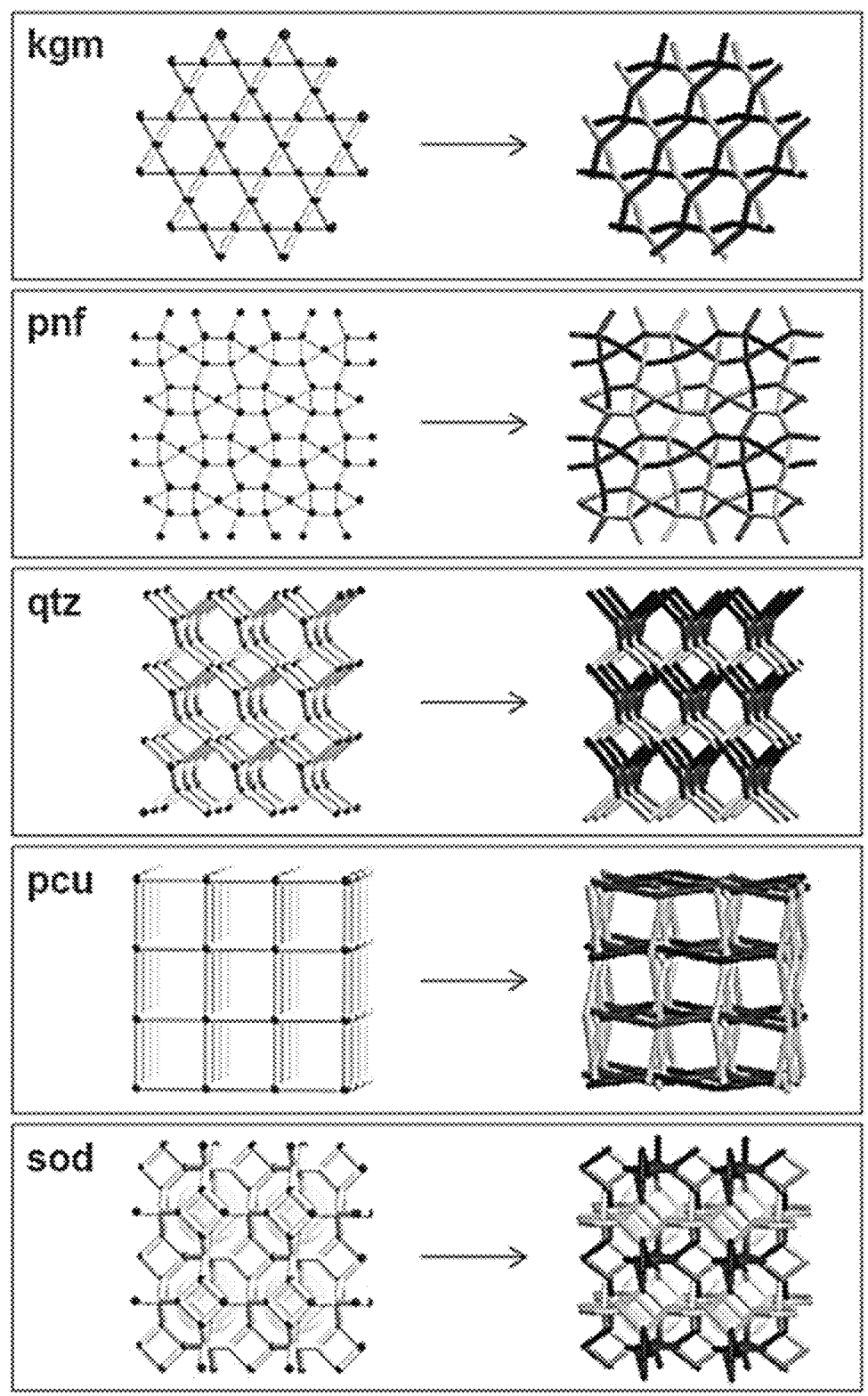
FIG. 26 demonstrates that the same type weaving of threads observed in COF-505 can be used to make many other COFs based on common net topologies (e.g., kgm, pnf, qtz, pcu, and sod).

The weaving strategy reported here is potentially applicable to the conversion of other network topologies to weaving structures as illustrated in FIG. 26. In addition to the dia net of COF-505, a variety of other two- and three-dimensional topologies can also be achieved by weaving of threads (variously colored) using metal ions as points-of-registry. Tetrahedrally coordinated metal complexes with two ligands can be employed as tetratopic building units in reticular synthesis to construct weaving structures of corresponding topologies (e.g., pnf, qtz and sod). Metal ions with an octahedral coordination geometry, which provides another type of points-of-registry by coordinating three ligands, can also be used to synthesize weaving structures (e.g., kgm and pcu).

A number of embodiments have been described herein. Nevertheless, it will be understood that various modifications may be made without departing from the spirit and scope of this disclosure. Accordingly, other embodiments are within the scope of the following claims.

What is claimed is:

1. A woven covalent organic framework that comprises a plurality of long organic threads that are mutually interlaced at regular intervals so as to form points-of-registry, wherein the points-of-registry have a structure represented by Formula V:

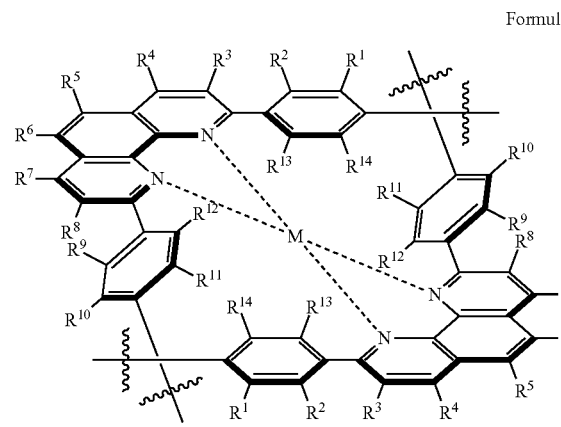

Formula V wherein, M is a metal ion, metal, or a metal complex that is bound to nitrogen atoms, or alternatively M is absent;

wherein the long organic threads comprise covalently bound alternating linking ligands, wherein the alternating linking ligands comprise linking ligands that have a structure represented by Formula I:

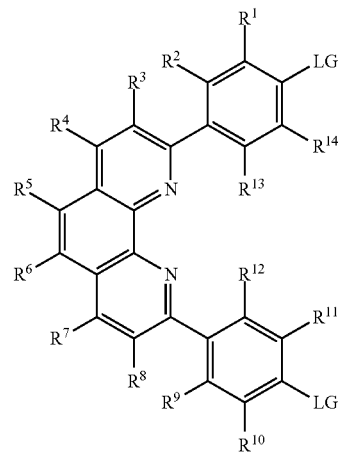

Formula I covalently bound to linking ligands that have a structure represented by Formula II, III, or IV:

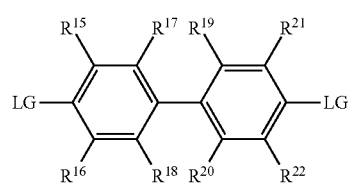

Formula II

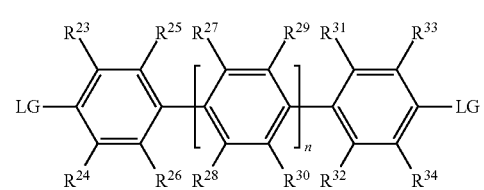

Formula III

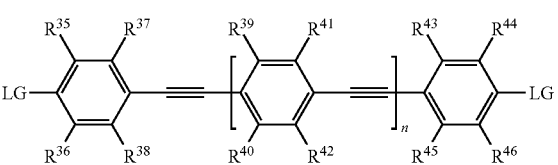

Formula IV wherein,
$R^1$-$R^{10}$, and $R^{15}$-$R^{46}$ are each independently selected from H, FG, ($C_1$-$C_{12}$)alkyl, substituted ($C_1$-$C_{12}$)alkyl, ($C_2$-$C_{12}$)alkenyl, substituted ($C_2$-$C_{12}$)alkenyl, ($C_2$-$C_{12}$)alkynyl, substituted ($C_2$-$C_{12}$)alkynyl, hetero-($C_1$-$C_{12}$)alkyl, substituted hetero-($C_1$-$C_{12}$)alkyl, hetero-($C_2$-$C_{12}$)alkenyl, substituted hetero-($C_2$-$C_{12}$)alkenyl, hetero-($C_2$-$C_{12}$)alkynyl, substituted hetero-($C_2$-$C_{12}$)alkynyl, ($C_3$-$C_{12}$)cycloalkyl, substituted ($C_3$-$C_{12}$)cycloalkyl, aryl, substituted aryl, heterocycle, substituted heterocycle, —C($R^{50}$)$_3$, —CH($R^{50}$)$_2$, —CH$_2$$R^{50}$, —C($R^{51}$)$_3$, —CH($R^{51}$), —CH$_2$$R^{51}$, —OC($R^{50}$)$_3$, —OCH($R^{50}$)$_2$, —OCH$_2$$R^{50}$, —OC($R^{51}$)$_3$, —OCH($R^{51}$), —OCH$_2$$R^{51}$, or $R^1$-$R^{10}$ when adjacent can form a substituted or unsubstituted ring selected from the group comprising cycloalkyl, aryl and heterocycle;
$R^{11}$-$R^{14}$ are each independently selected from H, D, FG, ($C_1$-$C_3$)alkyl, substituted ($C_1$-$C_3$)alkyl, hetero-($C_1$-$C_3$)alkyl, or substituted hetero-($C_1$-$C_3$)alkyl;

R⁵⁰ is selected from the group comprising FG, $(C_1-C_{12})$alkyl, $(C_1-C_{12})$substituted alkyl, $(C_1-C_{12})$alkenyl, substituted $(C_1-C_{12})$alkenyl, $(C_1-C_{12})$alkynyl, substituted $(C_1-C_{12})$alkynyl, hetero-$(C_1-C_{12})$alkyl, substituted hetero-$(C_1-C_{12})$alkyl, hetero-$(C_1-C_{12})$alkenyl, substituted hetero-$(C_1-C_2)$alkenyl, hetero-$(C_1-C_{12})$alkynyl, substituted hetero-$(C_1-C_{12})$alkynyl;

R⁵¹ is one or more substituted or unsubstituted rings selected from the group consisting of cycloalkyl, aryl, and heterocycle; and FG is selected from the group consisting of halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitrites, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_3$, $Ge(SH)_3$, $AsO_3H$, $AsO_3H$, $P(SH)_3$, $As(SH)_3$, $SO_3H$, $Si(OH)_3$, $Ge(OH)_3$, $Sn(OH)_3$, $Si(SH)_3$, $Ge(SH)_3$, $Sn(SH)_3$, $AsO_3H$, $AsO_3H$, $P(SH)_3$, and $As(SH)_3$;

LG is each independently selected from the group consisting of boronic acid, nitriles, aldehyde, amine, halide, hydroxyl, acyl halide, carboxylic acid, and acetic anhydride; and n is an integer from 1 to 10, wherein the LG groups of Formula I and the LG groups of Formula II, III, or IV are covalently bound together;

wherein the points-of-registry may be metalated to comprise coordinated metals, metal ions, or metal containing complexes, or the points-of-registry may be de-metalated.

2. The woven covalent organic framework of claim 1, wherein the covalent bond formed between the LG groups of Formula I and the LG groups of Formula II, III, or IV, has the structure of:

,

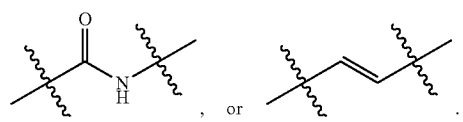

, or

3. The woven covalent organic framework of claim 1, wherein the alternating linking ligands comprise linking ligands that have a structure represented by Formula I(b):

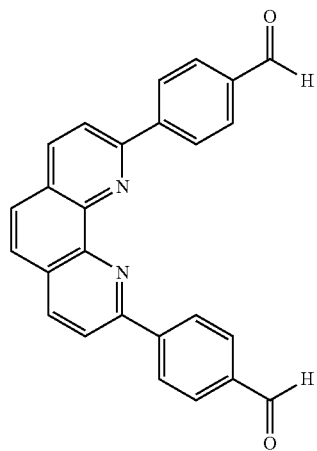

Formula I(b)

covalently bound to linking ligands that have a structure of represented by Formula II(b), III(b), or IV(b):

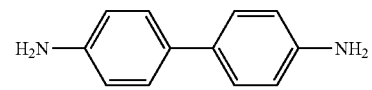

Formula II(b)

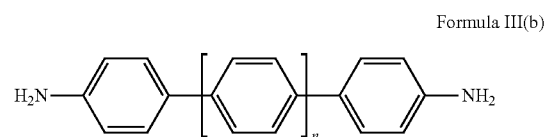

Formula III(b)

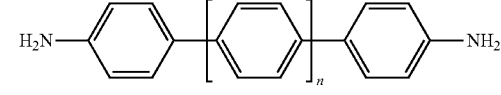

Formula IV(b)

wherein, n is an integer from 1 to 10; and wherein the linking ligands having the structure of Formula I(b) are covalently bound to the linking ligands having the structure of Formula II(b), III(b) or IV(b) via an imine bond:

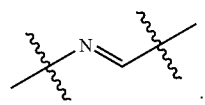

4. The woven covalent organic framework of claim 1, wherein the woven framework is demetalated.

5. The woven covalent organic framework of claim 1, wherein the woven framework is metalated or re-metalated.

6. The woven covalent organic framework of claim 1, wherein the woven covalent organic framework exhibits at least an eight fold increase in elasticity when the woven covalent organic framework is de-metalated versus being metalated.

7. The woven covalent organic framework of claim 1, wherein the woven organic framework has the structure and properties of COF-505:

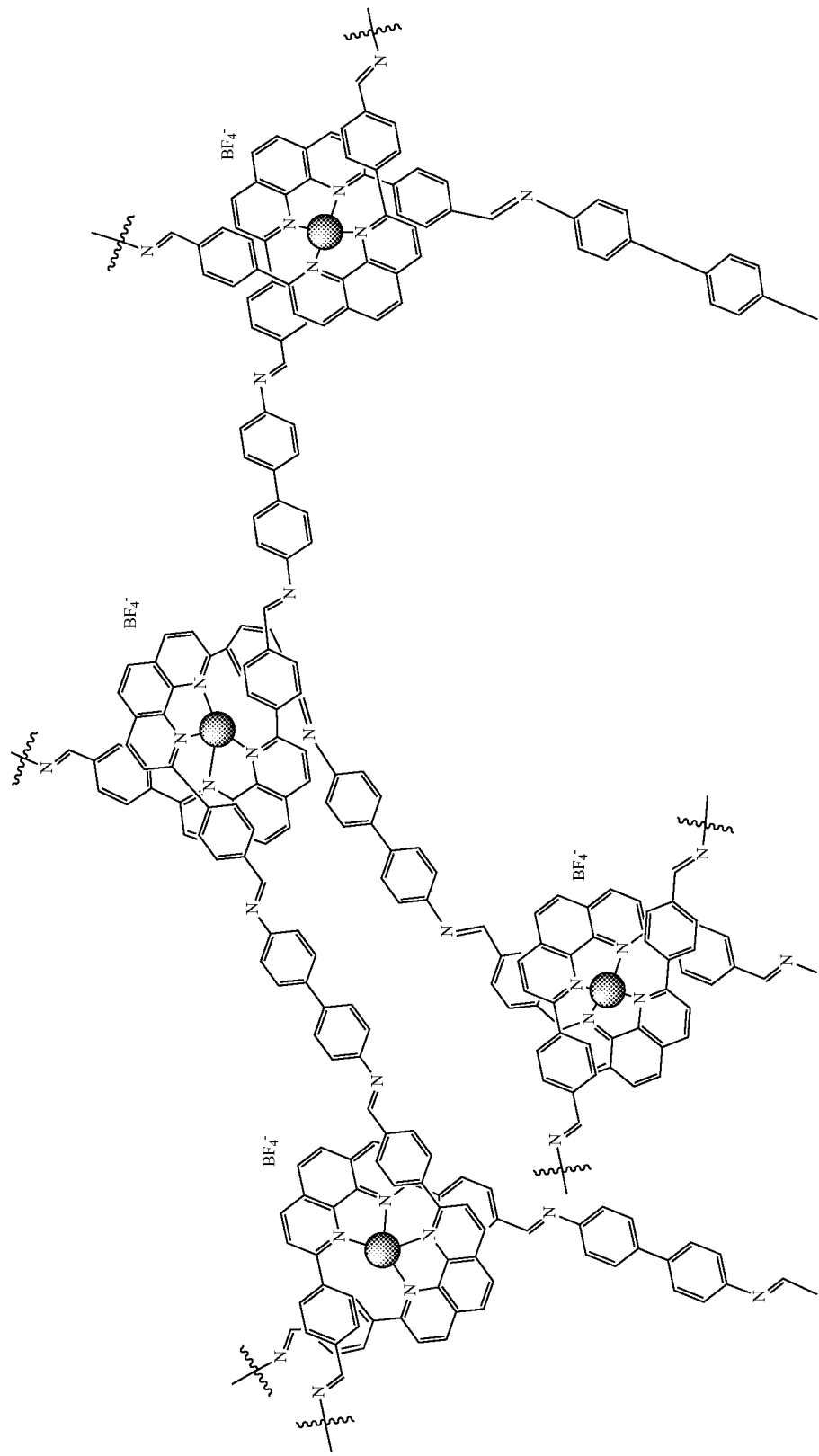

-continued
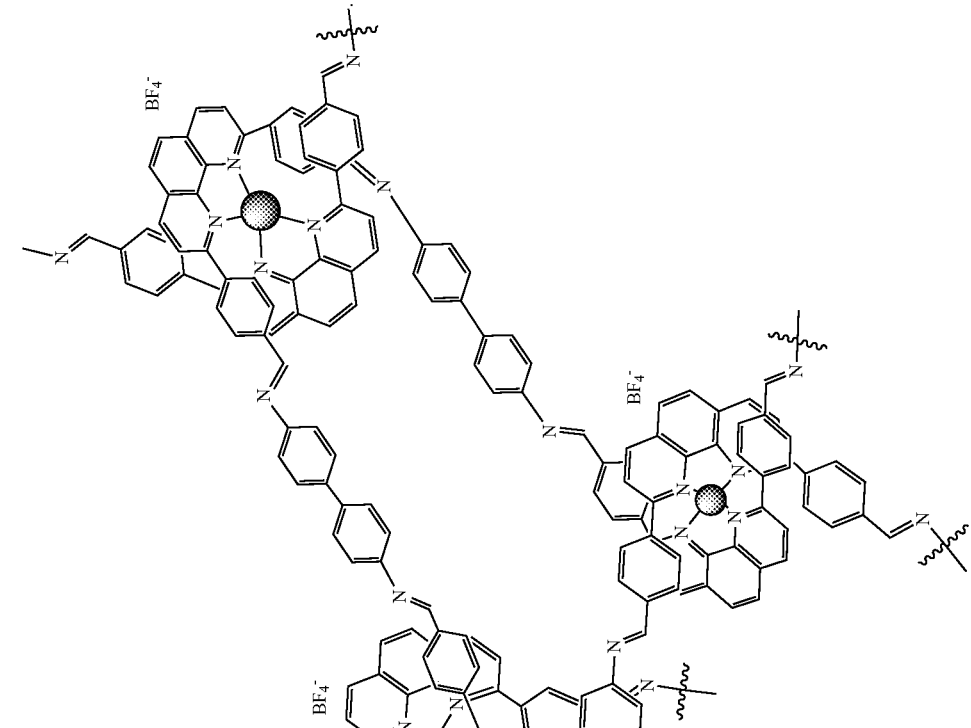
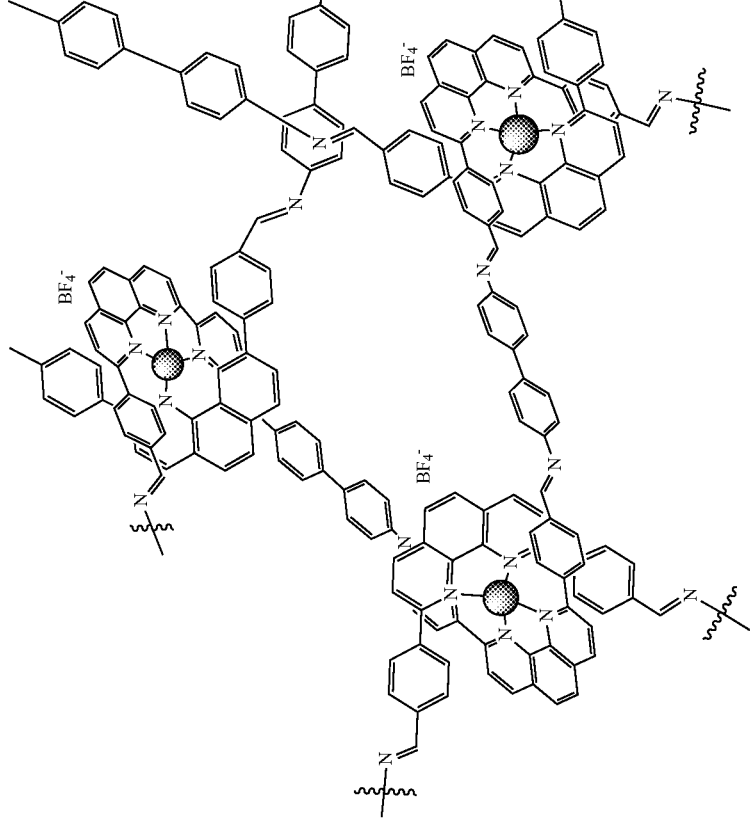
COF-505

8. The woven covalent organic framework of claim 1, wherein the points of registry comprise tetrahedrally coordinated metal ions.

9. The woven covalent organic framework of claim 8, wherein the woven covalent organic framework has a topology selected from pnf, qtz, and sod.

10. The woven covalent organic framework of claim 8, wherein the woven covalent organic framework is de-metalated.

11. The woven covalent organic framework of claim 1, wherein the points of registry comprise octahedrally coordinated metal ions.

12. The woven covalent organic framework of claim 11, wherein the woven covalent organic framework has a topology selected from kgm and pcu.

13. The woven covalent organic framework of claim 11, wherein the woven covalent organic framework is de-metalated.

14. A resilient material comprising a woven covalent organic framework of claim 1.

15. The resilient material of claim 14, wherein the resilient material is used in shape-memory material development or biomedical applications.

* * * * *